(12) United States Patent
Lei et al.

(10) Patent No.: US 11,701,433 B2
(45) Date of Patent: Jul. 18, 2023

(54) COMPLEXES FOR DELIVERY OF ANTIGENIC PEPTIDES

(71) Applicant: The Regents of the University of Michigan, Ann Arbor, MI (US)

(72) Inventors: Yu Lei, Ann Arbor, MI (US); Yee Sun Tan, Ann Arbor, MI (US); Kanokwan Sansanaphongpricha, Ann Arbor, MI (US); Duxin Sun, Ann Arbor, MI (US); Hongwei Chen, Ann Arbor, MI (US); Hongxiang Hu, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 411 days.

(21) Appl. No.: 16/619,802

(22) PCT Filed: Jun. 1, 2018

(86) PCT No.: PCT/US2018/035623
§ 371 (c)(1),
(2) Date: Dec. 5, 2019

(87) PCT Pub. No.: WO2018/226529
PCT Pub. Date: Dec. 13, 2018

(65) Prior Publication Data
US 2020/0129640 A1    Apr. 30, 2020

Related U.S. Application Data

(60) Provisional application No. 62/515,234, filed on Jun. 5, 2017.

(51) Int. Cl.
*A61K 9/00*      (2006.01)
*A61K 47/69*     (2017.01)
(Continued)

(52) U.S. Cl.
CPC ...... *A61K 47/6929* (2017.08); *A61K 39/0003* (2013.01); *A61K 39/0011* (2013.01);
(Continued)

(58) Field of Classification Search
CPC .................................................. A61K 47/6929
See application file for complete search history.

(56) References Cited

U.S. PATENT DOCUMENTS

| | | | |
|---|---|---|---|
| 2012/0263777 A1 | 10/2012 | Woo et al. | |
| 2015/0065858 A1 | 3/2015 | Chen et al. | |

FOREIGN PATENT DOCUMENTS

| | | | | |
|---|---|---|---|---|
| EP | 3322731 A1 * | 5/2018 | ......... | A61K 39/3955 |
| WO | WO 2013/059831 A1 | 4/2013 | | |
| WO | WO 2017/147597 A1 | 2/2017 | | |

OTHER PUBLICATIONS

Ahn. Self-DNA, STING-dependent signaling and the origins of autoinflammatory disease. Curr Opin Immunol. Dec. 2014;31:121-6.

(Continued)

*Primary Examiner* — Paul W Dickinson
(74) *Attorney, Agent, or Firm* — Casimir Jones, S.C.; Jason R. Bond

(57) ABSTRACT

The present invention provides methods, compositions, systems, and kits comprising nano-satellite complexes and/or serum albumin carrier complexes, which are used for modulating antigen-specific immune response (e.g., enhancing anti-tumor immunity). In certain embodiments, the nano-satellite complexes comprise: a) a core nanoparticle complex comprising a biocompatible coating surrounding a nanoparticle core; b) at least one satellite particle attached to, or absorbed to, the biocompatible coating; and c) an antigenic component conjugated to, or absorbed to, the at least one satellite particle component. In certain embodiments, the complexes further comprise: d) an type I inter- (Continued)

feron agonist agent. In some embodiments, the serum albumin complexes comprise: a) at least part of a serum albumin protein, b) an antigenic component conjugated to the carrier protein, and c) a type I interferon agonist agent.

6 Claims, 39 Drawing Sheets

Specification includes a Sequence Listing.

(51) Int. Cl.
| | | |
|---|---|---|
| A61K 47/64 | (2017.01) | |
| A61P 35/00 | (2006.01) | |
| A61K 39/00 | (2006.01) | |
| A61K 39/02 | (2006.01) | |
| A61K 39/118 | (2006.01) | |
| A61K 39/385 | (2006.01) | |
| B82Y 5/00 | (2011.01) | |

(52) U.S. Cl.
CPC ............ *A61K 39/02* (2013.01); *A61K 39/118* (2013.01); *A61K 39/385* (2013.01); *A61K 47/643* (2017.08); *A61K 47/646* (2017.08); *A61K 47/6923* (2017.08); *A61P 35/00* (2018.01); *A61K 2039/55561* (2013.01); *A61K 2039/572* (2013.01); *A61K 2039/60* (2013.01); *A61K 2039/622* (2013.01); *B82Y 5/00* (2013.01)

(56) References Cited

OTHER PUBLICATIONS

Barber. STING: infection, inflammation and cancer. Nat Rev Immunol. Dec. 2015;15(12):760-70.
Bass et al., SOX2 is an amplified lineage-survival oncogene in lung and esophageal squamous cell carcinomas. Nat Genet. Nov. 2009;41(11):1238-42.
Beane et al., Characterizing the impact of smoking and lung cancer on the airway transcriptome using RNA-Seq. Cancer Prev Res (Phila). Jun. 2011;4(6):803-17.
Boumahdi et al., SOX2 controls tumour initiation and cancer stem-cell functions in squamous-cell carcinoma. Nature. Jul. 10, 2014;511(7508):246-50.
Bullock et al., Antigen density presented by dendritic cells in vivo differentially affects the number and avidity of primary, memory, and recall CD8+ T cells. J Immunol. Feb. 15, 2003;170(4):1822-9.
Chithrani et al., Determining the size and shape dependence of gold nanoparticle uptake into mammalian cells. Nano Lett. Apr. 2006;6(4):662-8.
Chou et al., The emerging role of SOX2 in cell proliferation and survival and its crosstalk with oncogenic signaling in lung cancer. Stem Cells. Dec. 2013;31(12):2607-19.
Corrales et al., The host STING pathway at the interface of cancer and immunity. J Clin Invest. Jul. 1, 2016;126(7):2404-11.
Deng et al., STING-Dependent Cytosolic DNA Sensing Promotes Radiation-Induced Type I Interferon-Dependent Antitumor Immunity in Immunogenic Tumors. Immunity. Nov. 20, 2014;41(5):843-52.
Fan et al., Nanoparticle Drug Delivery Systems Designed to Improve Cancer Vaccines and Immunotherapy. Vaccines (Basel). Aug. 27, 2015;3(3):662-85.
Ferris et al., Nivolumab for Recurrent Squamous-Cell Carcinoma of the Head and Neck. N Engl J Med. Nov. 10, 2016;375(19):1856-1867.
Fu et al., Estimating accuracy of RNA-Seq and microarrays with proteomics. BMC Genomics. Apr. 16, 2009;10:161.

Fu et al., Fu J. et al., (2015). STING agonist formulated cancer vaccines can cure established tumors resistant to PD-1 blockade. Sci Transl Med 7, 283ra252. Sci Transl Med. Apr. 15, 2015;7(283):283ra52.
Gao et al., Loss of IFN-γ Pathway Genes in Tumor Cells as a Mechanism of Resistance to Anti-CTLA-4 Therapy. Cell. Oct. 6, 2016;167(2):397-404.e9.
Gentles et al., The prognostic landscape of genes and infiltrating immune cells across human cancers. Nat Med. Aug. 2015;21(8):938-945.
Guo et al., NLRX1 Sequesters STING to Negatively Regulate the Interferon Response, Thereby Facilitating the Replication of HIV-1 and DNA Viruses. Cell Host Microbe. Apr. 13, 2016;19(4):515-528.
Guo et al., Large scale comparison of gene expression levels by microarrays and RNAseq using TCGA data. PLoS One. Aug. 20, 2013;8(8):e71462.
Hanson et al., Nanoparticulate STING agonists are potent lymph node-targeted vaccine adjuvants. J Clin Invest. Jun. 2015;125(6):2532-46.
Herbst et al., Predictive correlates of response to the anti-PD-L1 antibody MPDL3280A in cancer patients. Nature. Nov. 27, 2014;515(7528):563-7.
International Search Report and Written Opinion for PCT/US2018/035623 dated Sep. 26, 2018. 12 pages.
Ishikawa et al., STING is an endoplasmic reticulum adaptor that facilitates innate immune signalling. Nature. Oct. 2, 2008;455(7213):674-8.
Ishikawa et al., STING regulates intracellular DNA-mediated, type I interferon-dependent innate immunity. Nature. Oct. 8, 2009;461(7265):788-92.
Jounai et al., The Atg5 Atg12 conjugate associates with innate antiviral immune responses. Proc Natl Acad Sci U S A. Aug. 28, 2007;104(35):14050-5.
Konno et al., Cyclic dinucleotides trigger ULK1 (ATG1) phosphorylation of STING to prevent sustained innate immune signaling. Cell. Oct. 24, 2013;155(3):688-98.
Lau et al., DNA tumor virus oncogenes antagonize the cGAS-STING DNA-sensing pathway. Science. Oct. 30, 2015;350(6260):568-71.
Lei et al., EGFR-targeted mAb therapy modulates autophagy in head and neck squamous cell carcinoma through NLRX1-TUFM protein complex. Oncogene. Sep. 8, 2016;35(36):4698-707.
Lei et al., Evaluation of SOX2 as a potential marker for ameloblastic carcinoma. Oral Surg Oral Med Oral Pathol Oral Radiol. May 2014;117(5):608-616.e1.
Lei et al., Telltale tumor infiltrating lymphocytes (TIL) in oral, head & neck cancer. Oral Oncol. Oct. 2016;61:159-65.
Lei et al., The mitochondrial proteins NLRX1 and TUFM form a complex that regulates type I interferon and autophagy. Immunity. Jun. 29, 2012;36(6):933-46.
Li et al., PD-1/SHP-2 inhibits Tc1/Th1 phenotypic responses and the activation of T cells in the tumor microenvironment. Cancer Res. Feb. 1, 2015;75(3):508-518.
Li et al., RSEM: accurate transcript quantification from RNA-Seq data with or without a reference genome. BMC Bioinformatics. Aug. 4, 2011;12:323.
Liu et al., Sox2 cooperates with inflammation-mediated Stat3 activation in the malignant transformation of foregut basal progenitor cells. Cell Stem Cell. Mar. 7, 2013;12(3):304-15.
Marioni et al., RNA-seq: an assessment of technical reproducibility and comparison with gene expression arrays. Genome Res. Sep. 2008;18(9):1509-17.
Marur et al., HPV-associated head and neck cancer: a virus-related cancer epidemic. Lancet Oncol. Aug. 2010;11(8):781-9.
Mocan et al., In Vitro Administration of Gold Nanoparticles Functionalized with MUC-1 Protein Fragment Generates Anticancer Vaccine Response via Macrophage Activation and Polarization Mechanism. J Cancer. May 15, 2015;6(6):583-92.
Moore et al., NLRX1 is a regulator of mitochondrial antiviral immunity. Nature. Jan. 31, 2008;451(7178):573-7.
Moroishi et al., The Hippo Pathway Kinases LATS1/2 Suppress Cancer Immunity. Cell. Dec. 1, 2016;167(6):1525-1539.e17.

(56) References Cited

OTHER PUBLICATIONS

Network, C. G. A., Comprehensive genomic characterization of head and neck squamous cell carcinomas. Nature. Jan. 29, 2015;517(7536):576-82.
Newman et al., Robust enumeration of cell subsets from tissue expression profiles. Nat Methods. May 2015;12(5):453-7.
Nguyen et al.,Clinical blockade of PD1 and LAG3—potential mechanisms of action. Nat Rev Immunol. Jan. 2015;15(1):45-56.
Nookaew et al., A comprehensive comparison of RNA-Seq-based transcriptome analysis from reads to differential gene expression and cross-comparison with microarrays: a case study in *Saccharomyces cerevisiae*. Nucleic Acids Res. Nov. 1, 2012;40(20):10084-97.
Onken et al., A surprising cross-species conservation in the genomic landscape of mouse and human oral cancer identifies a transcriptional signature predicting metastatic disease. Clin Cancer Res. Jun. 1, 2014;20(11):2873-84.
Peng et al., Epigenetic silencing of TH1-type chemokines shapes tumour immunity and immunotherapy. Nature. Nov. 12, 2015;527(7577):249-53.
Ribas et al., Association of Pembrolizumab With Tumor Response and Survival Among Patients With Advanced Melanoma. JAMA. Apr. 19, 2016;315(15):1600-9.
Rizvi et al., Cancer immunology. Mutational landscape determines sensitivity to PD-1 blockade in non-small cell lung cancer. Science. Apr. 3, 2015;348(6230):124-8.
Robinson et al., edgeR: a Bioconductor package for differential expression analysis of digital gene expression data. Bioinformatics. Jan. 1, 2010;26(1):139-40.
Rudin et al., Comprehensive genomic analysis identifies SOX2 as a frequently amplified gene in small-cell lung cancer. Nat Genet. Oct. 2012;44(10):1111-6.
Rusinova et al., Interferome v2.0: an updated database of annotated interferon-regulated genes. Nucleic Acids Res. Jan. 2013;41(Database issue):D1040-6.
Saitoh et al., Atg9a controls dsDNA-driven dynamic translocation of STING and the innate immune response. Proc Natl Acad Sci U S A. Dec. 8, 2009;106(49):20842-6.
Schreiber et al., Cancer immunoediting: integrating immunity's roles in cancer suppression and promotion. Science. Mar. 25, 2011;331(6024):1565-70.
Seth et al., Identification and characterization of MAVS, a mitochondrial antiviral signaling protein that activates NF-kappaB and IRF 3. Cell. Sep. 9, 2005;122(5):669-82.
Siegle et al., SOX2 is a cancer-specific regulator of tumour initiating potential in cutaneous squamous cell carcinoma. Nat Commun. Jul. 31, 2014;5:4511.
Silva et al., Development of functionalized nanoparticles for vaccine delivery to dendritic cells: a mechanistic approach. Nanomedicine (Lond). Dec. 2014;9(17):2639-56.
Sistigu et al., Cancer cell-autonomous contribution of type I interferon signaling to the efficacy of chemotherapy. Nat Med. Nov. 2014;20(11):1301-9.
Starr, Encouraging Results for Pembrolizumab in Head and Neck Cancer. Am Health Drug Benefits. Aug. 2015;8(Spec Issue):16.
Stransky et al., The mutational landscape of head and neck squamous cell carcinoma. Science. Aug. 26, 2011;333(6046):1157-60.
Subramanian et al., Gene set enrichment analysis: a knowledge-based approach for interpreting genome-wide expression profiles. Proc Natl Acad Sci U S A. Oct. 25, 2005;102(43):15545-50.
Sun et al., Cyclic GMP-AMP synthase is a cytosolic DNA sensor that activates the type I interferon pathway. Science. Feb. 15, 2013;339(6121):786-91.
Tan et al., Mitigating SOX2-potentiated Immune Escape of Head and Neck Squamous Cell Carcinoma with a STING-inducing Nanosatellite Vaccine. Clin Cancer Res. Sep. 1, 2018;24(17):4242-4255.
Uziela et al., Probe Region Expression Estimation for RNA-Seq Data for Improved Microarray Comparability. PLoS One. May 12, 2015;10(5):e0126545.
Virgin et al., Autophagy genes in immunity. Nat Immunol. May 2009;10(5):461-70.
Wang et al., MapSplice: accurate mapping of RNA-seq reads for splice junction discovery. Nucleic Acids Res. Oct. 2010;38(18):e178.
Woo et al., Innate immune recognition of cancer. Annu Rev Immunol. 2015;33:445-74.
Woo et al., STING-dependent cytosolic DNA sensing mediates innate immune recognition of immunogenic tumors. Immunity. Nov. 20, 2014;41(5):830-42.
Woo et al., The STING pathway and the T cell-inflamed tumor microenvironment. Trends Immunol. Apr. 2015;36(4):250-6.
Wu et al., Cyclic GMP-AMP is an endogenous second messenger in innate immune signaling by cytosolic DNA. Science. Feb. 15, 2013;339(6121):826-30.
Xia et al., Deregulation of STING Signaling in Colorectal Carcinoma Constrains DNA Damage Responses and Correlates With Tumorigenesis. Cell Rep. Jan. 12, 2016;14(2):282-97.
Yang et al., STAT3 Inhibition Enhances the Therapeutic Efficacy of Immunogenic Chemotherapy by Stimulating Type 1 Interferon Production by Cancer Cells. Cancer Res. Sep. 15, 2015;75(18):3812-22.
Zaretsky et al., Mutations Associated with Acquired Resistance to PD-1 Blockade in Melanoma. N Engl J Med. Sep. 1, 2016;375(9):819-29.
Zhang et al., NLRC3, a member of the NLR family of proteins, is a negative regulator of innate immune signaling induced by the DNA sensor STING. Immunity. Mar. 20, 2014;40(3):329-41.
Zitvogel et al., Type I interferons in anticancer immunity. Nat Rev Immunol. Jul. 2015;15(7):405-14.

\* cited by examiner

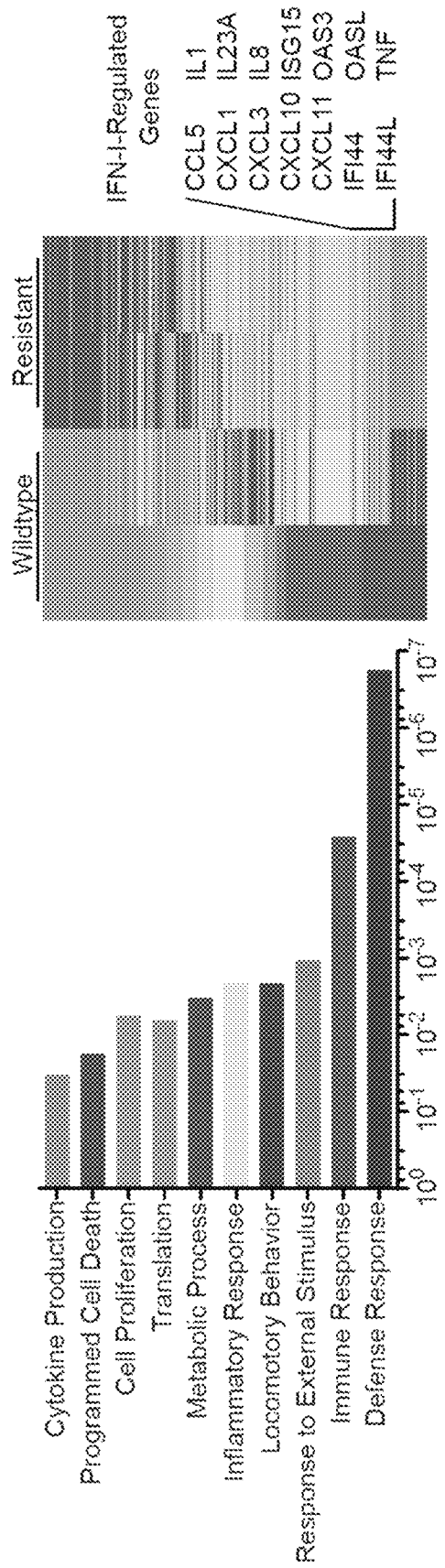

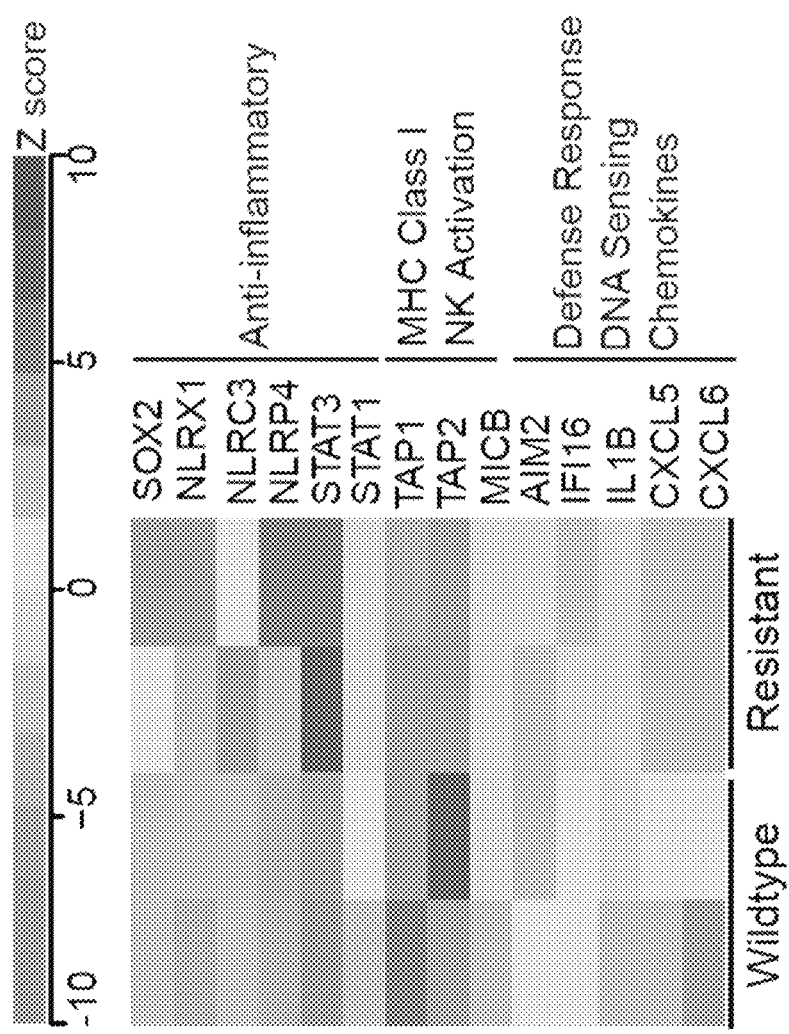

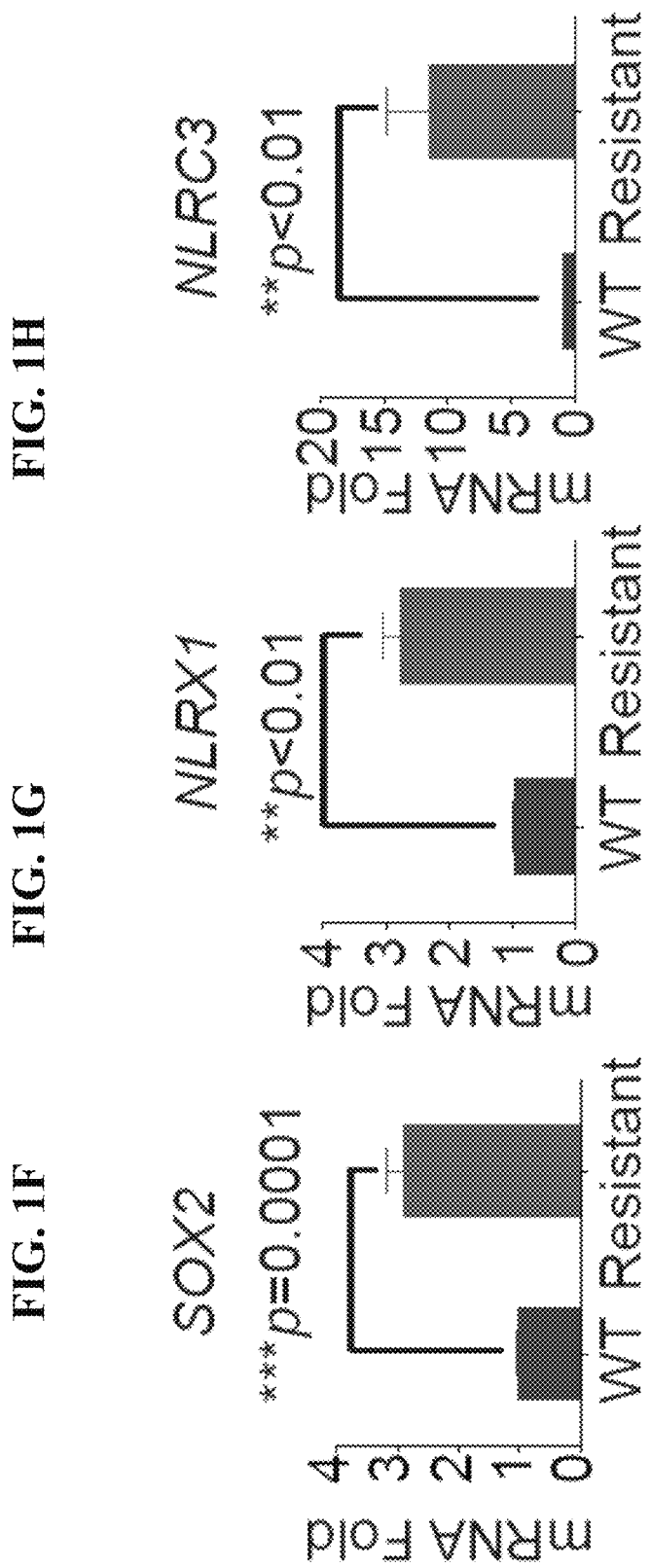

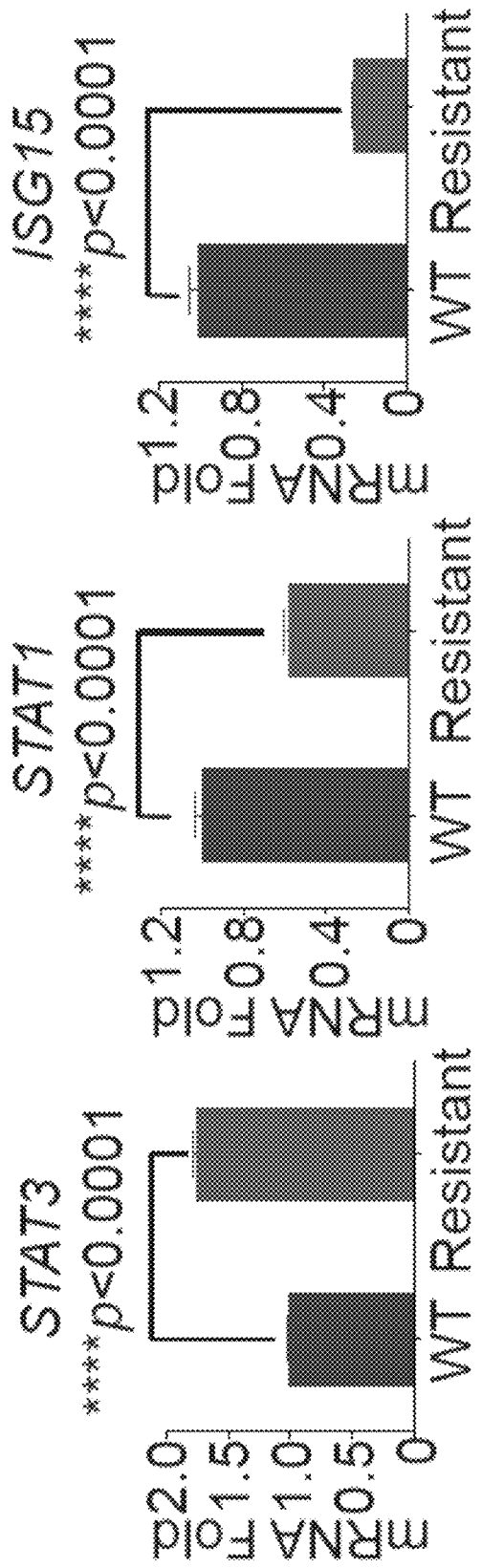

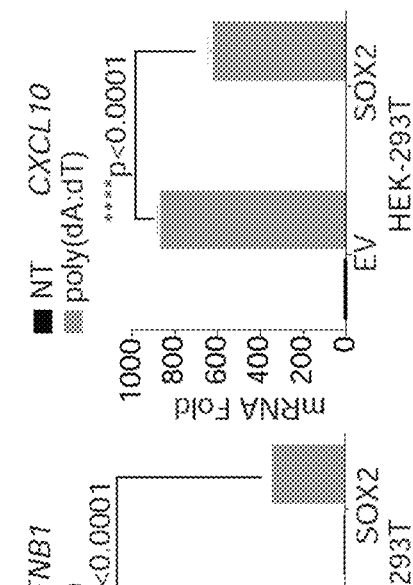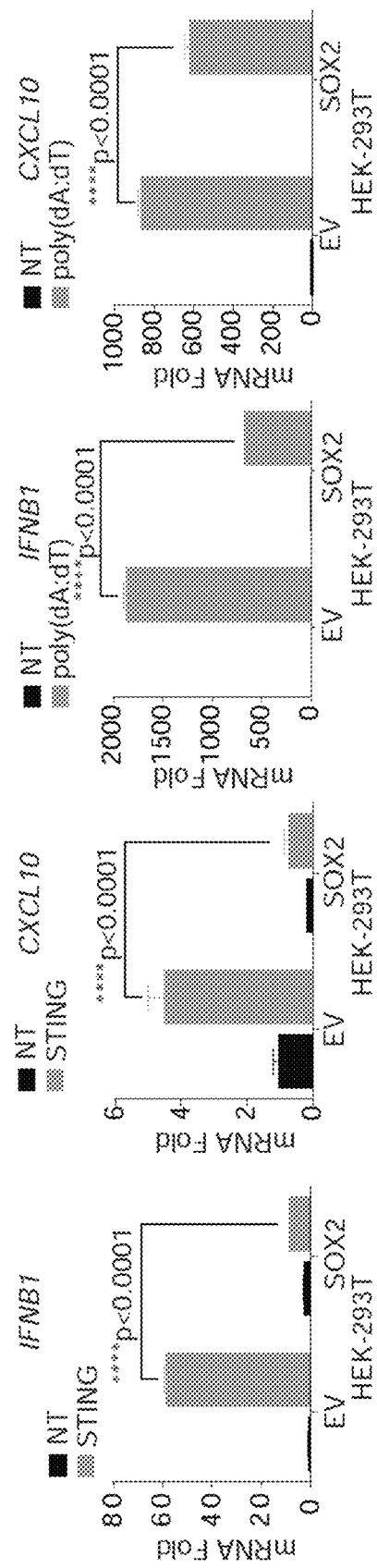

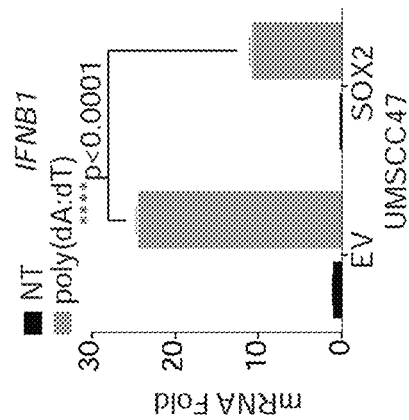
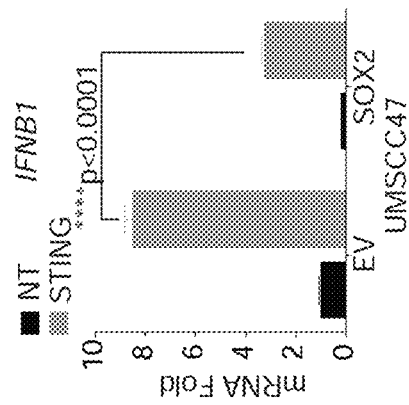
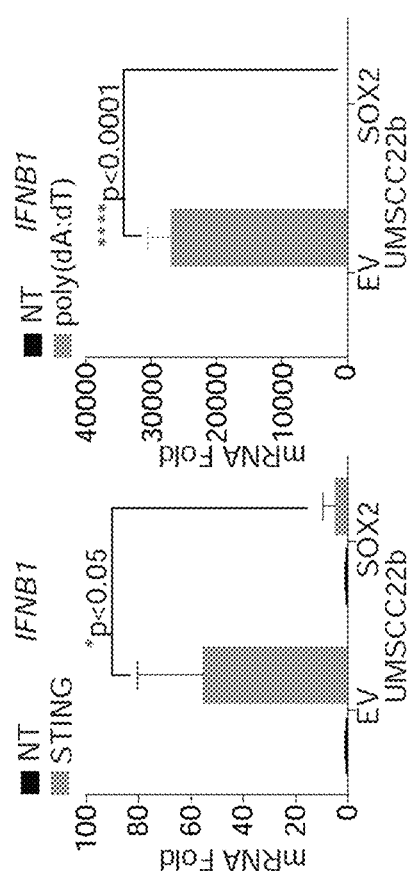
FIG. 3H  FIG. 3I  FIG. 3J  FIG. 3K

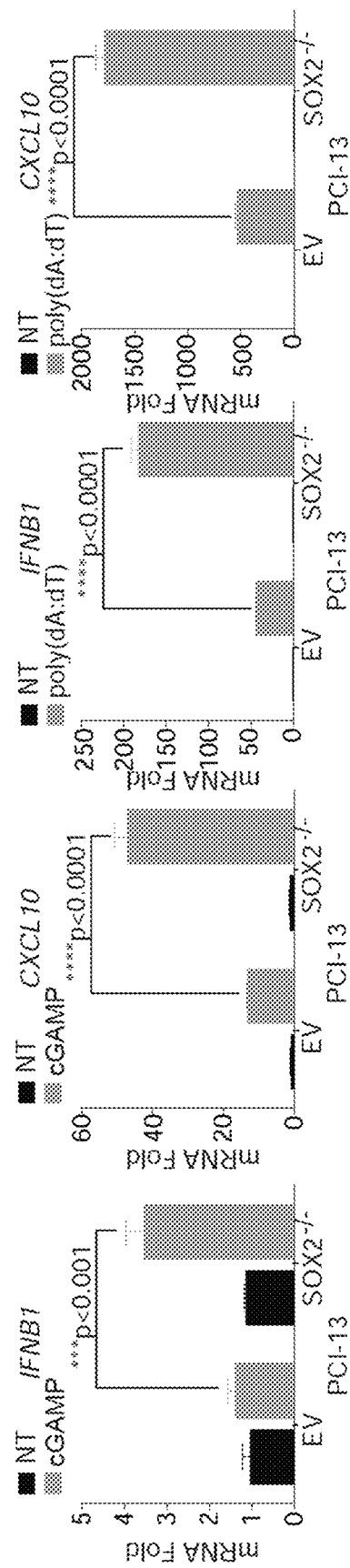

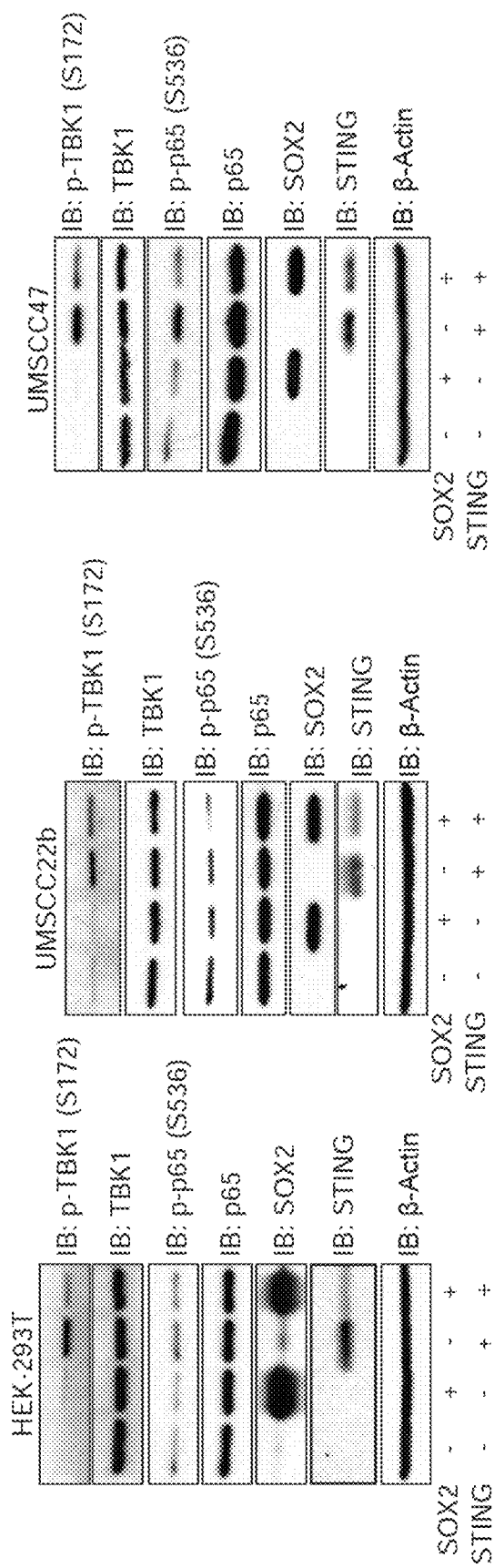

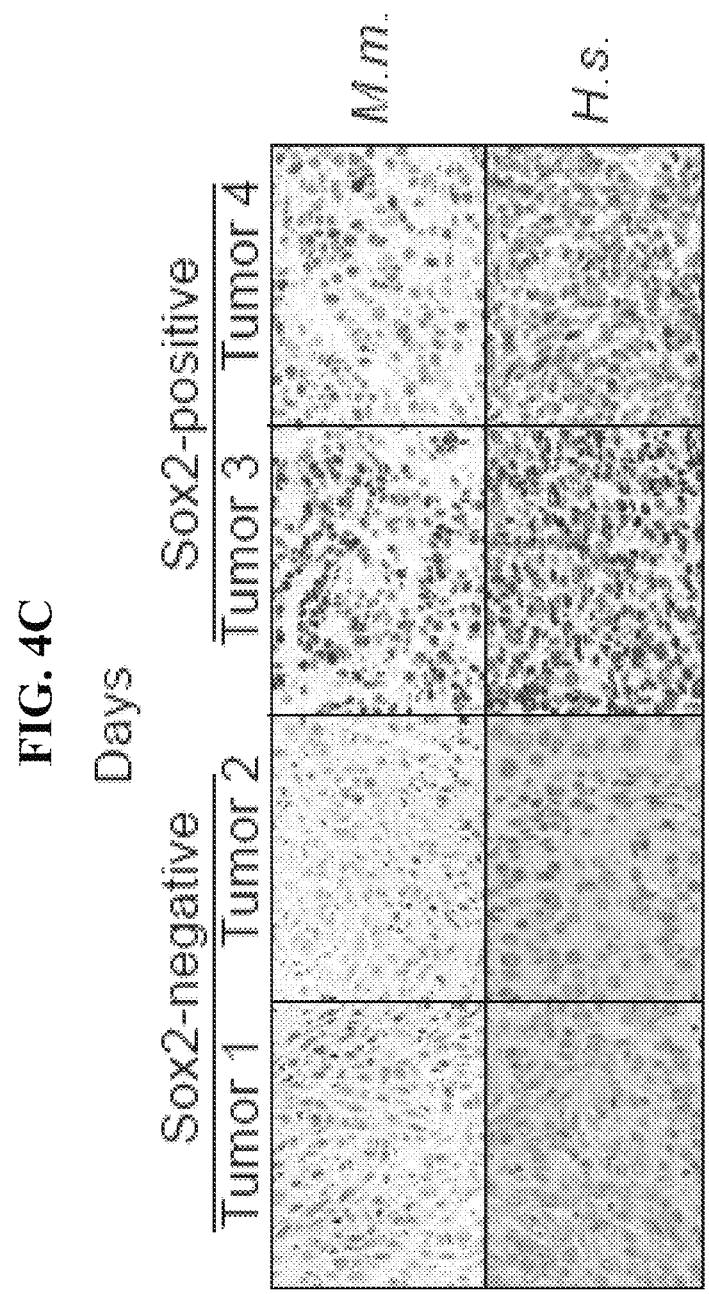

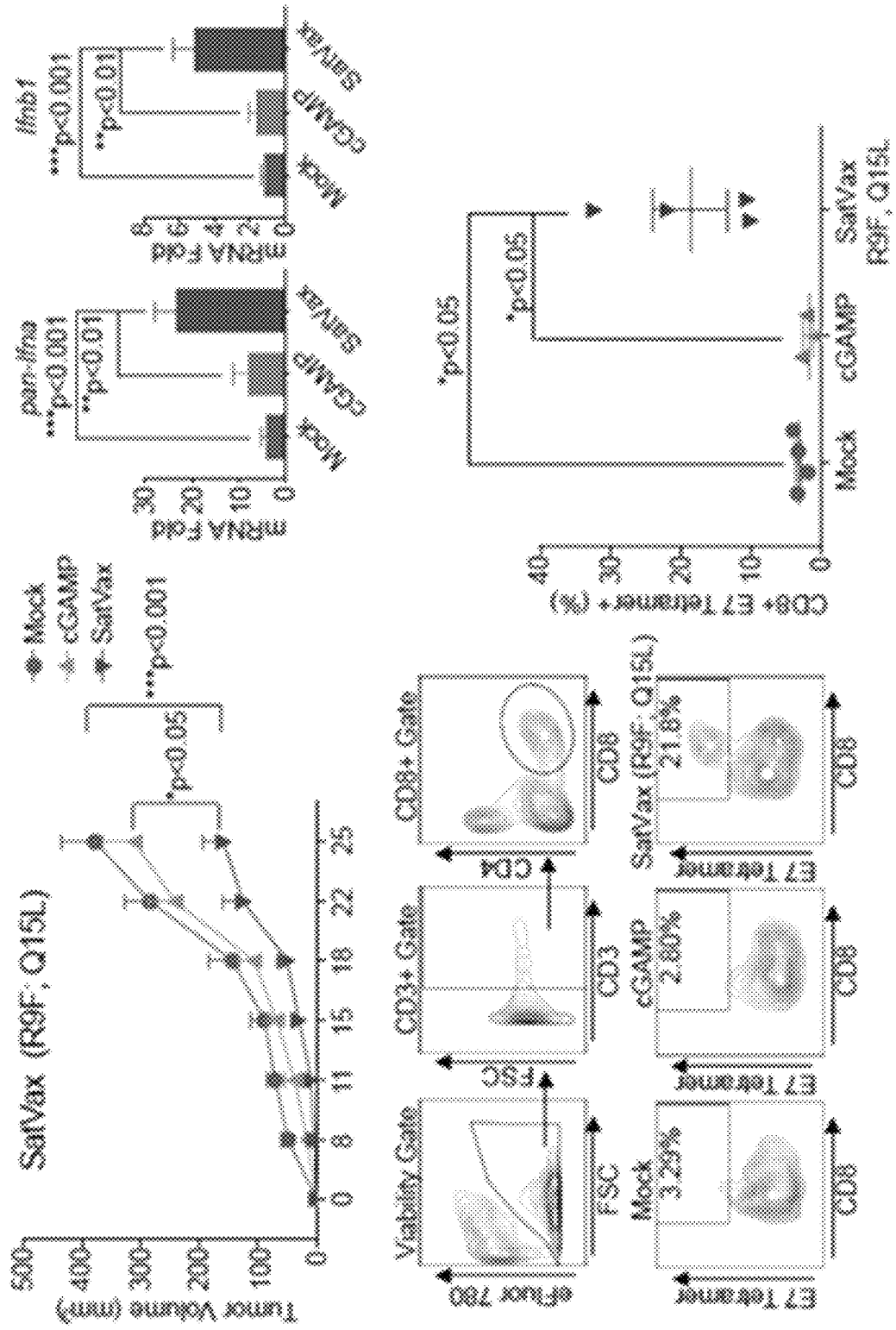

FIG. 14

```
>Ag000001_ERBB2
MELAALCRWGLLLALLPPGAASTQVCTGTDMKLRLPASPETHLDMLRHLYQGCQVVQGNLELTYLPTNAS
LSFLQDIQEVQGYVLIAHNQVRQVPLQRLRIVRGTQLFEDNYALAVLDNGDPLNNTTPVTGASPGGLREL
QLRSLTEILKGGVLIQRNPQLCYQDTILWKDIFHKNNQLALTLIDTNRSACHPCSPMCKGSRCWGESSE
DCQSLTRTVCAGGCARCKGPLPTDCCHEQCAAGCTGPKHSDCLACLHFNHSGICELHCPALVTYNTDTFE
SMPNPEGRYTFGASCVTACPYNYLSTDVGSCTLVCPLHNQEVTAEDGTQRCEKCSKPCARVCYGLGMEHL
REVRAVTSANIQEFAGCKKIFGSLAFLPESFDGDPASNTAPLQPEQLQVFETLEEITGYLYISAWPDSLP
DLSVFQNLQVIRGRILHNGAYSLTLQGLGISWLGLRSLRELGSGLALIHHNTHLCFVHTVPWDQLFRNPH
QALLHTANRPEDECVGEGLACHQLCARGHCWGPGPTQCVNCSQFLRGQECVEECRVLQGLPREYVNARHC
LPCHPECQPQNGSVTCFGPEADQCVACAHYKDPPFCVARCPSGVKPDLSYMPIWKFPDEEGACQPCPINC
THSCVDLDDKGCPAEQRASPLTSIISAVVGILLVVVLGVVFGILIKRRQKIRKYTMRRLLQETELVEPL
TPSGAMPNQAQMRILKETELRKVKVLGSGAFGTVYKGIWIPDGENVKIPVAIKVLRENTSPKANKEILDE
AYVMAGVGSPYVSRLLGICLTSTVQLVTQLMPYGCLLDHVRENRGRLGSQDLLNWCMQIAKGMSYLEDVR
LVHRDLAARNVLVKSPNHVKITDFGLARLLDIDETEYHADGGKVPIKWMALESILRRRFTHQSDVWSYGV
TVWELMTFGAKPYDGIPAREIPDLLEKGERLPQPPICTIDVYMIMVKCWMIDSECRPRFRELVSEFSRMA
RDPQRFVVIQNEDLGPASPLDSTFYRSLLEDDDMGDLVDAEEYLVPQQGFFCPDPAPGAGGMVHHRHRSS
STRSGGGDLTLGLEPSEEEAPRSPLAPSEGAGSDVFDGDLGMGAAKGLQSLPTHDPSPLQRYSEDPTVPL
PSETDGYVAPLTCSPQPEYVNQPDVRPQPPSPREGPLPAARPAGATLERPKTLSPGKNGVVKDVFAFGGA
VENPEYLTPQGGAAPQPHPPPAFSPAFDNLYWDQDPPERGAPPSTFKGTPTAENPEYLGLDVPV
```

COMPLEXES FOR DELIVERY OF ANTIGENIC PEPTIDES

The present application is a § 371 U.S. National Entry Application of PCT/US2018/035623, filed Jun. 1, 2018, which claims priority to U.S. Provisional application 62/515,234 filed Jun. 5, 2017, each of which is herein incorporated by reference in its entirety.

STATEMENT REGARDING FEDERAL FUNDING

This invention was made with government support under DE024173 awarded by the National Institutes of Health. The government has certain rights in the invention.

FIELD OF THE INVENTION

The present invention provides methods, compositions, systems, and kits comprising nano-satellite complexes and/or serum albumin carrier complexes, which are used for modulating antigen-specific immune response (e.g., enhancing anti-tumor immunity). In certain embodiments, the nano-satellite complexes comprise: a) a core nanoparticle complex comprising a biocompatible coating surrounding a nanoparticle core; b) at least one satellite particle attached to, or absorbed to, the biocompatible coating; and c) an antigenic component conjugated to, or absorbed to, the at least one satellite particle component. In certain embodiments, the complexes further comprise: d) an type I interferon agonist agent. In some embodiments, the serum albumin complexes comprise: a) at least part of a serum albumin protein, b) an antigenic component conjugated to the carrier protein, and c) a type I interferon agonist agent.

BACKGROUND

Utilizing monoclonal antibodies (mAbs) to block the inhibitory "checkpoint" receptors signaling informs a major direction in cancer immunotherapy research. This approach delivers clinical promise by partially restoring the effector function of often "exhausted" tumor infiltrating lymphocytes (TILs) (Nguyen and Ohashi, 2015). However, a major limitation of this strategy is that an exclusive effector-cell-targeted approach is prone to failure in tumors that are less immunogenic. These hypo-immunogenic "cold" tumors are more resistant to effector immune cells, and often fail to elicit the production of tumor antigen (TA)-specific cytotoxic T lymphocytes (CTLs). Notably, the incidence of human papillomavirus (HPV)-positive head and neck squamous cell carcinoma (HNSCC) has increased over 4 times in the past several decades (Marur et al., 2010). Pilot clinical trials suggest the clinical response rates of HNSCC to checkpoint blockade are generally lower than 20% regardless of HPV status (Herbst et al., 2014; Starr, 2015; Ferris et al., 2016). Thus, identification of novel mechanisms underpinning hypoimmunogenicity and attenuating cancer-associated immune suppression are among the most pressing tasks in the realm of tumor immunology (Schreiber et al., 2011).

SUMMARY OF THE INVENTION

The present invention provides methods, compositions, systems, and kits comprising nano-satellite complexes and/or serum albumin carrier complexes, which are used for modulating antigen-specific immune response (e.g., enhancing anti-tumor immunity). In certain embodiments, the nano-satellite complexes comprise: a) a core nanoparticle complex comprising a biocompatible coating surrounding a nanoparticle core; b) at least one satellite particle attached to, or absorbed to, the biocompatible coating; and c) an antigenic component conjugated to, or absorbed to, the at least one satellite particle component. In certain embodiments, the complexes further comprise: d) an type I interferon agonist agent. In some embodiments, the serum albumin complexes comprise: a) at least part of a serum albumin protein, b) an antigenic component conjugated to the carrier protein, and c) a type I interferon agonist agent.

In some embodiments, provided herein are compositions, systems, and kits comprising: a nano-satellite complex, wherein the nano-satellite complex comprises: a) a core nanoparticle complex comprising a biocompatible coating surrounding a nanoparticle core; b) at least one satellite particle attached to, or absorbed to, the biocompatible coating; and c) an antigenic component conjugated to, or absorbed to, the at least one satellite particle component, wherein the antigenic component comprises an antigenic peptide (e.g., as shown in step 2 of FIG. 10). In certain embodiments, the complexes further comprise d) an type I interferon agonist agent (e.g., as shown in step 3 of FIG. 10). In some embodiments, the type I interferon agonist agent (e.g., which locally increases the expression of type I interferon) is electrostatically attracted to, or absorbed to, i) the antigenic component, ii) the at least one satellite particle, and/or iii) the core nanoparticle complex.

In certain embodiments, provided herein are methods of eliciting an immune response in a subject comprising: administering to a subject a composition comprising a nano-satellite complex, wherein the nano-satellite complex comprises: i) a core nanoparticle complex comprising a biocompatible coating surrounding a nanoparticle core; ii) at least one satellite particle attached to, or absorbed to, the biocompatible coating; and iii) an antigenic component conjugated to, or absorbed to, the at least one satellite particle component, wherein the antigenic component comprises an antigenic peptide.

In certain embodiments, provided herein are methods of treating cancer (or other disease), and/or modulating antigen-specific immune response, in a subject comprising: administering to a subject a composition comprising a nano-satellite complex, wherein the subject comprises a plurality of cancer cells (or other disease cells), wherein the nano-satellite complex comprises: i) a core nanoparticle complex comprising a biocompatible coating surrounding a nanoparticle core; ii) at least one satellite particle attached to, or absorbed to, the biocompatible coating; iii) an antigenic component conjugated to, or absorbed to, the at least one satellite particle component, wherein the antigenic component comprises an antigenic (e.g., peptides that are derived from one or multiple antigens); and iv) an type I interferon agonist agent.

In further embodiments, the antigenic peptide comprises at least one neoantigenic determinant, including, for example, an oncogenic viral antigenic determinant. In some embodiments, the antigenic peptides comprise at least one epitope from a tumor antigen, including a viral oncoprotein. In certain embodiments, the antigenic peptide comprises a least one epitope from an infectious virus, at least one epitope from a parasite, and/or at least one epitope from an infectious bacteria. Suitable antigens from viruses, parasites, and bacteria for immunizing subject (e.g., human subjects) are well known in the art (see, e.g., Tables 5 and 6). Additional antigens are in development for vaccines including, for example: Adenovirus vaccine, Coxsackie B virus vaccine, Cytomegalovirus vaccine, Dengue vaccine, Eastern Equine encephalitis virus vaccine, Ebola vaccine, Enterovirus 71 vaccine, Epstein-Barr vaccine, Hepatitis C vaccine, HIV vaccine, HTLV-1 T-lymphotropic leukemia vaccine, Marburg virus disease vaccine; Norovirus vaccine; Respiratory syncytial virus vaccine; Severe acute respiratory syndrome (SARS) vaccine; West Nile virus vaccine; Zika fever; Caries vaccine; Ehrlichiosis vaccine; Leprosy vaccine; Lyme disease vaccine; *Staphylococcus aureus* vaccine; *Streptococcus pyogenes* vaccine; Syphilis vaccine; Tularemia vaccine; *Yersinia pestis* vaccine; Malaria vaccine; Schistosomiasis vaccine; Chagas disease vaccine; Hookworm vaccine; Onchocerciasis river blindness vaccine for humans; Trypanosomiasis vaccine; and Visceral leishmaniasis vaccine.

In further embodiments, the kits, compositions, and systems can be combined with an immune checkpoint inhibitor agent to further enhance anti-tumor immunity. In further embodiments, the systems, kits, and compositions further comprise cancer cells and/or antigen presenting cells.

In certain embodiments, the administering kills at least some of the plurality of cancer cells and/or modulates antigen-specific immune response. In further embodiments, the cancer cells are from a type of cancer selected from the group consisting of: head and neck squamous-cell carcinoma (HNSCC), HPV-positive cancer, odontogenic tumors, bladder cancer, breast cancer, cervical cancer, colorectal cancer, leukemia, melanoma, non small lung cell cancer (NSCLC), ovarian cancer, pancreatic cancer, and prostate cancer. In additional embodiments, the cancer cells are part of a tumor in the subject. In further embodiments, the tumor is a hypo-immunogenic "cold" tumor, which is characterized by insufficient elicitation of tumor-specific immunity and resistance to immunogenic cytotoxicity.

In other embodiments, provided herein are compositions, systems, and kits, comprising: a serum albumin carrier-adjuvant-antigen complex (SA complex), wherein the SA complex comprises: a) a carrier protein comprising at least part of a serum albumin protein (e.g., at least part of human serum albumin or bovine albumin, or other mammalian serum albumin; or albumin nanoparticle formulation); and b) an antigenic component conjugated to the carrier protein, wherein the antigenic component comprises an antigenic peptide (e.g., peptides that are derived from one or multiple antigens). In some embodiments, the SA complex further comprises: c) an type I interferon agonist agent. In other embodiments, albumin can be made in nanoparticles form (10-500 nM) to encapsulate with modified antigen and adjuvants.

In further embodiments, provided herein are methods of treating cancer (or other disease), and/or modulating antigen-specific immune response, in a subject comprising: administering to a subject a composition comprising a carrier-antigen-adjuvant complex, wherein the subject comprises a plurality of cancer cells (or other disease cells), wherein the carrier-antigen complex comprises: i) a carrier protein comprising at least part of a serum albumin protein or albumin nanoparticle; and ii) an antigenic component conjugated to the carrier protein, wherein the antigenic component comprises an antigenic peptide. In some embodiments, the complexes further comprise: iii) a type I interferon agonist agent. The serum albumin carrier-antigen-adjuvant complex, in certain embodiments, can be combined with an immune checkpoint blockade agent to further enhance anti-tumor immunity (e.g., the immune checkpoint blockade agent can be administered, right before, with, or after administration of the SA complex).

In certain embodiments, the type I interferon agonist agent comprises activators of a type I interferon signaling adaptor protein, stimulator of interferon genes (STING), which include cyclic dinucleotides selected from c-di-GMP, c-di-AMP, and cGAMP, or its analogs. In other embodiments, the STING agonist agent is selected from the group consisting of: c-di-IMP, c-di-UMP, and 5,6-dimethylxanthenone-4-acetic acid (DMXAA), 2'3'-cGAM(PS)$_2$ (Rp/Sp), and 2'3'-c-di-AM(PS)$_2$ (Rp,Rp). In other embodiments, the type I interferon agonist agent comprises a Toll-like Receptor (TLR) family protein agonist, such as TLR9 agonist CpG. In particular embodiments, the kits, compositions, and systems further comprise a physiologically compatible aqueous solution and/or cancer cell lysates.

In certain embodiments, the subject is a human or other mammal. In some embodiments, the methods comprise combining the aforementioned nanosatellite complex or the serum albumin carrier-antigen-adjuvant complex with the administration of an immune checkpoint inhibitor agent to the subject. These immune checkpoint inhibitors may include monoclonal antibodies, such as anti-PD-L1, anti-CLTA-4, or anti-PD-1. In further embodiments, the immune check-point inhibitor agent is selected from: YERVOY (ipilimumab), KEYTRUDA (pembrolizumab), OPDIVO (nivolumab), and TECENTRIQ (atezolizumab).

In certain embodiments, the nanosatellite particles can be also used as a photothermal agent, in addition to its function as a delivery vehicle for type I interferon agonists and antigens. In some embodiments, the core comprises a material selected from: near-infrared photothermal agent material and MRI contrast agent material, and the at least one satellite particle comprises near-infrared photothermal agent material, MRI contrast agent material, and near-infrared optical dye material. In additional embodiments, the nanoparticle core comprises a material that is selected from the group consisting of: $Fe_3O_4$, silicon, gold, copper, and carbon. In some embodiments, the at least one satellite particle comprises a material is selected from the group consisting of: gold sulfide ($Au_2S$), copper sulfide ($Cu_2S$), carbon nanotubes, and graphene. In certain embodiments, there is no shell surrounding the core, but instead, there are the one or more satellite particles are clearly visible as discrete particles (e.g., as view by a tunneling electron microscope).

In embodiments, the nanoparticle core comprises $Fe_3O_4$, and/or biocompatible coating comprises polysiloxane, and/or the at least one satellite particle comprises a plurality of satellite particles composed of gold. In certain embodiments, the core particle has a diameter of 15-20 nm. In other embodiments, the satellite particles have an average diameter of 2-4 nm. In particular embodiments, the core particle is spherical or cubical in shape.

In further embodiments, the core nanoparticle comprises a first type of material is selected from the group consisting of: $Fe_3O_4$, silicon, gold, copper, and carbon. In particular embodiments, the first type of material comprises $Fe_3O_4$. In additional embodiments, the $Fe_3O_4$ is highly crystallized and has an X-ray diffraction (XRD) pattern where the brightest diffraction ring is from the 440 plane. In further embodiments, the $Fe_3O_4$ has a preferred lattice orientation along the 400 and 440 XRD diffraction planes. In other embodiments, the nanosatellite particle comprise a second type of material that is selected from the group consisting of: gold, gold sulfide ($Au_2S$), copper, copper sulfide (CuS), carbon, carbon nanotubes, and graphene. In certain embodiments, the second type of material comprises gold sulfide ($Au_2S$). In other embodiments, the near-infrared optical dye material is selected from the group consisting of: IR820, ICG, and 5, aminolevulinic acid (5-ALA). The present invention is not limited by the shape of the core or the satellite particle. Examples of shapes include, but are not limited to, spherical, cubic, rod shaped, disc shaped, etc.

In some embodiments, the at least one satellite particle has a size between 0.5 nm and 50 nm in diameter (e.g., 0.5 ... 1.5 ... 10 ... 23 ... 32 ... 46 ... and 50 nm). In further embodiments, the at least one satellite component is smaller than (or the same size as) the core nanoparticle complex. In other embodiments, the at least one satellite component is larger than the core nanoparticle complex. In further embodiments, the at least one satellite component has a size between 2 nm and 7 nm in diameter (e.g., about 5 nm or about 2-4 nm). In further embodiments, the nanoparticle core has a size between 4 and 60 nm in diameter. In additional embodiments, the nanoparticle core has a size between 10 and 20 nm in diameter. In further embodiments, the nano-satellite complex are present in the composition at a concentration of between 1.0 and 5.0 mg/mL (e.g., 1.0 ... 3.3 ... and 5.0 mg/ml). In other embodiments, the biocompatible coating comprises a material selected from the group consisting of: human serum albumin (HSA), polyethylene glycol, triblock copolymer, PEO-b-PPO-b-PEO (F121), PEO-b-PVP, glucosylated poly(pentafluorostyrene), chitosan, silica, and gum Arabic, gluconic acid, lactobionic acid, polyacrylic acid, apatite, and Casein. In additional embodiments, the biocompatible coating is functionalized with thiol groups or amine groups. In particular, one can use siloxane molecules like (3-Mercaptopropyl) trimethoxysilane (MPTMS) to produce thiol groups or (3-Aminopropyl)triethoxysilane to produce amine groups on nanoparticle surfaces to functionalize polymer coated nanoparticles.

In some embodiments, the administering generates a plurality of core-satellite nanocomposite-impregnated cancer cells in the subject. In further embodiments, the methods comprise: subjecting the subject to photothermal therapy and/or imaging, wherein the photothermal therapy: A) comprises the use of a treatment device that emits electromagnetic radiation, and B) causes at least a portion of the core-satellite nanocomposite-impregnated cancer cells to be damaged or killed; and wherein the imaging: A) comprises the use of an imaging device configured for MRI/NMR detection and/or optical detection, and B) causes at least a portion of the core-satellite nanocomposite-impregnated cancer cells to be visualized ex-vivo.

DESCRIPTION OF THE FIGURES

The patent or application file contains at least one drawing executed in color. Copies of this patent or patent application publication with color drawings will be provided by the Office upon request and payment of the necessary fee.

FIGS. 1A-K. Type I IFN signaling regulates tumor resistance to effector immune cells. (A) PCI-13 cells were co-cultured with NK cells separated from 2 healthy donors in the presence of 5 µg/ml cetuximab. NK cells were replaced weekly for a total of 12 rounds of co-incubation. Wildtype tumor cells and resistant cells were incubated with NK cells at two different T:E ratios for 16 hrs. (B) HLA-matched EGFR-specific CD8+ T-cells were incubated with wildtype or NK-resistant tumor cells at two different T:E ratios for 16 hrs. Cell death was measured by 7-AAD. Each group contains three independent biologic repeats. Comparisons were made using two-way ANOVA followed by Bonferroni post-test. (C) Gene Set Enrichment Analysis (GSEA) of the significantly differentially expressed genes (q value<0.01) between the wildtype and resistant HNSCC cells was performed. Ten of the most significantly altered pathways were shown. (D) Significantly altered genes between sensitive and resistant HNC cells were cross-referenced in the Interferome database. 358 IFN-regulated genes were significantly changed (p<0.05). (E) Heat map of representative genes expression between wildtype and resistant cells. Plotted Z-score=(expression value of each mRNA-mean value for the same mRNA across all samples)/Standard Deviation. (F-K) Real time PCR was performed to validate the top candidate genes that were altered when cancer became resistant to effector immune cells. SOX2 (FIG. 1F), NLRX1 (FIG. 1G), NLRC3 (FIG. 1H), STAT3 (FIG. 1I), STAT1 (FIG. 1J), and ISG15 (FIG. 1K).

mRNA were assessed by real time PCR. Values are expressed as mean±sem of three biologic replicates. (P-R) HEK-293T (FIG. 3L), UMSCC22b (FIG. 3Q), and UMSCC47 (FIG. 3R) cells were challenged with STING in the absence or presence of SOX2. type I interferon induction markers and STING expression levels were examined by immunoblots.

FIGS. 4A-L. Sox2 promotes tumor growth in vivo and an immune-suppressed microenvironment. (A) Five hundred empty vector control and Sox2-expressing MOC2-E6/E7 cells were plated in a 96-well plate. Cell proliferation was quantitated at the indicated time points using an alamarBlue assay. (B) Control or Sox2-expressing MOC2-E6/E7 cells were implanted subcutaneously in C57BL/6 mice. A 20-Gy IR was administered on day 14. Tumor growth was monitored at the indicated times. n=8 for each group. (C) Immunohistochemical staining of SOX2 was performed in the grafted MOC2-E6/E7 tumors (top) and primary human HNSCC specimens (bottom). (D-G) Tumors were harvested and homogenized for RNA extraction. Tc1/TH1 activation marker genes, including Cxcl9 (FIG. 4D), Cxcl10 (FIG. 4E), Mx1 (FIG. 4F), and Ifng (FIG. 4G), were quantitated by real time PCR. n=4 for each group, and real time PCR was performed in triplicates. (H) Grafted tumor sections were stained with anti-Mx1, and the IHC scores were compared among groups. (I) Tumor homogenates were subjected to SDS-PAGE, and immunoblotted against the indicated markers for type I interferon signaling activation. (J) TILs were separated using Ficoll-paque gradient, and the frequency of CD3+CD8+ population was quantitated by flow cytometry. Comparisons between two groups were made using unpaired t-test. (K-L) Primary HNSCC specimens from 218 patients were procured and made into a tissue microarray, which is then stained with anti-SOX2. The expression levels of SOX2 within the tumor cells were assessed by Aperio ImageScope, and compared among different patient groups using unpaired t-test.

Figure 4D:
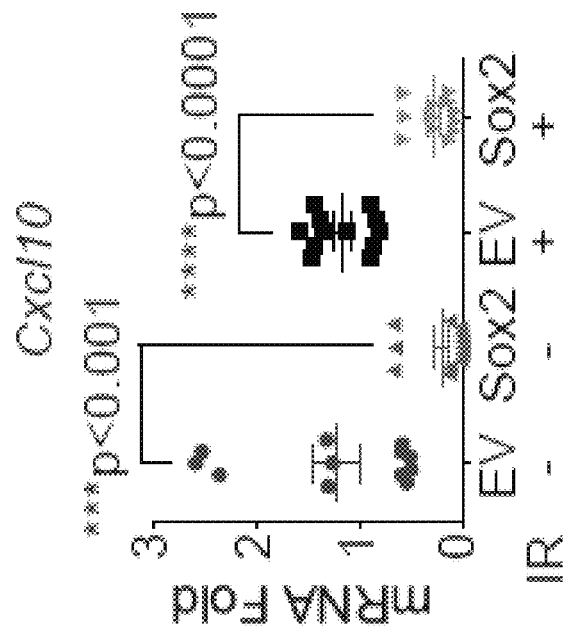
Figure 4E:
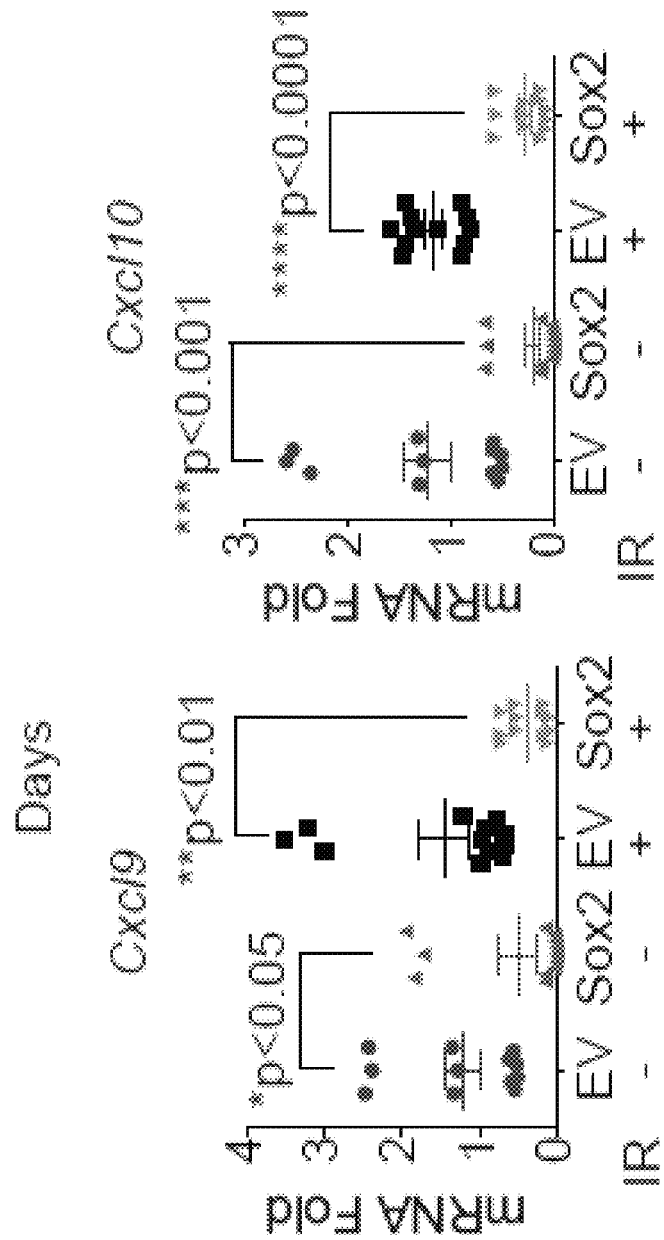
Figures 4F, 4G:
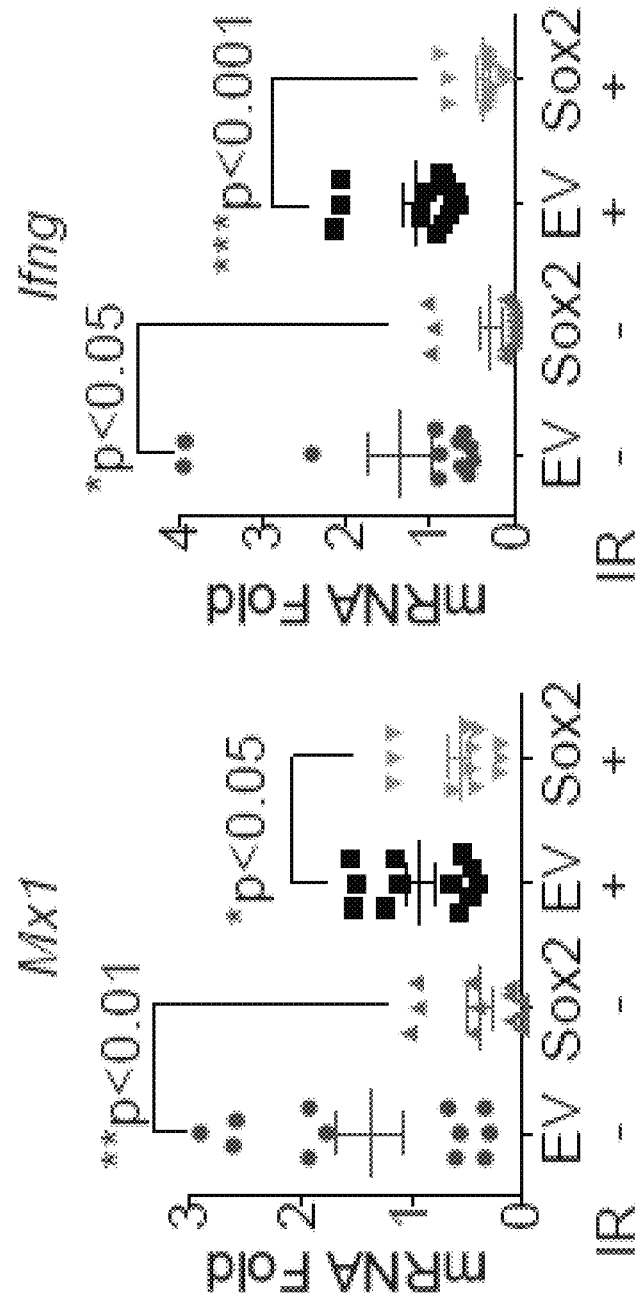
Figure 4H:
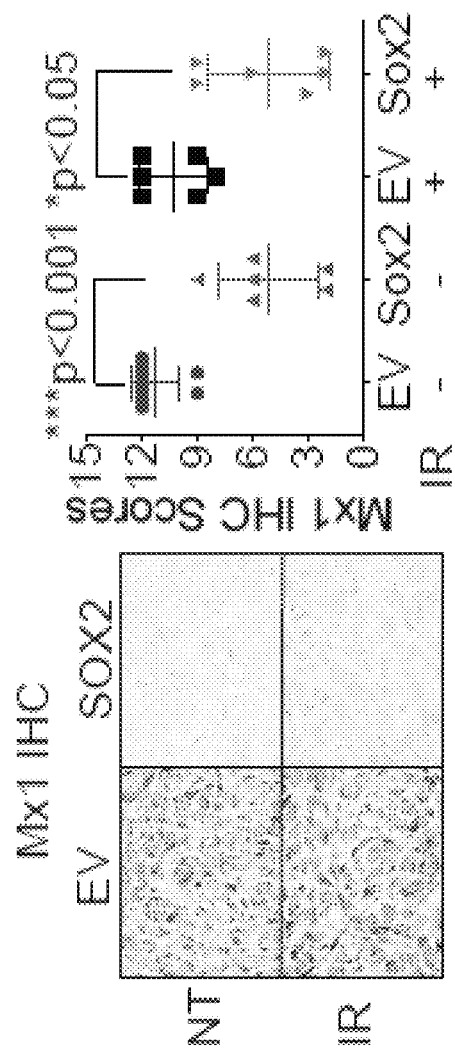
Figure 4I:
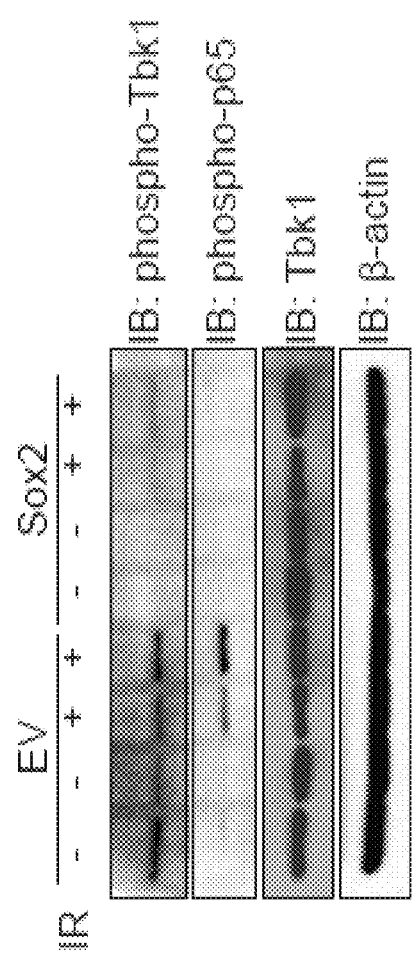
Figure 5:
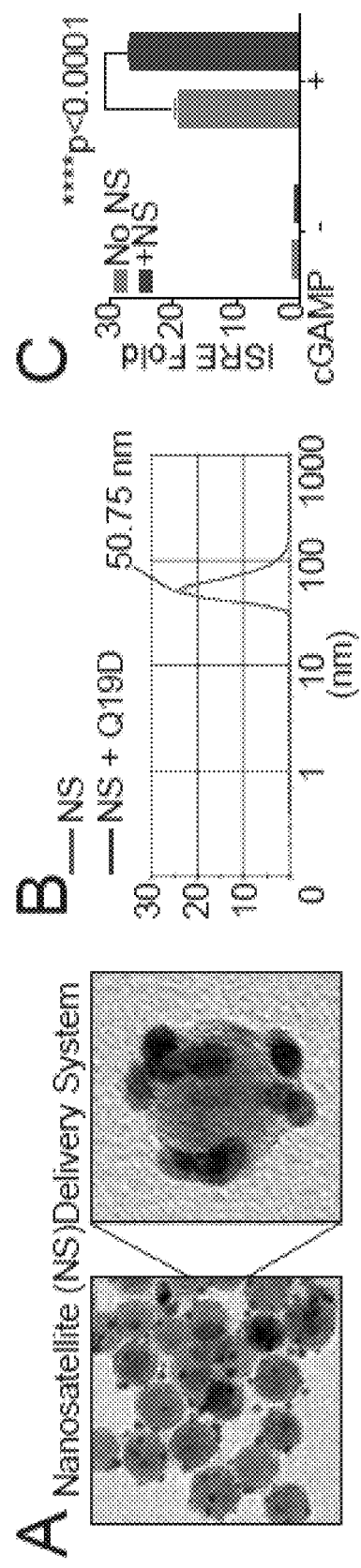
Figure 5:
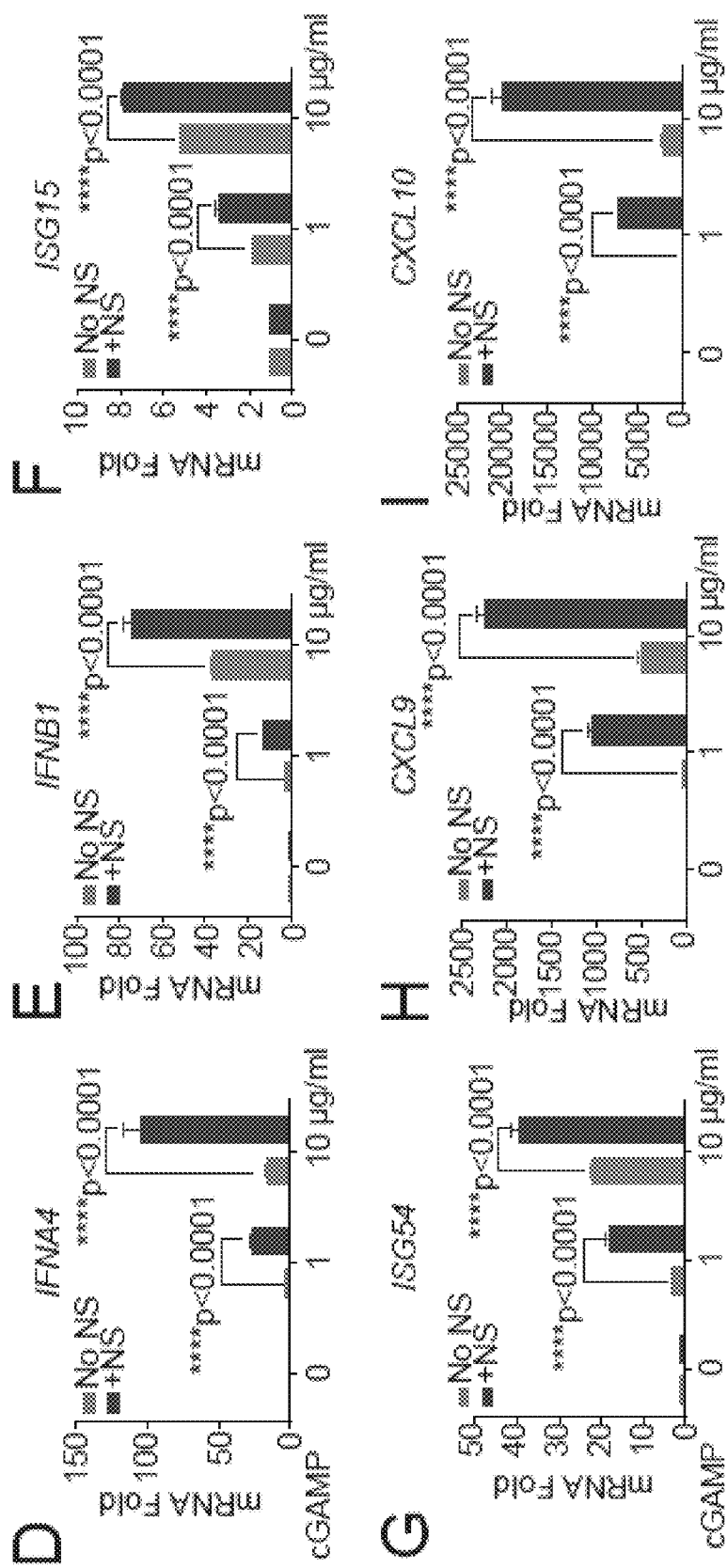
Figure 5:
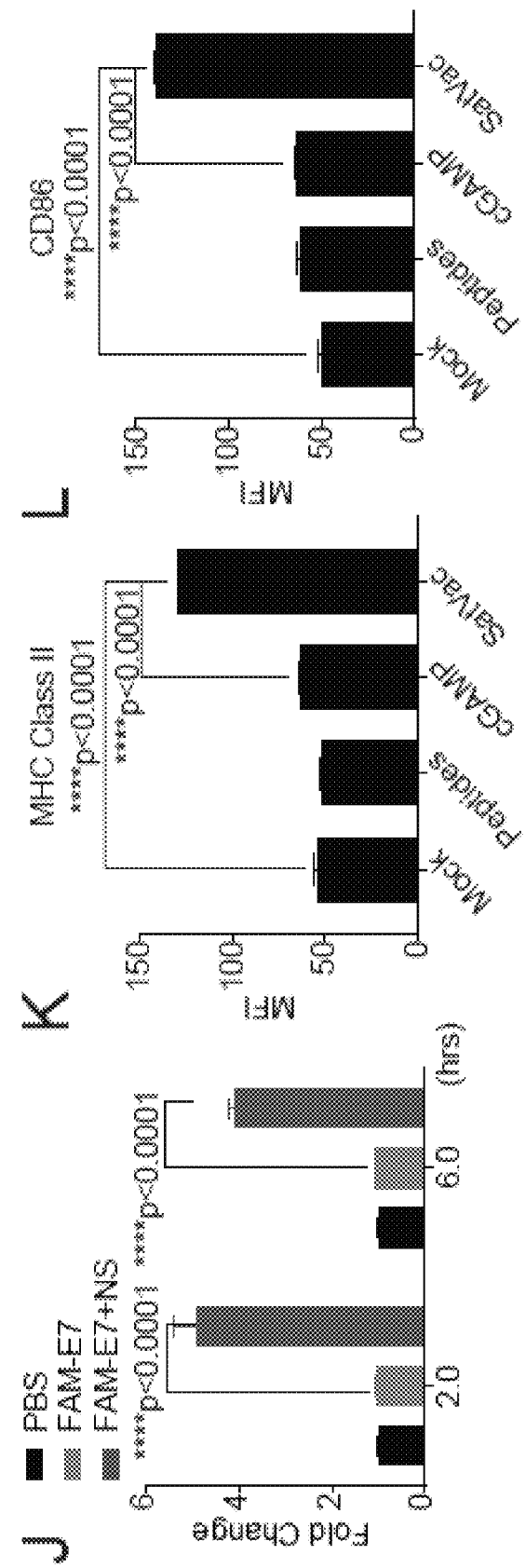

FIG. 5, Panels A-L. Nanosatellite enhances the potency of STING agonist. (A) Transmission electron microscopy imaging of an exemplary core-satellite structure. (B) Normal distribution of the nanosatellite hydrodynamic diameters prior to and after peptides conjugation. (C) THP1-Blue ISG cells, which express a secreted embryonic alkaline phosphatase (SEAP) reporter, were challenged with cGAMP in the absence or presence of the nanosatellite delivery vehicle. IRF activity was quantitated by measuring SEAP activity. (D-I) THP1 cells were treated with different doses of cGAMP with or without the nanosatellites delivery vehicle. The mRNA abundance of the indicated type I interferon signaling genes (IFNA4, FIG. 4D; IFNB1, FIG. 4E; ISG15, FIG. 4F; ISG54, FIG. 5G; CXCL9, FIG. 5H; and CXCL10, FIG. 5I) were quantitated by real time PCR. (J) Primary bone marrow-derived macrophages were incubated with FAM-labeled peptides with or without NS. The vaccine intracellular uptake was measured by FAM fluorescence intensity. (K-L) Primary bone marrow-derived dendritic cells were treated with peptides, cGAMP, or the full vaccine (SatVax). Dendritic cells maturation markers, such as MHC class II (FIG. 5K) and CD86 (FIG. 5L), were stained 24 hrs post-treatment. Median fluorescence intensity (MFI) was quantitated by flow cytometry. Error bar represents 3 biologic replicates. Data were analyzed by ANOVA, and p<0.05 was considered significant. Results of all experiments are representative of at least 2-3 repeats.

Figure 6A:
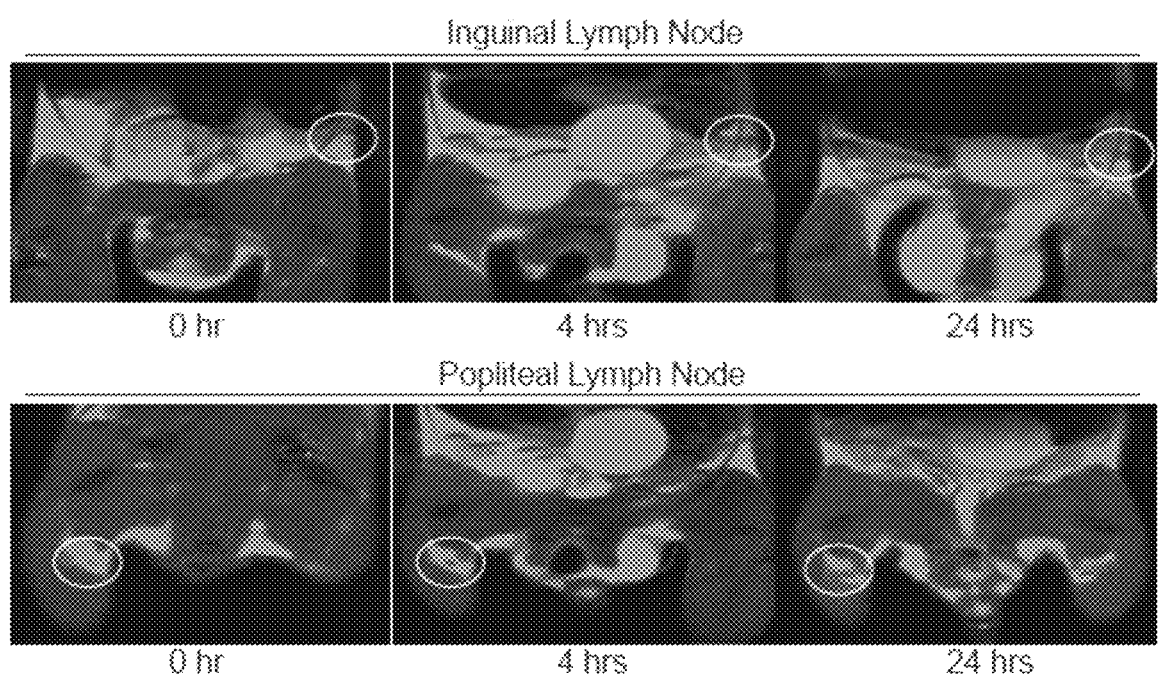

FIG. 6AD. Nanosatellite-Vaccine (SatVax) (R9F; Q15L) accumulates in the lymph nodes and promotes tumor-specific immunity. (A) MRI imaging was performed 4 hours and 24 hours post-SatVax injections, using TE=30 ms and TR=4,000 ms. The inguinal lymph node (top) and popliteal lymph node (bottom) regions were highlighted. (B) The SatVax formulation containing a core E7 epitope R9F and an E6 peptide (Q15L) was injected subcutaneously once per week for three weeks. cGAMP was administered subcutaneously as a control. Tumors were measured at the indicated time points, and the tumor volumes were calculated by ½(length×width$^2$). (C) Total RNA was extracted from tumor homogenates and assessed for the transcription of Ifna4 and Ifnb1. (D) TILs were separated from tumor homogenates and gated on CD3 and CD8 (left panel). The E7-specific T cells were quantitated by flow cytometric analysis of H-2db-restricted RAHYNIVTF-specific tetramer staining.

Figure 7:
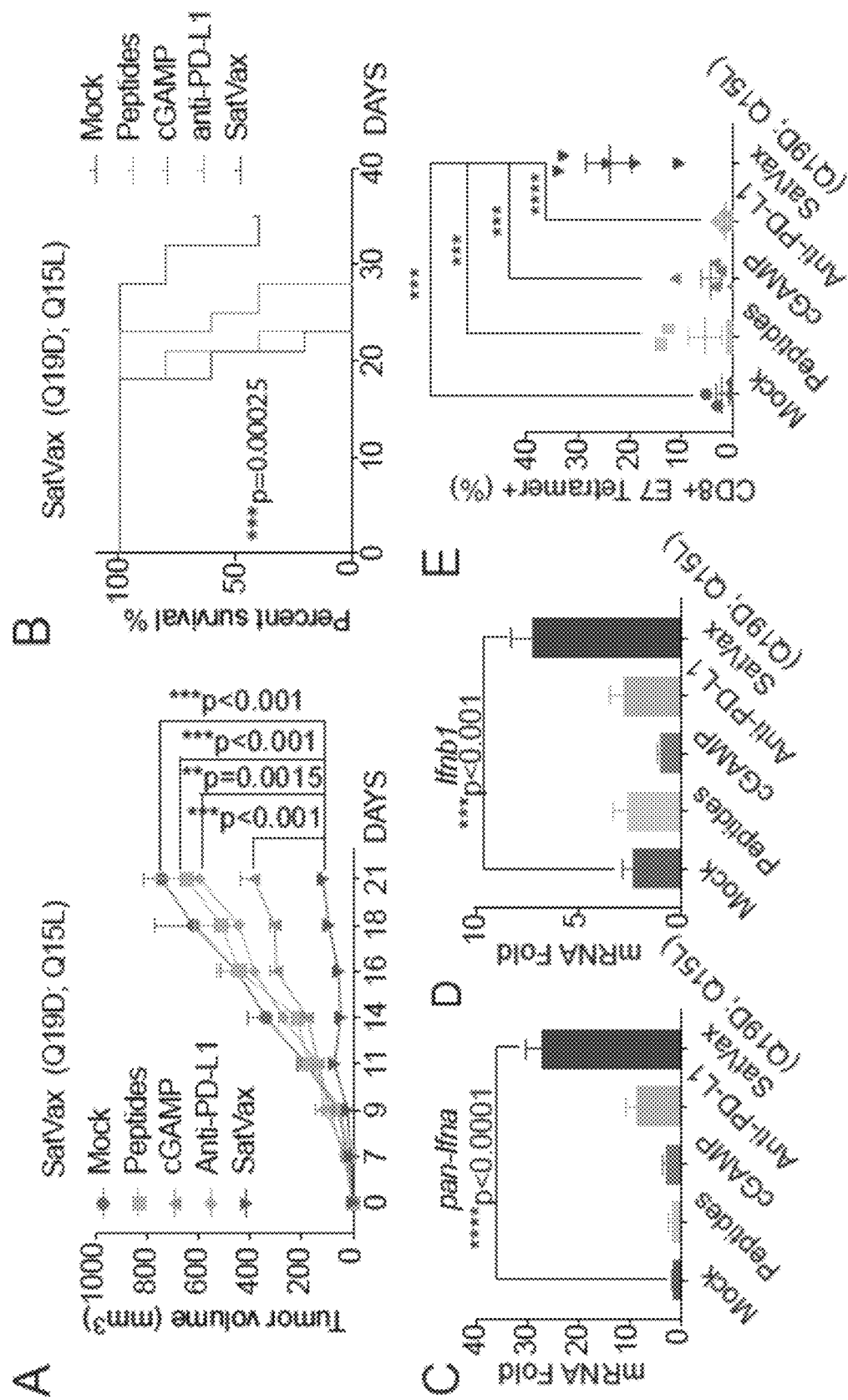
Figure 7:
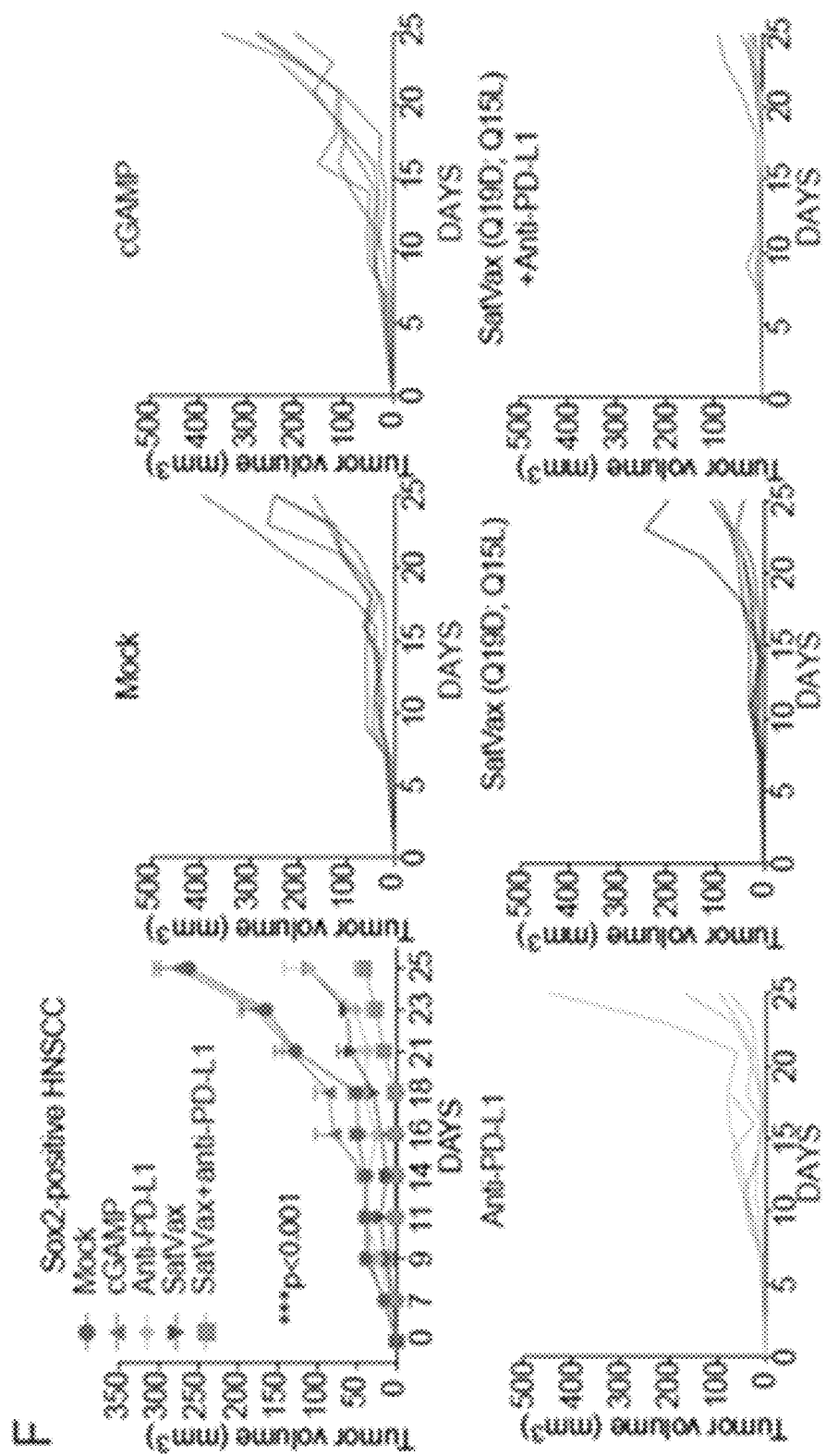

FIG. 7, Panels A-F. SatVax (Q19D; Q15L) provides significant protection against control and Sox2-expressing squamous cell carcinomas. (A) A vaccine formulation with an extended antigenic peptide, which contains flanking sequences to protect the core epitope, was subcutaneously administered once per week for three weeks after tumor implantation. The same amounts of peptides and cGAMP as in the vaccine formulation were injected as controls. Six doses of 100 μg anti-PD-L1 i.p. injections were administered as a benchmark immunotherapy agent. Tumor volumes were recorded on the indicated time points. (B) Kaplan-Meier survival curves were plotted for all groups, each of which contains 5 subjects. (C-D) RNA was extracted from the tumor homogenates of all groups. The transcription levels of Ifna4 (C) and Ifnb1 (D) were quantitated by real time PCR. (E) Tumors were minced into small pieces, and then subjected to Ficoll-Paque gradient to purify the TILs. TILs were gated on CD3 and CD8, and then analyzed for the frequency of H-2db-restricted RAHYNIVTF-specific T cells using E7-specific tetramer staining (left panel). The frequencies of E7-specific T cells were compared using one-way ANOVA followed by Tukey's multiple comparisons test. Each dot represents one mouse (right panel). Error bars represent standard error of mean.

(F) Sox2-expressing MOC2-E6/E7 cells were subcutaneously implanted on Day 0.

Figure 8:
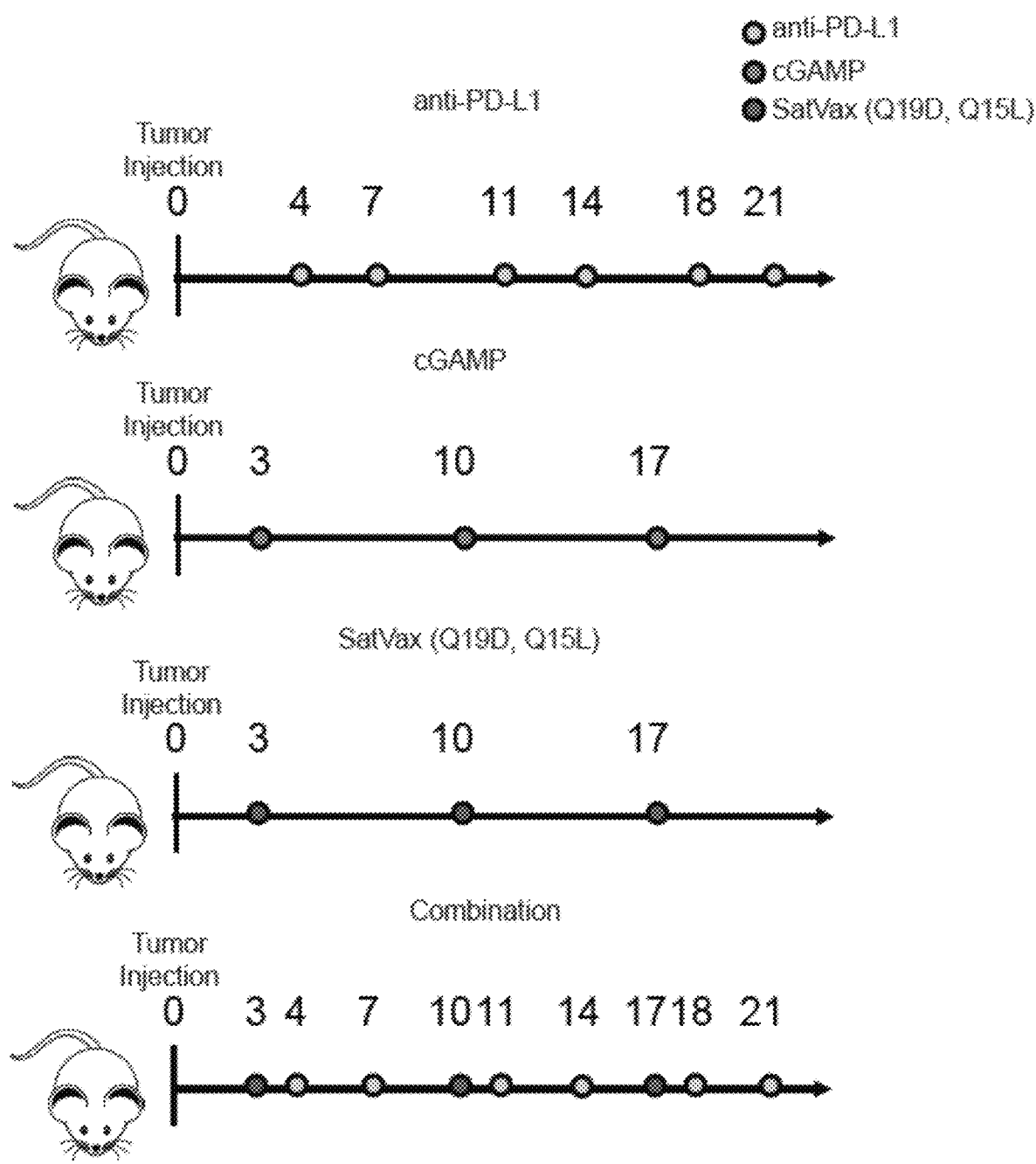

FIG. 8. Three weekly doses of cGAMP, six doses of anti-PD-L1, three weekly doses of SatVax, or a combination of SatVax with anti-PD-L1 were administered according to the schedule detailed in FIG. 8. Both summary growth curves and individual tumor growth were plotted. Error bars represent standard error of mean.

Figure 9:
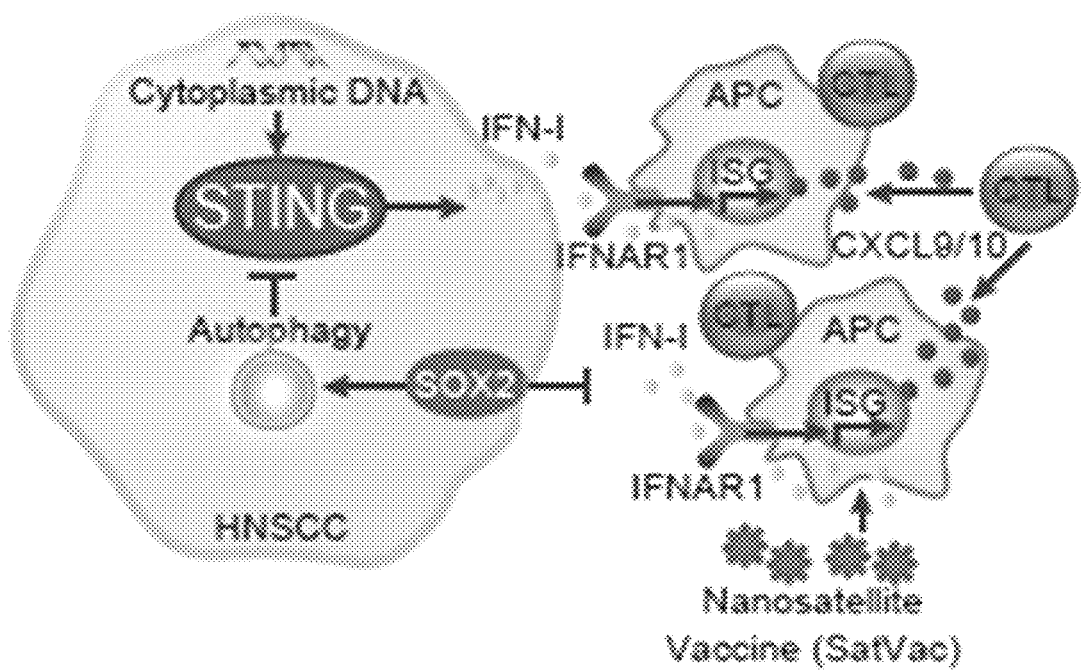

FIG. 9. Shows a hypothetical schematic of the interaction between a HNSCC cell and APC cells, various signaling factors, and the nanosatellite vaccines.

Figure 10:
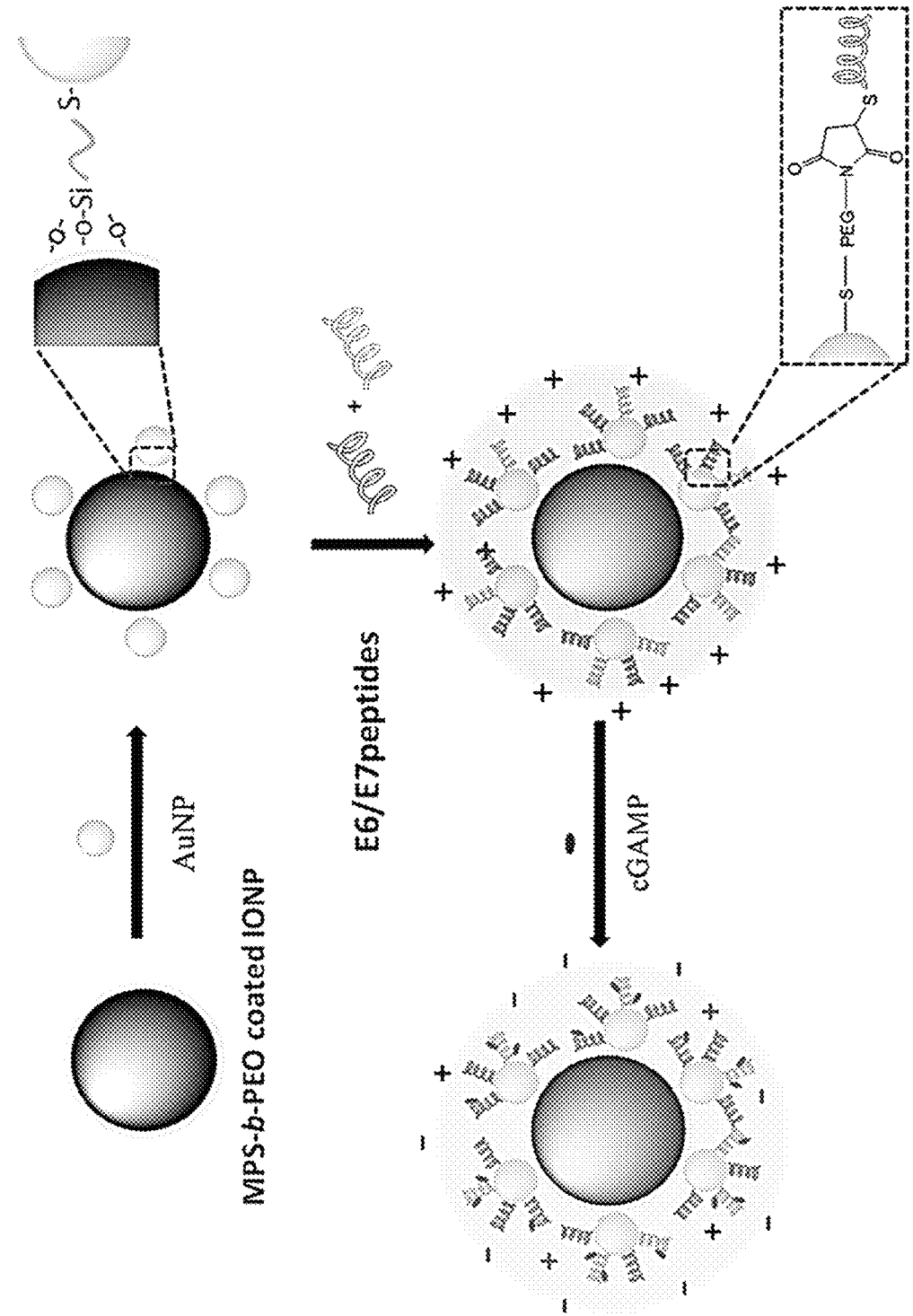

FIG. 10. Shows an exemplary method for generating a nanosatellite complex. First, a polymer coated iron-oxide nanoparticle is provided, which is mixed gold satellites such that they are conjugated as shown. Then, peptides, such as HPV E6 and E7, are conjugated to the gold nanosatellite particles. Then, a type I interferon agonist, such as cGAMP, is added which, for example, electrostatically binds to the peptides, thereby forming a nanoparticle complex.

Figure 11:
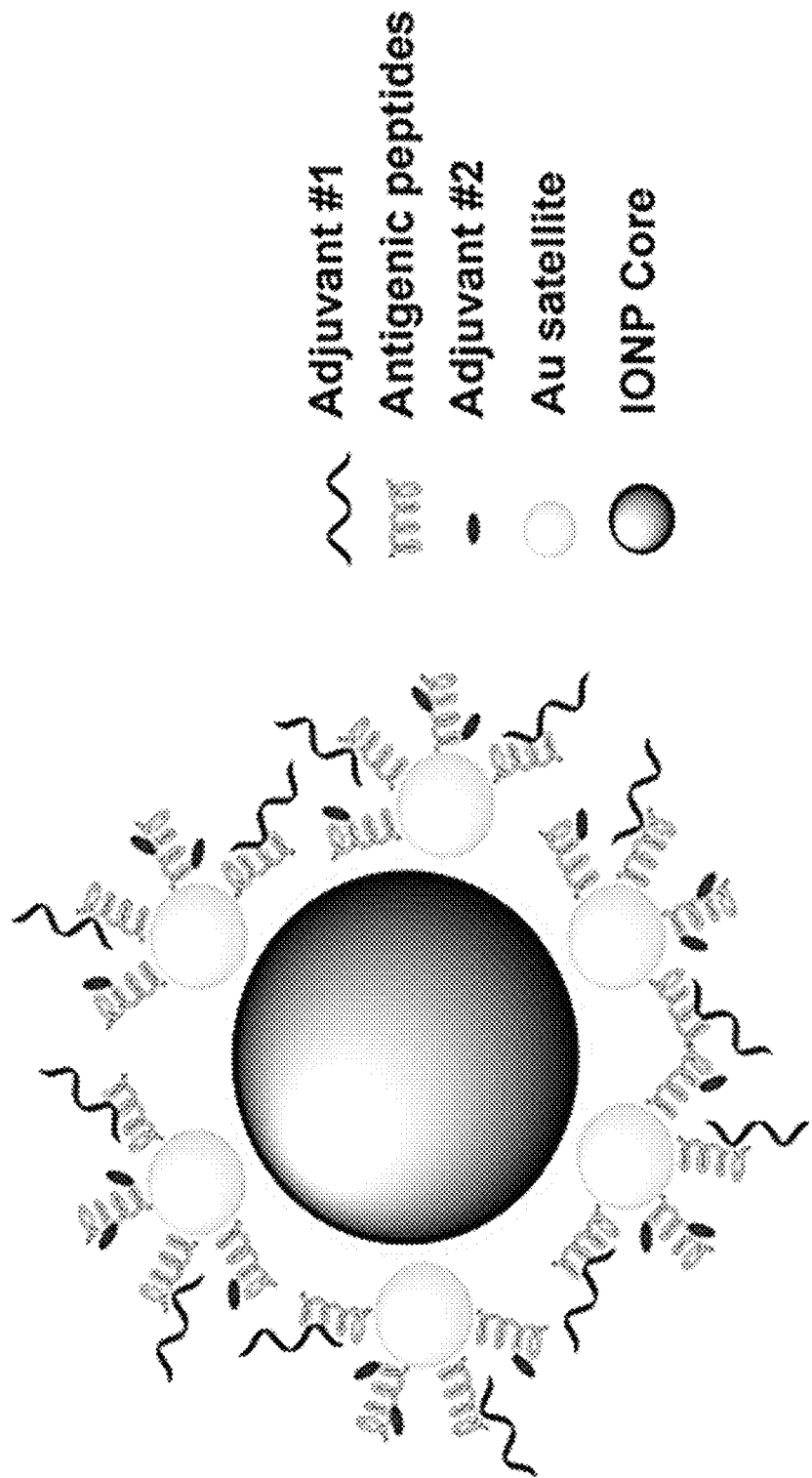

FIG. 11 shows a nanoparticle complex that employs two type I interferon agonists (adjuvant #1 and adjuvant #2).

Figure 12:
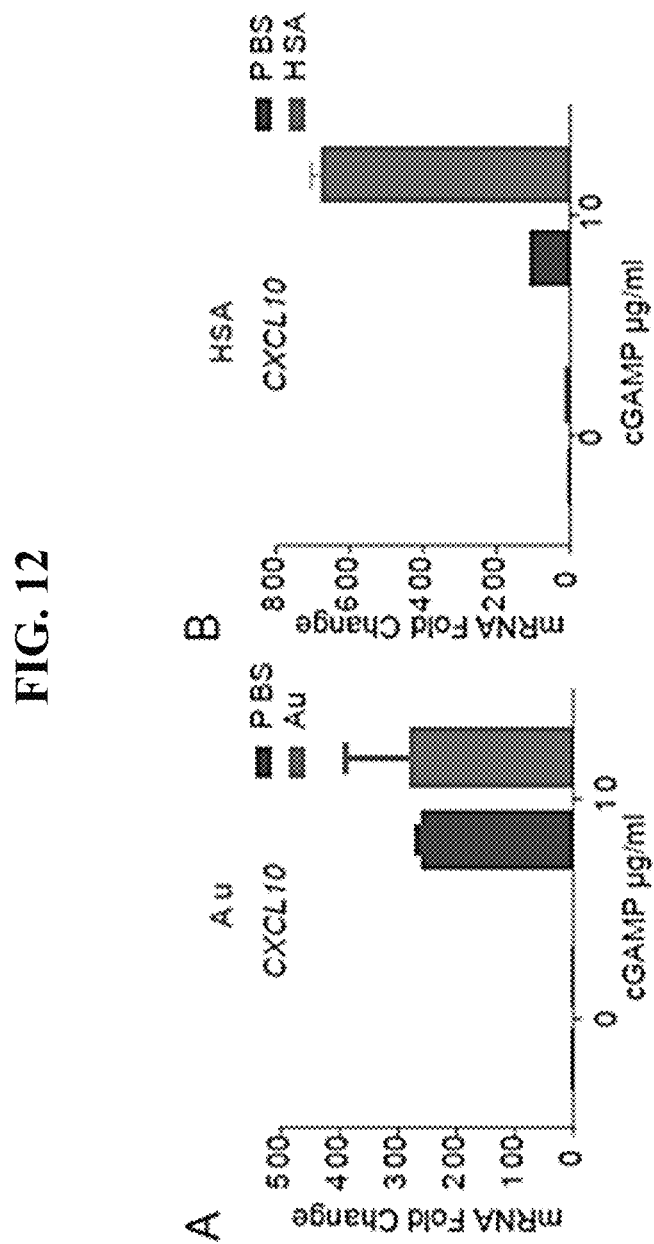

FIG. 12 shows that the HSA-peptide-cGAMP complex resulted in higher CXCL10 mRNA expression in THP1-blue ISG cells compared to control.

Figure 13:
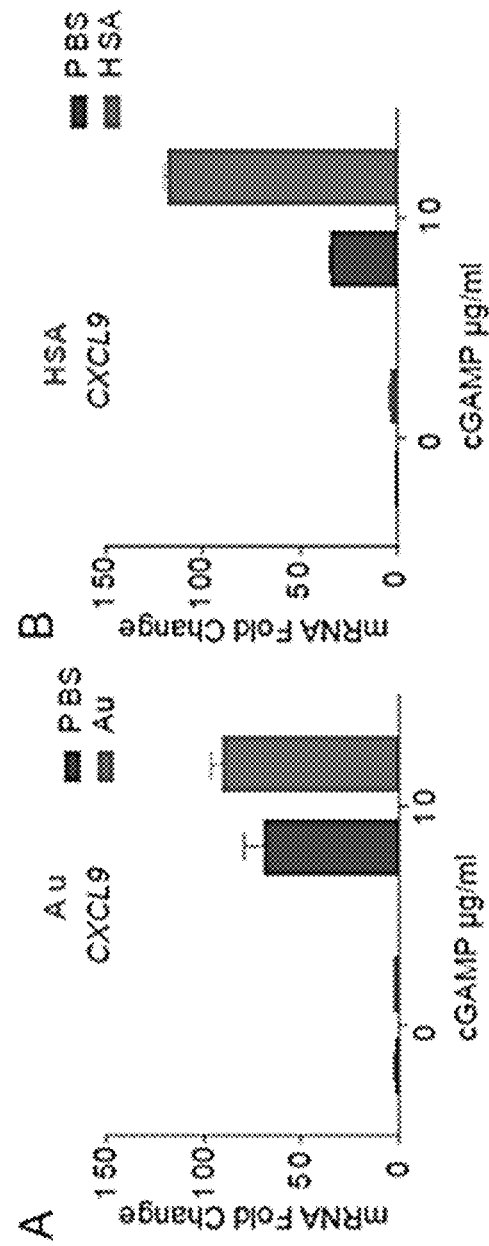

FIG. 13 shows that the HSA-peptide-cGAMP complex resulted in higher CXCL9 mRNA expression in THP1-blue ISG cells compared to control.

FIG. 14 shows the amino acid sequence of ERBB2/HER2 protein (SEQ ID NO:41), with identified T cell epitopes or HLA ligands are highlighted in gray shading, as provided by TANTIGEN, the Tumor T-cell Antigen Database.

Figure 15:
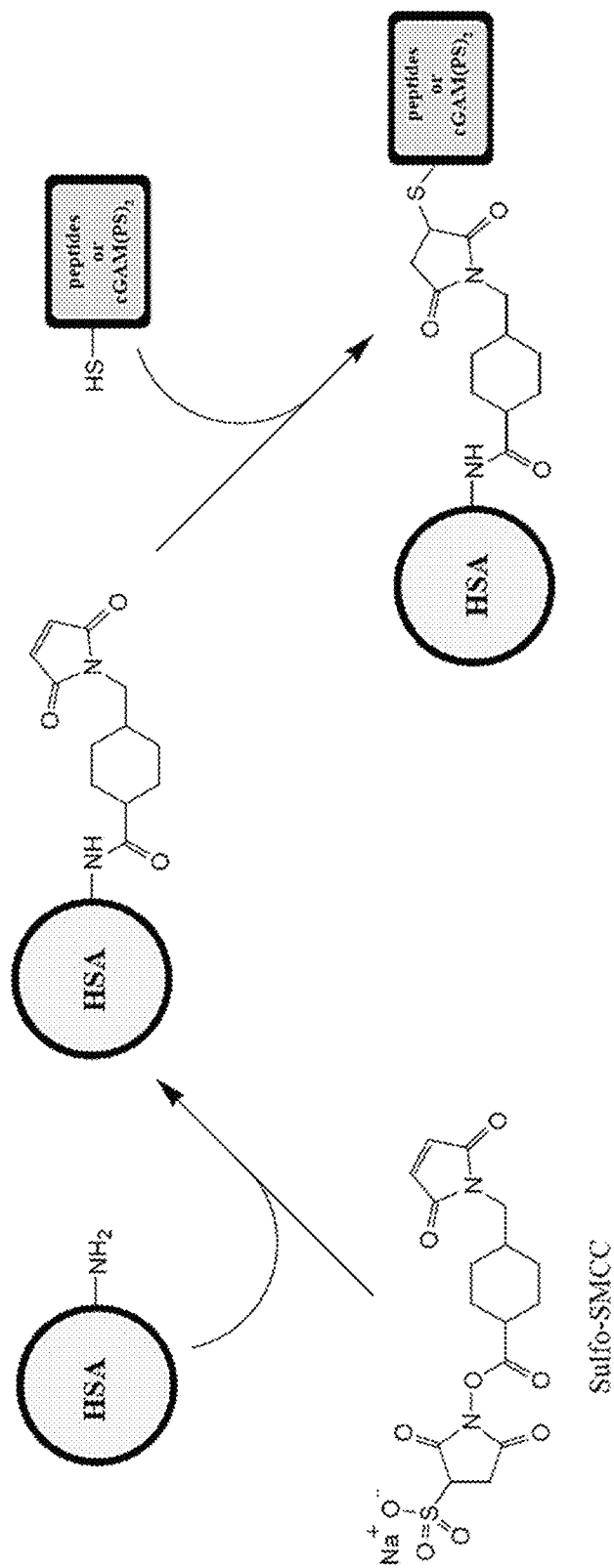

FIG. 15 shows general conjugation steps, using sulfo-SMCC as an exemplary cross-linker, for conjugating a peptide antigen and/or cGAMP to human serum albumin (HSA).

Figure 16:
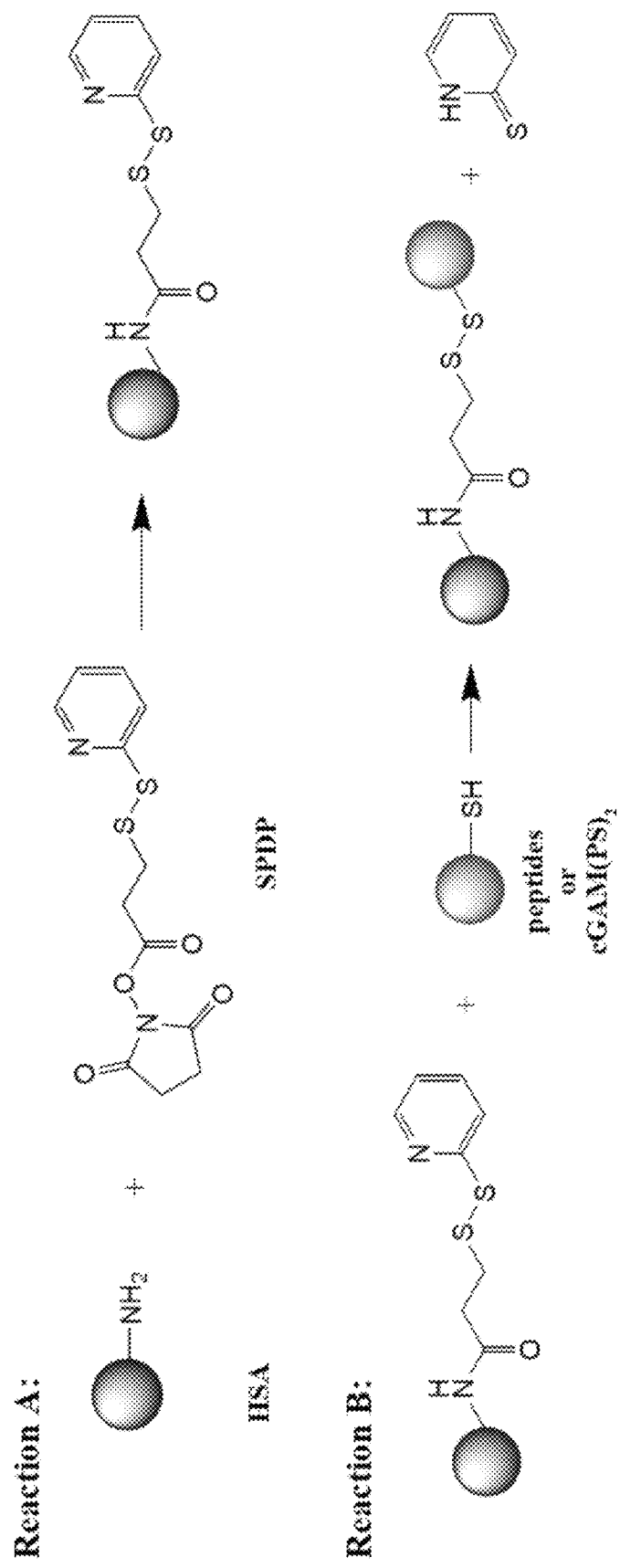

FIG. 16 shows general conjugation steps (using SPDP as an example crosslinker), to link HSA to peptides or cGAMPs.

Figure 17:
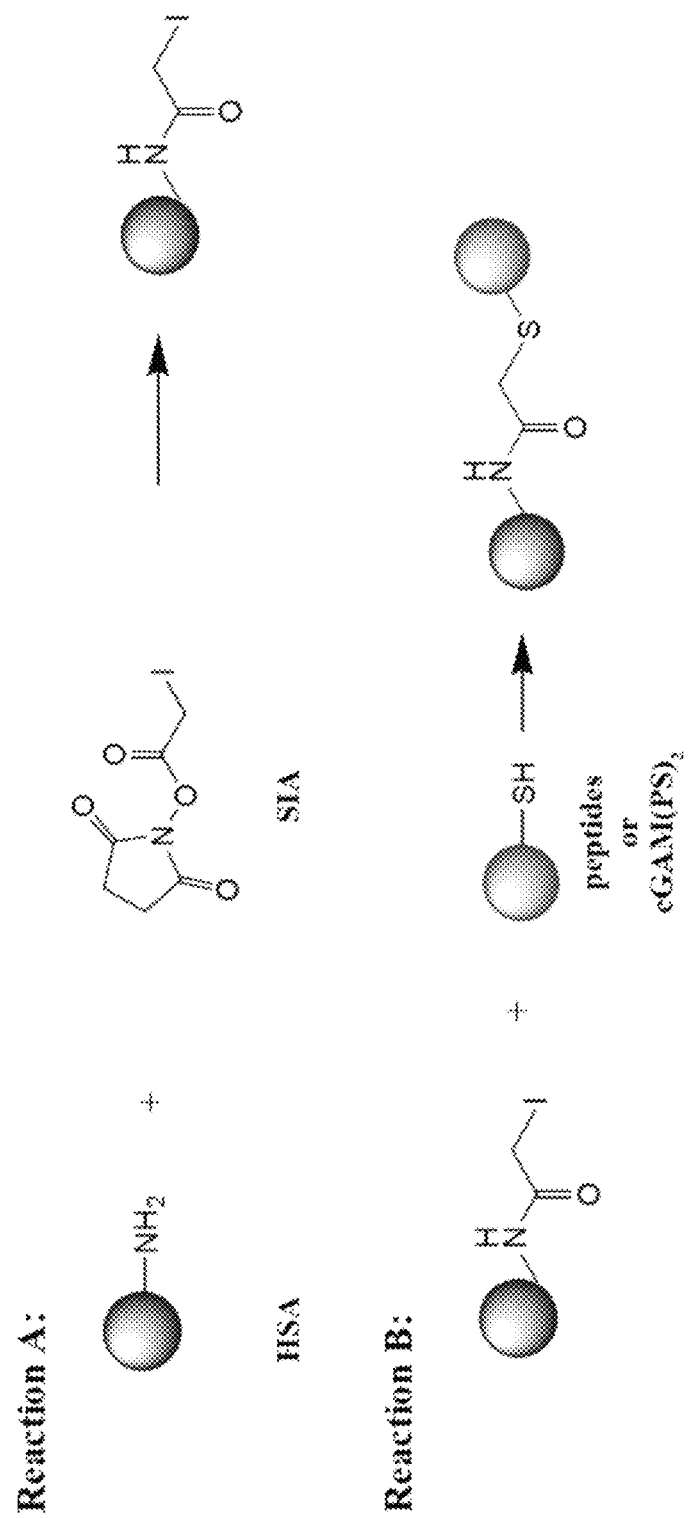

FIG. 17 shows general conjugation steps (using SIA as an example crosslinker), to link HSA to peptides or cGAMP.

DETAILED DESCRIPTION

The present invention provides methods, compositions, systems, and kits comprising nano-satellite complexes and/or serum albumin carrier complexes, which are used for modulating antigen-specific immune response (e.g., enhancing anti-tumor immunity). In certain embodiments, the nano-satellite complexes comprise: a) a core nanoparticle complex comprising a biocompatible coating surrounding a nanoparticle core; b) at least one satellite particle attached to, or absorbed to, the biocompatible coating; and c) an antigenic component conjugated to, or absorbed to, the at least one satellite particle component. In certain embodiments, the complexes further comprise: d) an type I interferon agonist agent. In some embodiments, the serum albumin complexes comprise: a) at least part of a serum albumin protein, and b) an antigenic component conjugated to the carrier protein. In further embodiments, the serum albumin complexes further comprise: c) a type I interferon agonist agent.

The response rate of Head and Neck Squamous Cell Carcinoma (HNSCC) patients to immunotherapy is below 20%. Work conducted during development of embodiments of the present disclosure identified type I interferon pathway as a central mechanism regulating HNSCC immunogenicity and resistance to immunity. A frequently amplified HNSCC oncogene, SOX2, showed a previously unknown function in dampening tumor immunogenicity by inhibiting type I interferon signaling. SOX2 expression is higher in patients with advanced stage disease and lymph node metastasis. As described in Example 1 below, a type I interferon-inducing, E6/E7-targeted nanosatellite vaccine was constructed, which promotes tumor-specific CD8+ T cells and reduces tumor burden. A combination of the vaccine with anti-PD-L1 potently suppressed Sox2-positive tumor growth.

I. Type I Interferon Induction Agents

The nano-satellite complexes and/or serum albumin carrier complexes described herein may employ a type I interferon induction agent (e.g., to increase type 1 interferon signaling in a cell, such as antigen-presenting cells and cancer cells). A "T-cell-inflamed" tumor microenvironment holds promise to better response to immune-eliciting treatments, including chemoradiotherapy and immunotherapy (Woo et al., 2015a; Woo et al., 2015b). Recent evidence suggests type I interferon signaling is indispensable to maintain an effective anti-tumor immune response (Lei et al., 2016b; Woo et al., 2015a; Zitvogel et al., 2015). The induction of type I interferon pathway is mediated by several classes of cytoplasmic pattern recognition receptors (PRR), including 5'ppp-RNA sensors RIG-I-like receptors (RLRs) and DNA sensors such as cyclic GMP-AMP synthase (cGAS) (Ahn and Barber, 2014; Barber, 2015). RLR engagement translates cytosolic 5'-ppp RNA insult into the activation of a central adaptor protein mitochondrial antiviral protein (MAVS), and subsequent nuclear translocation of NF-κB and IRF3 (Seth et al., 2005). Both transcription factors form an enhanceosome for type I interferon production. Also, DNA-bound cGAS generates a second messenger cyclic GMP-AMP (cGAMP) to activate the adaptor protein stimulator of interferon genes (STING), which promotes type I interferon induction (Ishikawa and Barber, 2008; Ishikawa et al., 2009; Sun et al., 2013; Wu et al., 2013).

The trafficking of antigen-presenting cells (APC) and effector immune cells to the tumor bed is essential for tumor antigen processing, APC maturation, cross-priming and activation of CD8+ CTL. type I interferon target genes include a number of chemokines and cytokines that are critical for the tumor-homing of APC and effectors. Indeed, a deficiency in type I interferon signaling mediated by Sting knockout results in compromised antitumor immunity and increased tumor burden (Deng et al., 2014; Woo et al., 2015b; Woo et al., 2014). Increased type I interferon signaling mediated by larger amount of nucleic-acid-rich extracellular vesicles in the tumors improves tumor immunogenicity and adaptive immune response (Moroishi et al., 2016).

Despite the significance of type I interferon signaling in host immune detection of cancer, this pathway is often suppressed in the tumor microenvironment, which constitutes a poorly understood yet significant mechanism underpinning hypoimmunogenicity (Corrales et al., 2016). Suppression of STING expression is a prominent feature of the majority of colorectal cancer cell lines (Xia et al., 2016). HPV-driven cancer constitutively expresses the viral oncoprotein E7, which interacts and blocks STING (Lau et al., 2015). Indeed, the response rate of HNSCC to checkpoint blockade is less than 20%, regardless of the HPV status (Ferris et al., 2016).

In certain embodiments, the type I interferon induction agent is any agent that increases type I interferon expression when introduced in a cell. Examples include, but are not limited to: c-di-GMP, c-di-AMP, cGAMP, c-di-IMP, c-di-UMP, and 5,6-dimethylxanthenone-4-acetic acid (DMXAA), 2'3'-cGAM(PS)2 (Rp/Sp), and 2'3'-c-di-AM (PS)2 (Rp,Rp). The structure of 2'3'-cGAM(PS)2 (Rp/Sp), is as follows:

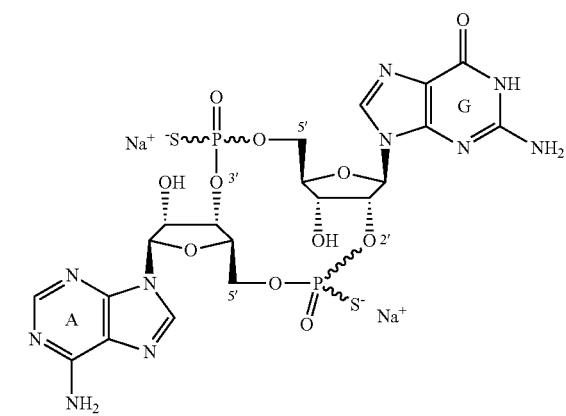

In other embodiments, the type I interferon induction agent is ML-RR-S2-CDA or ML-RS-S2-CDA as described in FIG. 3 of Fu et al., Sci Transl Med. 2015 Apr. 15; 7(283): 283ra52, which is herein incorporated by reference in it entirety.

II. Exemplary Antigens

The present disclosure is not limited by the type of antigen that is used with in the nano-satellite complexes and/or serum albumin carrier complexes. In certain embodiments, at least a portion of a human tumor-associated antigen is employed. Examples of human tumor-associated antigens (TAAs) include differentiation antigens (such as melanocyte differentiation antigens), mutational antigens (such as p53), overexpressed cellular antigens (such as HER2), viral antigens (such as human papillomavirus proteins), and cancer/testis (CT) antigens that are expressed in germ cells of the testis and ovary but are silent in normal somatic cells (such as MAGE and NY-ESO-1). In other embodiments, antigens from bacteria or viruses are employed.

In certain embodiments, the antigen is provided from the TANTIGEN web site that provide a comprehensive database of tumor T cell antigens (See, Olson et al., Cancer Immunol Immunother. 2017 Mar. 9, which is herein incorporated by reference in its entirety). Table 1 below provides a list of antigens, at least a portion of which may be employed with the nano-satellite complexes and/or serum albumin carrier complexes provided herein. The TANTIGEN web site may be used to select portions of a particular antigen. For example, with regard to the ERBB2/HER2 antigen, the TANTIGEN web site shows the amino acid sequence for this antigen, providing highlighted short antigenic regions of this antigen that are immunogenic (as shown in FIG. 14). One may employ one or more of the highlighted regions of this antigen in the complexes described herein. The same procedure may be employed with any of the antigens listed in Table 1 using the TANTIGEN web site or similar resource. In further embodiments, ongoing cancer deep sequencing provides new tools for additional neoantigen discovery which may be employed with the present disclosure. The nano-satellite complex and/or the serum albumin carrier-antigen-adjuvant complex are not limited by the specific sequences of the antigenic peptides. Both systems provide methods, compositions, and kits to specifically modulate the additional neoantigen-targeted immune response.

TABLE 1

| Antigen Name | Common Name | Antigen Name | Common Name |
|---|---|---|---|
| ERBB2 | HER2 | COTL1 | Coactosin-like 1 |
| BIRC5 | Survivin | CALR3 | CRT2 |
| CEACAM5 | CEA | PA2G4 | ErbB3-binding protein 1 |
| WDR46 | BING4 | EZH2 | Polycomb group protein enhancer of zeste homolog 2 (EZH2) |
| BAGE | BAGE1 | FMNL1 | Formin-related protein in leukocytes 1 (FMNL1) |
| CSAG2 | TRAG-3 | HPSE | Heparanase |
| DCT | TRP-2 | APC | — |
| MAGED4 | | UBE2A | — |
| GAGE1 | GAGE-1 | BCAP31 | — |
| GAGE2 | GAGE-2 | TOP2A | — |
| TGAGE3 | GAGE-3 | TOP2B | — |
| GAGE4 | GAGE-4 | ITGB8 | — |
| GAGE5 | GAGE-5 | RPA1 | — |
| GAGE6 | GAGE-6 | ABI2 | — |
| GAGE7 | GAGE-7 | CCNI | — |
| GAGE8 | GAGE-8 | CDC2 | — |
| IL13RA2 | Interleukin 13 receptor alpha 2 | 2-Sep | — |
| MAGEA1 | MAGE-A1 | STAT1 | — |
| MAGEA2 | MAGE-A2 | LRP1 | — |
| MAGEA3 | MAGE-A3 | ADAM17 | — |
| MAGEA4 | MAGE-A4 | JUP | — |
| MAGEA6 | MAGE-A6 | DDR1 | — |
| MAGEA9 | MAGE-A9 | ITPR2 | — |
| MAGEA10 | MAGE-A10 | HMOX1 | heme oxygenase-1 (HO-1) |
| MAGEA12 | MAGE-A12 | TPM4 | Tropomyosin-4 |
| MAGEB1 | MAGE-B1 | BAAT | — |
| MAGEB2 | MAGE-B2 | DNAJC8 | — |
| MAGEC2 | MAGE-C2 | TAPBP | — |
| TP53 | | LGALS3BP | Mac-2-binding protein |
| TYR | Tyrosinase | PAGE4 | PAGE-4 |
| TYRP1 | TRP-1 | PAK2 | P21-activated serin kinase 2 (PAK2) |
| SAGE1 | SAGE | CDKN1A | cyclin-dependent kinase inhibitor 1A (CDKN1A) |
| SYCP1 | HOM-TES-14/SCP1 | PTHLH | Parathyroid hormone-related protein (PTHrP) |
| SSX2 | SSX2 or HOM-MEL-40 | SOX2 | — |
| SSX4 | | SOX11 | — |
| KRAS | K-ras | TRPM8 | Prostate-specific protein transient receptor potential-p8 (trp-p8) |
| PRAME | | TYMS | Thymidylate synthase (TYMS) |
| NRAS | N-ras | ATIC | 5'-aminoimidazole-4-carboxamide-1-beta-d-ribonucleotide transfolmylase/inosinicase (AICRT/I) |
| ACTN4 | Alpha-actinin-4 | PGK1 | phosphoglycerate kinase 1 (PKG1) |
| CTNNB1 | | SOX4 | SOX-4 |
| CASP8 | Caspase-8 | TOR3A | ATP-dependent interferon-responsive (ADIR) |

TABLE 1-continued

| Antigen Name | Common Name | Antigen Name | Common Name |
|---|---|---|---|
| CDC27 | | TRGC2 | T-cell receptor gamma alternate heading frame protein (TARP) |
| CDK4 | | BTBD2 | BTB domain containing 2 (BTBD2) |
| EEF2 | | SLBP | hairpin-binding protein |
| FN1 | Fibronectin | EGFR | Epidermal growth factor receptor (EGFR) |
| HSPA1B | Hsp70 | IER3 | immediate early response gene X-1 (IEX-1) |
| LPGAT1 | KIAA0205 | TTK | TTK protein kinase (TTK) |
| ME1 | Malic enzyme | LY6K | lymphocyte antigen 6 complex locus K (LY6K) |
| HHAT | MART-2 | IGF2BP3 | insulin-like growth factor (IGF)-II mRNA binding protein 3 (IMP-3) |
| TRAPPC1 | MUM-2 | GPC3 | glypican-3 (GPC3) |
| MUM3 | MUM-3 | SLC35A4 | — |
| MYO1B | Unconventional myosin class I gene | HSMD | HMSD-v-encoded mHA |
| PAPOLG | neo-PAP | H3F3A | |
| OS9 | OS-9 | ALDH1A1 | aldehyde dehydrogenase 1 family member A1 (ALDH1A1) |
| PTPRK | Receptor-like protein tyrosine phosphatase kappa | MFI2 | Melanotransferrin |
| TPI1 | Triosephosphate isomerase or TPI1 | MMP14 | — |
| ADFP | Perilipin-2 | SDCBP | — |
| AFP | Alpha-fetoprotein | PARP12 | — |
| AIM2 | | MET | c-Met protein |
| ANXA2 | Annexin II | CCNB1 | cyclin B1 |
| ART4 | Endoplasmic reticulum-resident protein | PAX3-FKHR | — |
| CLCA2 | | PAX3 | — |
| CPSF1 | CPSF | FOXO1 | FKHR |
| PPIB | Cyclophilin B | XBP1 | XBP1 |
| EPHA2 | EphA2 | SYND1 | CD138 |
| EPHA3 | EphA3 | ETV5 | — |
| FGF5 | Fibroblast growth factor 5 or FGF5 | HSPA1A | — |
| CA9 | Carbonic anhydrase IX | HMHA1 | — |
| TERT | hTERT | TRIM68 | — |
| MGAT5 | GNT-V or N-acetylglucosaminytransferase V | ACSM2A | ACSM2A |
| CEL | intestinal carboxylesterase | ATR | ATR |
| F4.2 | | USB1 | USB1 |
| CAN | CAN protein | RTCB | RTCB |
| ETV6 | TEL1 or ETV6 | C6ORF89 | C6ORF89 |
| BIRC7 | Livin/ML-IAP | CDC25A | CDC25A |
| CSF1 | Macrophage colony stimulating factor | CDK12 | CDK12 |
| OGT | | CRYBA1 | CRYBA1 |
| MUC1 | Mucin or MUC1 | CSNK1A1 | CSNK1A1 |
| MUC2 | | DSCAML1 | DSCAML1 |
| MUM1 | MUM-1 | F2R | F2R |
| CTAG1 | NY-ESO-1 or LAGE-2 | FNDC3B | FNDC3B |
| CTAG2 | NY-ESO-ORF2 or LAGE-1 | GAS7 | GAS7 |
| CAMEL | | HAUS3 | HAUS3 |
| MRPL28 | Melanoma antigen p15 | HERC1 | HERC1 |
| FOLH1 | Prostate-specific membrane antigen | HMGN2 | HMGN2 |
| RAGE | | SZT2 | SZT2 |
| SFMBT1 | Renal ubiquitous protein 1 | LRRC41 | LRRC41 |
| KAAG1 | RU2AS | MATN2 | Matrilin-2 |
| SART1 | SART-1 | NIN | Ninein |
| TSPYL1 | SART-2 | PLEKHM2 | PLEKHM2 |
| SART3 | | POLR2A | POLR2A |
| SOX10 | | PPP1R3B | PPP1R3B |
| TRG | | RALGAPB | RALGAPB |
| WT1 | | SF3B1 | SF3B1 |
| TACSTD1 | Ep-CAM | SLC46A1 | SLC46A1 |
| SILV | Pmel 17 or gp100 | STRAP | STRAP |
| SCGB2A2 | Mammaglobin A | SYT15 | SYT15 |
| MC1R | | TBC1D9B | TBC1D9B |
| MLANA | MART-1 or Melan-A | THNSL2 | THNSL2 |
| GPR143 | OA1 | THOC6 | THOC6 |
| OCA2 | P polypeptide | WHSC1L1 | WHSC1L1 |
| KLK3 | PSA or Prostate-specific antigen | XPO1 | XPO1 |
| SUPT7L | ART-1 | BCL11A | BCL11A |

TABLE 1-continued

| Antigen Name | Common Name | Antigen Name | Common Name |
|---|---|---|---|
| ARTC1 | | SPEN | SPEN |
| BRAF | | VPS13D | VPS13D |
| CASP5 | Caspase-5 | SOGA1 | SOGA1 |
| CDKN2A | | MAP1A | MAP1A |
| UBXD5 | COA-1 | ZNF219 | ZNF219 |
| EFTUD2 | Elongation factor Tu GTP binding domain containing or SNRP116 | SYNPO | SYNPO |
| GPNMB | | NFATC2 | NFATC2 |
| NFYC | | NCBP3 | NCBP3 |
| PRDX5 | Peroxiredoxin 5 | HIVEP2 | HIVEP2 |
| ZUBR1 | E3 ubiquitin-protein ligase UBR4 | NCOA1 | NCOA1 |
| SIRT2 | | LPP | LPP |
| SNRPD1 | | ARID1B | ARID1B |
| HERV-K-MEL | | SYNM | SYNM |
| CXorf61 | Kita-kyushu lung cancer antigen 1; | SVIL | SVIL |
| CCDC110 | KM-HN-1 | SRRM2 | SRRM2 |
| VENTXP1 | NA88-A | RREB1 | RREB1 |
| SPA17 | Sperm protein 17 | EP300 | EP300 |
| KLK4 | | RCSD1 | RCSD1 |
| ANKRD30A | NY-BR-1 | CEP95 | CEP95 |
| RAB38 | NY-MEL-1 or RAB38 | IP6K1 | IP6K1 |
| CCND1 | Cyclin D1 | RSRP1 | RSRP1 |
| CYP1B1 | P450 1B1 or CYP1B1 | MYL9 | MYL9 |
| MDM2 | | TBC1D10C | TBC1D10C |
| MMP2 | Matrix metalloproteinase-2 | MACF1 | MACF1 |
| ZNF395 | Papillomavirus binding factor (PBF) | MAP7D1 | MAP7D1 |
| | | MORC2 | MORC2 |
| RNF43 | | RBM14 | RBM14 |
| SCRN1 | Secernin 1 | GRM5 | GRM5 |
| STEAP1 | STEAP | NIFK | NIFK |
| 707-AP | | TLK1 | TLK1 |
| TGFBR2 | TGF-beta receptor type IIB | IRS2 | IRS2 |
| PXDNL | MG50 | PPP1CA | PPP1CA |
| AKAP13 | Lymphoid blast crisis oncogene (Lbc) oncoproptein | GPSM3 | GPSM3 |
| PRTN3 | Proteinase 3 | SIK1 | SIK1 |
| PSCA | Prostate stem cell antigen | HMGN1 | HMGN1 |
| RHAMM | RHAMM/CD168 | MAP3K11 | MAP3K11 |
| ACPP | Prostatic acid phosphatase | GFI1 | GFI1 |
| ACRBP | OY-TES-1 | KANSL3 | KANSL3 |
| LCK | Lck | KLF2 | KLF2 |
| RCVRN | Recoverin | CCDC88B | CCDC88B |
| RPS2 | Ribosomal protein S2 | TNS3 | TNS3 |
| RPL10A | Ribosomal protein L10a | N4BP2 | N4BP2 |
| SLC45A3 | Prostein | TPX2 | TPX2 |
| BCL2L1 | Bcl-xL | KMT2A | KMT2A |
| DKK1 | Dickkopf-1 (DKK1) | SRSF7 | SRSF7 |
| ENAH | Human Mena protein | GRK2 | GRK2 |
| CSPG4 | Melanoma-associated chondroitin sulfate proteoglycan (MCSP) | | |
| RGS5 | | GIGYF2 | GIGYF2 |
| BCR | Breakpoint cluster region | SCAP | SCAP |
| BCR-ABL | | MIIP | MIIP |
| ABL-BCR | | ZC3H14 | ZC3H14 |
| DEK | DEK oncogene | ZNF106 | ZNF106 |
| DEK-CAN | | SKI | SKI |
| ETV6-AML1 | | SETD2 | SETD2 |
| LDLR-FUT | | ATXN2L | ATXN2L |
| NPM1-ALK1 | | SRSF8 | SRSF8 |
| PML-RARA | | LUZP1 | LUZP1 |
| SYT-SSX1 | | KLF10 | KLF10 |
| SYT-SSX2 | | RERE | RERE |
| FLT3 | FLT1 | MEF2D | MEF2D |
| ABL1 | Proto-oncogene tyrosine-protein kinase ABL1 | PCBP2 | PCBP2 |
| AML1 | AML | LSP1 | LSP1 |
| LDLR | Low density lipid receptor (LDLR) | MEFV | MEFV |
| FUT1 | GDP-L-fucose | ARHGAP30 | ARHGAP30 |
| NPM1 | NPM | CHAF1A | CHAF1A |
| ALK | | FAM53C | FAM53C |
| PML1 | promyelocytic leukemia or PML | ARHGAP17 | ARHGAP17 |
| RARA | RAR alpha | HSPB1 | HSPB1 |
| SYT | | NCOR2 | NCOR2 |

TABLE 1-continued

| Antigen Name | Common Name | Antigen Name | Common Name |
|---|---|---|---|
| SSX1 | | ATXN2 | ATXN2 |
| MSLN | Mesothelin | RBM15 | RBM15 |
| UBE2V1 | Ubiquitin-conjugating enzyme variant Kua | RBM17 | RBM17 |
| HNRPL | | SON | SON |
| WHSC2 | | TSC22D4 | TSC22D4 |
| EIF4EBP1 | | MYC | MYC |
| WNK2 | | | |
| OAS3 | | | |
| BCL-2 | Bcl-2 | | |
| MCL1 | Mcl-1 | | |
| CTSH | Cathepsin H | | |
| ABCC3 | Multidrug resistance-associated protein 3 (MRP3) | | |
| BST2 | HM1.24 | | |
| MFGE8 | Milk fat globule membrane protein BA46 (lactadherin) | | |
| TPBG | 5T4 oncofetal antigen | | |
| FMOD | Fibromodulin (FMOD) | | |
| XAGE1 | XAGE antigen | | |
| RPSA | Oncofetal Ag immature laminin receptor (OFA-iLR) | | |

In certain embodiments, the antigen employed in the complexes described herein is from a human oncogenic or tumor virus. Viruses that are associated with human malignancies include: HTLV-1 (adult T-cell leukemia (ATL), HPV (cervical cancer, skin cancer in patients with epidermodysplasia verruciformis (EV), head and neck cancers, and other anogenital cancers); HHV-8 (Kaposi's sarcoma (KS), primary effusion lymphoma, and Castleman's disease), EBV (Burkitt's Lymphoma (BL), nasopharyngeal carcinoma (NPC), MCPyV (Merkel Cell Carcinoma), post-transplant lymphomas, and Hodgkin's disease), HBV, and HCV (hepatocellular carcinoma (HCC)). Additionally, viruses with possible roles in human malignancies include: simian vacuolating virus 40 (SV40) (brain cancer, bone cancer, and mesothelioma), BK virus (BKV) (prostate cancer), JC virus (JCV) (brain cancer), human endogenous retroviruses (HERVs) (germ cell tumors, breast cancer, ovarian cancer, and melanoma), human mammary tumor virus (HMTV) (breast cancer), and (vi) Torque teno virus (TTV) (gastrointestinal cancer, lung cancer, breast cancer, and myeloma).

In certain embodiments, antigens from viruses or bacteria are employed with the nano-satellite and serum albumin complexes described herein. Such antigens are well known in the art. Examples of viruses (Table 5) and bacteria (Table 6) that are the source of such well-known antigens are provided below.

TABLE 5

| Viral diseases | |
|---|---|
| Virus antigen source | Diseases or conditions |
| Hepatitis A virus | Hepatitis A |
| Hepatitis B virus | Hepatitis B |
| Hepatitis E virus | Hepatitis E |
| Human papillomavirus | Cervical cancer, Genital warts, anogenital cancers |
| Influenza virus | Influenza |
| Japanese encephalitis virus | Japanese encephalitis |
| Measles virus | Measles |
| Mumps virus | Mumps |
| Polio virus | Poliomyelitis |
| Rabies virus | Rabies |
| Rotavirus | Rotaviral gastroenteritis |
| Rubella virus | Rubella |
| Tick-borne encephalitis virus | Tick-borne encephalitis |
| Varicella zoster virus | Chickenpox, Shingles |
| Variola virus | Smallpox |
| Yellow fever virus | Yellow fever |

TABLE 6

| Bacterial diseases | |
|---|---|
| Bacterium antigen source | Diseases or conditions |
| *Bacillus anthracis* | Anthrax |
| *Bordetella pertussis* | Whooping cough |
| *Clostridium tetani* | Tetanus |
| *Corynebacterium diphtheriae* | Diphtheria |
| *Coxiella burnetii* | Q fever |
| *Haemophilus* influenzae type B (Hib) | Epiglottitis, meningitis, pneumonia |
| *Mycobacterium tuberculosis* | Tuberculosis |
| *Neisseria meningitidis* | Meningococcal meningitis |
| *Salmonella typhi* | Typhoid fever |
| *Streptococcus pneumoniae* | Pneumococcal pneumonia |
| *Vibrio cholerae* | Cholera |

III. Utilizing Serum Albumin Carrier to Deliver Type I Interferon Agonist and Antigens The present disclosure is not limited by the methods used to cross-link type I interferon-inducing agents, including STING agonists, and/or antigen to the serum albumin component (e.g., or albumin nanoparticle (e.g., 10-500 nm)). In certain embodiments, one may employ heterobifunctional crosslinkers (e.g., NHS-linker-maleimide, or NHS-linker-pyridyldithiol or NHS-linker-haloacetyl) or hetero-multifunctional crosslinkers to link the amine groups in human serum albumin (or other albumin protein) or albumin nanoparticle, to sulfhydryl group in peptides and phosphorothioate in cGAM(PS)$_2$. Exemplary methods and cross-linkers are provided below.

Heterobifunctional Crosslinkers
Exemplary Method 1:
NHS-linker-maleimide
This kind of linker includes but not limits to AMAS, BMPS, GMBS, MBS, SMCC, EMCS, SMPB, SMPH, LC-SMCC, KMUS and NHS-PEGn-Maleimide, which are shown in Table 2 below.
TABLE 2
| Cross-linker name | Spacer arm length (nm) | structure |
| --- | --- | --- |
| AMAS | 0.44 | 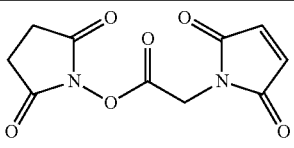 |
| BMPS | 0.59 | 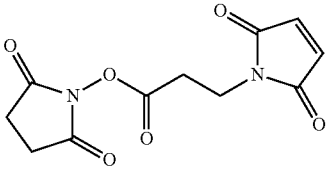 [SMILES: O=C(CCN1C(=O)C=CC1=O)ON1C(=O)CCC1=O] |
| GMBS | 0.73 | 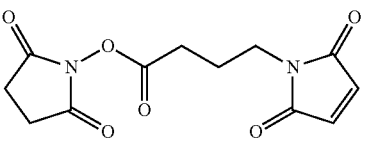 [SMILES: O=C(CCCN1C(=O)C=CC1=O)ON1C(=O)CCC1=O] |
| MBS | 0.73 | 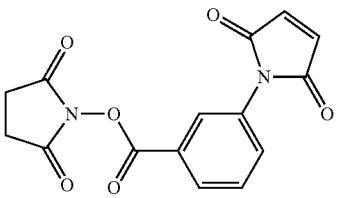 [SMILES: O=C(ON1C(=O)CCC1=O)c1cccc(N2C(=O)C=CC2=O)c1] |
| SMCC | 0.83 | 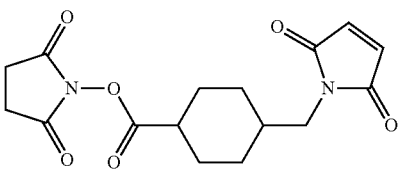 [SMILES: O=C(ON1C(=O)CCC1=O)C1CCC(CN2C(=O)C=CC2=O)CC1] |
| EMCS | 0.94 | 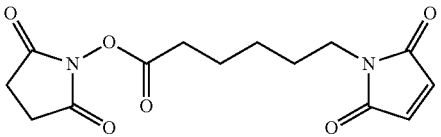 [SMILES: O=C(CCCCCN1C(=O)C=CC1=O)ON1C(=O)CCC1=O] |
| SMPB | 1.16 | 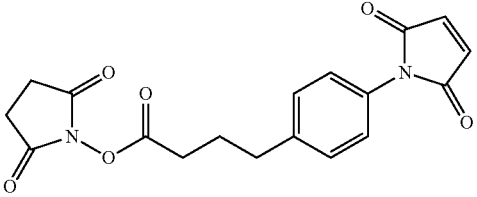 [SMILES: O=C(CCCc1ccc(N2C(=O)C=CC2=O)cc1)ON1C(=O)CCC1=O] |
| SMPH | 1.42 | 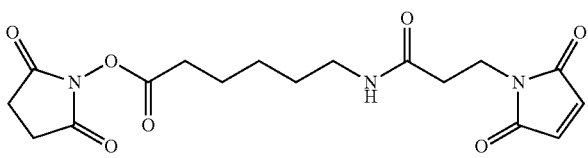 [SMILES: O=C(CCN1C(=O)C=CC1=O)NCCCCCC(=O)ON1C(=O)CCC1=O] |

TABLE 2-continued

| Cross-linker name | Spacer arm length (nm) | structure |
|---|---|---|
| LC-SMCC | 1.62 | 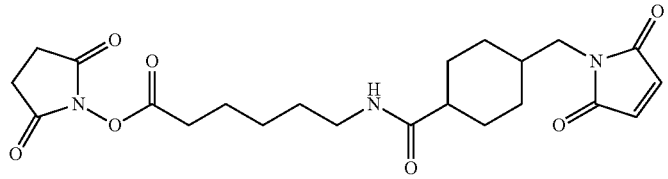 [SMILES: O=C(CCCCCNC(=O)C1CCC(CN2C(=O)C=CC2=O)CC1)ON1C(=O)CCC1=O] |
| KMUS | 1.63 | 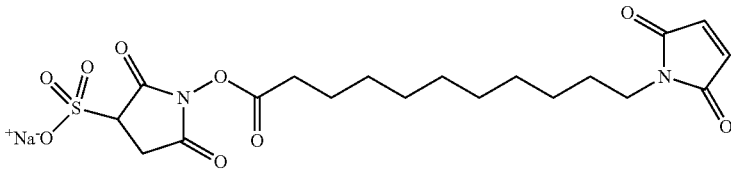 |
| NHS-PEG2-Maleimide | 1.76 | 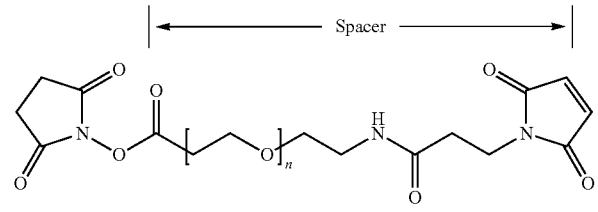 n = 2 |
| NHS-PEG4-Maleimide | 2.46 | n = 4 |
| NHS-PEG6-Maleimide | 3.25 | n = 6 |
| NTS-PEG8-Maleimide | 3.9 | n = 8 |
| NHS-PEG12-Maleimide | 5.34 | n = 12 |
| NHS-PEG24-Maleimide | 9.52 | n = 24 |
| NHS-PEGn-Maleimide (MW 2000) | | 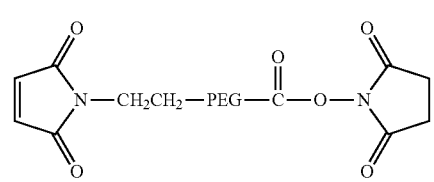 MW = 2000 |
| NHS-PEGn-Maleimide (MW 3400) | | MW = 3400 |
| NHS-PEGn-Maleimide (MW 5000) | | MW = 5000 |
| NHS-PEGn-Maleimide (MW 10000) | | MW = 10000 |

FIG. 15 shows general conjugation steps, using sulfo-SMCC as an exemplary cross-linker, for conjugating a peptide antigen and/or cGAMP to human serum albumin (HSA). Exemplary methods are as follows:

1) Dissolve HSA in Conjugation Buffer at 0.1 mM (conjugation buffer: PBS, pH 7.2, EDTA 1-5 mM).
2) Add cross-linker to dissolved HSA at 1 mM final (=10-fold molar excess).
3) Incubate reaction mixture for 30 min at RT or 2 hours at 4° C.
4) Remove excess cross-linker using Nanosep Centrifugal Devices (30K cut off, 10 min, wash twice).
5) Combine and mix cGAM(PS)$_2$ and purified HSA in an appropriate molar ratio at RT for overnight.
6) Combine and mix peptides and the product above in an appropriate molar ratio at RT for 30 min.

Exemplary Method 2:
NHS-linker-pyridyldithiol
This kind of linker includes but not limits to SPDP, PEG-SPDP, SMPT and Sulfo-LC-SMPT, as shown in Table 3.

TABLE 3

| Cross-linker name | Spacer arm length (nm) | structure |
|---|---|---|
| SPDP | 0.68 | 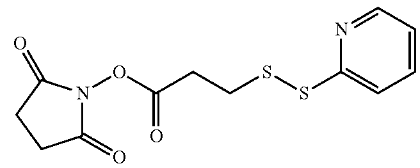 [SMILES: O=C(CCSSc1ccccn1)ON1C(=O)CCC1=O] |
| LC-SPDP | 1.56 | 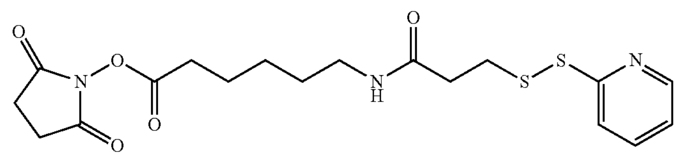 [SMILES: O=C(CCSSc1ccccn1)NCCCCCC(=O)ON1C(=O)CCC1=O] |
| Sulfo-LC-SPDP | 1.56 | 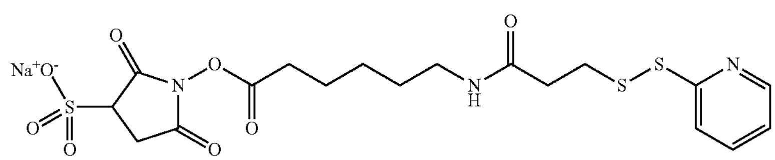 |
| SMPT | 1.12 | 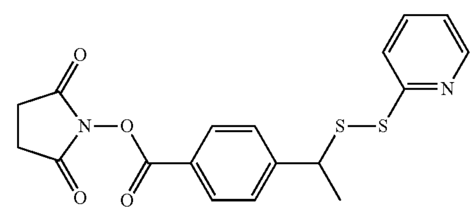 [SMILES: CC(SSc1ccccn1)c1ccc(C(=O)ON2C(=O)CCC2=O)cc1] |
| Sulfo-LC-SMPT | 2 | 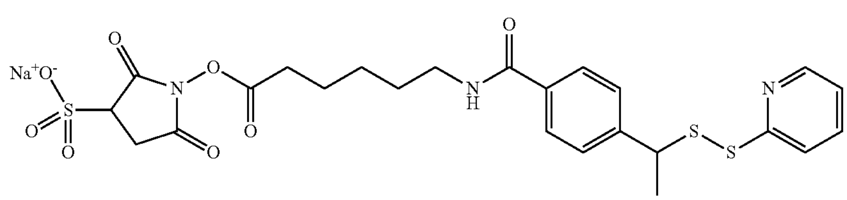 |
| PEG4-SPDP | 2.57 | 25.7 Å |
| PEG12-SPDP | 5.41 | 54.1 Å |

FIG. 16 shows general conjugation steps (using SPDP as an example crosslinker), to link HSA to peptides or cGAMPs. Exemplary methods are as follows:

1) Dissolve HSA in Conjugation Buffer at 0.1 mM (conjugation buffer: PBS, pH 7.2, EDTA 1-5 mM).
2) Prepare a 20 mM solution of crosslinker reagent (dissolve in DMSO or DMF).
3) Add cross-linker to dissolved HSA at 1 mM final (=10-fold molar excess).
4) Incubate reaction mixture for 30 min at RT or 2 hours at 4° C.
5) Remove excess cross-linker using Nanosep Centrifugal Devices (30K cut off, 10 min, wash twice).
6) Combine and mix cGAM(PS)$_2$ and purified HSA in an appropriate molar ratio at RT for overnight.
7) Combine and mix peptides and the product above in an appropriate molar ratio at RT for overnight.

Exemplary Method 3:

NHS-linker-haloacetyl

This kind of linker includes but not limits to SIA, SIAB, Sulfo-SIAB and SBAP as shown in Table 4.

TABLE 4

| Cross-linker name | Spacer arm length (nm) | structure |
|---|---|---|
| SIA | 0.15 | 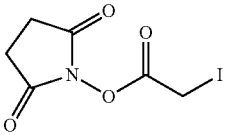 [SMILES: O=C(CI)ON1C(=O)CCC1=O] |
| SBAP | 0.625 | 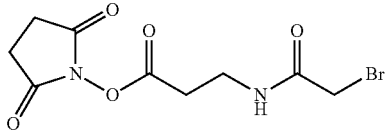 [SMILES: O=C(CBr)NCCC(=O)ON1C(=O)CCC1=O] |
| SIAB | 1.06 | 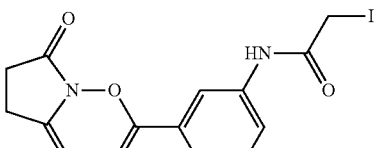 |
| Sulfo-SIAB | 1.06 | 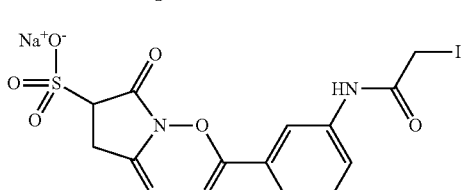 |

FIG. 17 shows general conjugation steps (using SIA as an example crosslinker), to link HSA to peptides or cGAMPs. Exemplary methods are as follows:

1) Dissolve HSA in Conjugation Buffer at 0.1 mM (conjugation buffer: PBS, pH 7.2, EDTA 1-5 mM).
2) Prepare a 20 mM solution of crosslinker reagent (dissolve in DMSO or DMF, protect from light).
3) Add cross-linker to dissolved HSA at 1 mM final (=10-fold molar excess).
4) Incubate reaction mixture for 30 min at RT or 2 hours at 4° C.
5) Remove excess cross-linker using Nanosep Centrifugal Devices (30K cut off, 10 min, wash twice).
6) Combine and mix cGAM(PS)$_2$ and purified HSA in an appropriate molar ratio at RT for overnight in the dark.
7) Combine and mix peptides and the product above in an appropriate molar ratio at RT for 1 h in the dark.
8) Add cysteine to a final concentration of 5 mM and react for 15 min at RT in the dark.

Hetero-Multi-Functional Crosslinkers

Exemplary hetero-multi-functional cross-linkers may be employed, such as the following:

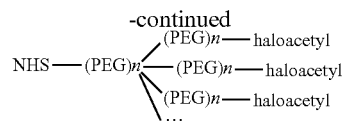

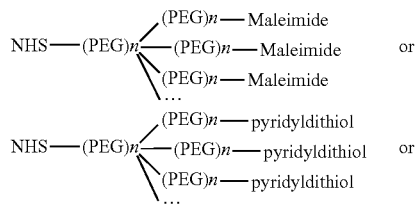

EXAMPLES

Example 1

Type I Interferon-Inducing Nanosatellite Vaccine

This Examples describes the ability of a Type I Interferon-inducing Nanosatellite vaccine to mitigate immune suppression in Head and Neck Squamous Cell Carcinoma.

Methods

Cell culture: UMSCC22b and UMSCC47 were obtained from the U-M Head and Neck Cancer SPORE. PCI-13 was obtained from the University of Pittsburgh Head and Neck Cancer SPORE. HEK-293T was purchased from ATCC. The human HNSCC cells and HEK293T cells were maintained in complete DMEM medium. The MOC2-E6/E7 cells were obtained from Dr. David Mooney at Harvard University, the parental and derivative cell lines were cultured in 30% F12 nutrient mix (Thermo Fisher Scientific, Waltham, Mass.), 5% FBS, puromycin (2 mg/ml), insulin (4 mg/ml), hydrocortisone (200 ug/ml), EGF (100 ug/ml) and penicillin (100 U/ml) and streptomycin (100 mg/ml). THP1-blue ISG cells (Cat. thp-isg, InvivoGen, San Diego, Calif.) were cultured in RPMI media supplemented with 10% FBS, 1% penicillin, streptomycin, Normocin and Zeocin. NK cells, T cells, and tumor-infiltrating lymphocytes were cultured in complete RPMI 1640 medium. Peripheral blood monocytes were separated from healthy volunteers using Ficoll-Paque gradient. Primary human NK and CD8+ T cells were separated using a NK cell enrichment kit and a CD8+ T cell enrichment kit, respectively (Cat. 19055 and Cat. 19053, STEMCELL Technologies Inc, Cambridge, Mass.). All cells were cultured in 37° C. incubator with 5% $CO_2$.

Experimental animals and treatments: Female C57BL6 mice, aged 6-8 weeks, were purchased from the Jackson Laboratory, and maintained in a pathogen-free facility at the University of Michigan. All animal work were done in accordance with and approved by the Institutional Animal Care & Use Committee (IACUC) at the University of Michigan, Ann Arbor. Syngeneic squamous cell carcinoma cells were implanted subcutaneously at the neck. Tumors were measured every other day using a caliper, and the tumor volume was calculated as $0.52 \times length \times width^2$. For the growth rates of Sox2-expressing tumors, a dose of 20-Gy irradiation was administered on day 14 post-implantation. To test the efficacy of the vaccine formulations, MOC2-E6/E7 cells were implanted subcutaneously on the back of the neck on day 0. The mice were either vaccinated with mock (PBS, 100 μl), 2'3'-cGAMP (50 μg/100 μl) (Cat. tlrl-nacga23-1, InvivoGen, San Diego, Calif.), peptides (18.5 nmol/100 μl), and full vaccine SatVax (2'3' cGAMP [50 ug] and peptide [18.5 nmol] conjugated with the nanosatellite/100 μl) administered subcutaneously at the tail base on days 3, 10 and 17 post-tumor implantation. Anti-PD-L1 (100 μg/100 μl) (clone B7H1, BioXCell, West Lebanon, N.H.) was administered through intraperitoneal injection on day 1 and 4 after each vaccination.

Plasmids, molecular cloning, and production of expression retroviruses and CRISPR-Cas9 lentiviruses: HA-tagged human and mouse STING expression plasmids were a kind gift from Dr. Glen N. Barber at the University of Miami. ISRE luciferase reporter construct, retroviral, and lentiviral packaging vectors were generously provided by Dr. Jenny P.-Y. Ting at the University of North Carolina at Chapel Hill. LC3B-GFP expression vector, HPV16 E6/E7 retroviral expression vector, Sox2 retroviral expression vector, and lentiCRISPRv2 construct were acquired through Addgene. The sgRNA sequence targeting SOX2 is 5'-AT-TATAAATACCGGCCCCGG (SEQ ID NO:39).

Transfections and viral transductions: HNSCC and HEK293T cells were plated so that they could reach about 70% confluence the next day for transfections using Lipofectamine 2000 (Cat. 11668019, Thermo Fisher Scientific, Waltham, Mass.) according to manufacturer's protocol. For transfection of IFN-1 agonists, 1 ug/ml of plasmid or poly (dA:dT) (Cat. tlrl-pain-1, InvivoGen, San Diego, Calif.) was used and cells were harvested 16 hrs later for RNA or protein. MOC2-E6/E7 cells stably expressing pMXS-gW (empty vector (EV) control) or pMXS-Sox2 were generated by retroviral transduction. Cells were transduced three times with each retrovirus to ensure sufficient Sox2 expression by addition of 10 μg/ml polybrene to retroviral supernatant before adding to cells. Immunoblot analysis was performed to verify Sox2 expression. For the generation of SOX2-deficient PCI-13 cells using CRISPR/Cas9 system, lentiviral particles with lentiCRISPRv2 (control) or lentiCRISPRv2-SOX2gRNA were added to cells with 10 μg/ml polybrene. After two days, cells were selected in 15 μg/ml puromycin for three days. Cells were subsequently grown in media with 5 μg/ml puromycin, and immunoblot was performed to verify that SOX2 was deficient.

Quantitation of gene expression: For analysis of mRNA in THP1-blue ISG cells, cells were seeded at one million cells/well in a 6-well plate. The cells were treated 16 hours with either media, nanosatellites, 2'3'-cGAMP (1 μg/ml or 10 μg/ml final concentration) (Cat. tlrl-nacga23-1, InvivoGen, San Diego, Calif.), or the vaccine with cGAMP (1 μg/ml or 10 μg/ml final concentration). Total RNA was isolated from cells using the QIAshredder and RNeasy Plus mini Kit (Cat. 79654 and Cat. 74134, Qiagen, Germantown, Md.). RNA was quantitated using Nanodrop, and reverse transcription was performed using High-Capacity RNA-to-cDNA kit (Cat. 4387406, Thermo Fisher Scientific, Waltham, Mass.). For real-time PCR, the cDNA was diluted and reactions were set up using the PowerUp SYBR Green Master Mix (Cat. A25776, Thermo Fisher Scientific, Waltham, Mass.) and ran on 7900HT Fast Real-Time PCR System (Thermo Fisher Scientific, Waltham, Mass.). All data were analyzed using the comparative $C_T$ method, and normalized to the corresponding HPRT mRNA levels. The primers are: IFNB1 F 5'-CATTACCTGAAGGCCAAGGA (SEQ ID NO:1), R 5'-CAATTGTCCAGTCCCAGAGG (SEQ ID NO:2); CXCL9 F 5'-GTGGTGTTCTTTTCCTCTTGGG-3' (SEQ ID NO:3), R 5'-ACAGCGACCCTTTCTCACTAC-3' (SEQ ID NO:4); CXCL10 F 5'-CTCCAGTCTCAGCACCATGA (SEQ ID NO:5), R 5'-GCTCCCCTCTGGTTTTAAGG (SEQ ID NO:6); ISG15 F 5'-CTGAGAGGCAGCGAACTCAT (SEQ ID NO:7), R 5'-AGCATCTTCACCGTCAGGTC (SEQ ID NO:8); SOX2 F 5'-CCCACCTACAGCATGTCCTACTC (SEQ ID NO:9), R 5'-TGGAGTGGGAGGAAGAGGTAAC (SEQ ID NO:10); STAT3 F 5'-TGAGACTTGGGCTTAC-CATTGGGT (SEQ ID NO:11), R 5'-TCTTTAATGGGC-CACAACAGGGCT (SEQ ID NO:12); STAT1 F 5'-GAGCAGGTTCACCAGCTTTATGAT (SEQ ID NO:13), R 5'-AACGGATGGTGGCAAATGA (SEQ ID NO:14); NLRX1 F 5'-AGCTGCTATCATCGTCAAC-3' (SEQ ID NO:15), R 5'-ACCGCAGATCTCACCATAG-3' (SEQ ID NO:16); NLRC3 F 5'-GTGCCGACCGACT-CATCTG-3' (SEQ ID NO:17), R 5'-GTCCTGCACTCATC-CAAGC-3' (SEQ ID NO:18); HPRT1 F 5'-ATGCTGAG-GATTTGGAAAGG (SEQ ID NO:19), R 5'-CAGAGGGCTACAATGTGATGG-3' (SEQ ID NO:20); Ifnb1 F 5'-CCAGCTCCAAGAAAGGACGA (SEQ ID NO:21), R 5'-CGCCCTGTAGGTGAGGTTGAT (SEQ ID NO:22); Cxcl9 F 5'-GAGCAGTGTGGAGTTCGAGG (SEQ ID NO:23), R 5'-TCCGGATCTAGGCAGGTTTG (SEQ ID NO:24); Cxcl10 F 5'-AATGAGGGCCATAGG-GAAGC (SEQ ID NO:25), R AGCCATC-CACTGGGTAAAGG (SEQ ID NO:26); Mx1 F 5'-TCT-GAGGAGAGCCAGACGAT-3' (SEQ ID NO:27), 5'-ACTCTGGTCCCCAATGACAG-3' (SEQ ID NO:28); Ifng F 5'-CGGCACAGTCATTGAAAGCCTA (SEQ ID NO:29), R 5'-GTTGCTGATGGCCTGATTGTC (SEQ ID NO:30); Hprt F 5'-GATfAGCGATGATGAACCAGGT-3' (SEQ ID NO:31), R 5'-CCTCCCATCTCCTFCATCACA-3' (SEQ ID NO:32).

RNA-Seq and pathway enrichment analysis: Total RNA from parental and immune cell-resistant HNC cells was isolated using the RNeasy plus mini kit (Cat. 74134, Qiagen, Germantown, Md.). poly A-based libraries were then constructed for each sample. Paired-end 50 nt reads next-gen sequencing was performed using the prepared libraries at the U-M DNA Sequencing Core. Result reads were mapped to the hg19 genome assembly using MapSplice v2.1.6 (Wang et al., 2010), and gene expression was quantified using RSEM and normalized within sample (Li and Dewey, 2011). An R package, edgeR (Robinson et al., 2010), was used to identify the genes that are differentially expressed among cell lines, and the top 2000 most significant genes were selected for gene set enrichment analysis using GSEA v2.2.4 (Subramanian et al., 2005).

Flow cytometric characterization of tumor-Infiltrating lymphocytes: Excised tumors were cut into small pieces of ~1-2 mm in length in RPMI 1640 media (Corning, Corning, N.Y.), and then mechanically dissociated by passing the tumors through a 70 μm cell strainer with the rubber stopper of the syringe plunger to obtain single cell suspension. TILs were isolated by density gradient using Ficoll-Paque PLUS (Cat. 17-1440-03, GE Healthcare Life Sciences, Pittsburgh, Pa.) washed twice in RPMI 1640 with 10% FBS, penicillin (100 U/ml) and streptomycin (100 mg/ml) and counted. The following antibodies were used for flow cytometry: anti-CD3-PE (BD Biosciences, San Jose, Calif.; clone 17A2), anti-CD4-PerCPCy5.5 (Biolegend, San Diego, Calif.; clone RM4-5), anti-CD8-FITC (Biolegend, San Diego, Calif.; clone 53-6.7), anti-CD279-PE-Cy7 (Biolegend, San Diego, Calif.; clone 29F.1A12), and staining of a tetramer recognizing $H-2D^b$-restricted HPV16 E7 epitope RAHYNIVTF (NIH tetramer core). Cells were stained for BV421-E7 tetramer for 30 mins at RT in dark, and washed twice in FACS buffer before staining for cell surface markers for 30 mins at RT in dark. Following two washes, cells were then stained for viability using Fixable Viability Dye APC-eFluor 780 (Cat. 65-0865-14, Thermo Fisher Scientific, Waltham, N.Y.). All staining was done in FACS buffer (2% FBS in PBS). Acquisition and compensation was performed on Beckman Coulter CyAn ADP. FlowJo V10 software was used to analyze the data.

Immunoblots and antibodies: Cells were lysed in RIPA buffer (1% Triton X-100, 0.25% DOC, 0.05% SDS, 50 mM Tris-HCl pH8.0, 150 mM NaCl and 50 mM NaF) containing complete protease inhibitor cocktail (Cat. 11873580001, Roche, Indianapolis, Ind.) and Halt Phosphatase Inhibitor Cocktail (Cat. 78420, Thermo Fisher Scientific, Waltham, N.Y.). Lysates were then quantitated using BCA assay (Cat. 23225, Thermo Fisher Scientific, Waltham, N.Y.) and equal amounts of protein samples were separated by Novex 4-12% Tris-Glycine Mini Gels (Cat. XP04122BOX, Thermo Fisher Scientific, Waltham, N.Y.) or PAGEr precast 15% Tris-glycine gels (Cat. 59504, Lonza, Basel, Switzerland). The antibodies used are as following: beta-actin (Cat. ab49900, Abcam, Cambridge, United Kingdom), phospho-TBK1 (Ser172) (Cat. 5483S, Cell Signaling Technology, Danvers, Mass.), TBK1 (Cat. 3504S, Cell Signaling Technology, Danvers, Mass.), phosphor-IRF3 (Ser396) (Cat. 4947S, Cell Signaling Technology, Danvers, Mass.), IRF3 (Cat. PA5-20086, Thermo Fisher Scientific, Waltham, N.Y.), phospho-p65 (Ser536) (Cat. 3033S, Cell Signaling Technology, Danvers, Mass.), p65 (Cat. PA1-186, Thermo Fisher Scientific, Waltham, N.Y.), SOX2 (Cat. 23064, Cell Signaling Technology, Danvers, Mass.), STING (Cat. 13647, Cell Signaling Technology, Danvers, Mass.), LC3B (Cat. 2775, Cell Signaling Technology, Danvers, Mass.) and secondary antibody goat pAb to Rb IgG HRP (Cat. Ab97051, Abcam, Cambridge, United Kingdom). Signals were detected using SuperSignal West Pico Chemiluminescent Substrate (Cat. 34080, Thermo Fisher Scientific, Waltham, N.Y.).

AlamarBlue assay: 500 cells were seeded into each well of clear bottom black polystyrene TC-treated 96-well microplates (Cat. 3904, Corning, Corning, N.Y.) and at each indicated time-point, media was removed and fresh media with 10% alamarBlue (Cat. DAL1025, Thermo Fisher Scientific, Waltham, N.Y.) was added to each well and incubated at 37° C. for 4 h. Fluorescence readings (Ex. 560 nm/Em. 590 nm) were carried out using Gen 5 microplate reader and imager software (BioTek, Winooski, Vt.).

Luciferase assay: Assays were performed as previously described (Lei et al., 2012). Briefly, 96-well plates were coated with poly-L-lysine solution (Cat. P8920, Sigma-Aldrich, St Louis, Mo.) before $1 \times 10^4$ HEK-293T cells were plated overnight and transfected with 25 ng of ISRE-luciferase reporter and titrating doses of pcDNA3.3-SOX2 using Lipofectamine 2000 (Cat. 11668019, Thermo Fisher Scientific, Waltham, N.Y.). pcDNA3.1 was added to keep the amounts of DNA between well constant. The next day, cells were transfected with Song of STING plasmid or poly (dA:dT) (Cat. tlrl-patn-1, InvivoGen, San Diego, Calif.) and harvested 16 hrs post-transfection. Cells were lysed in Luciferase cell culture lysis buffer (Cat. E1531, Promega, Madison, Wis.), and incubated with luciferase assay buffer (15 mM potassium phosphate (pH 7.8), 25 mM glycylglycine, 15 mM $MgSO_4$, 4 mM EGTA, 2 mM ATP, 1 mM DTT) and luciferin solution (0.2 mM D-luciferin [Cat. L6882, Sigma-Aldrich, St Louis, Mo.], 15 mM $MgSO_4$, 25 mM glycylglycine, 2 mM DTT). Luciferase was measured using a CLARIOstar plate reader (BMG Labtech, Ortenberg, Germany).

Immunohistochemistry: Tumors were fixed with 4% paraformaldehyde overnight and moved to 70% ethanol before being embedded in paraffin. They were then sectioned with a microtome and stained using the following antibodies: SOX2 (Cat. 23064, Cell Signaling Technology), Mx1 (Cat. HPA030917, Sigma-Aldrich) using Vectastain ABC HPR kit (Cat. PK-4001, Vector Laboratories, Burlingame, Calif.).

ISRE reporter assay: $0.1 \times 10^6$ THP1-blue ISO cells were seeded into each well of 96 well-plate with the 180 μl of the complete media and 20 μl of each of the following: control (media alone), cGAMP (1 μg/ml or 10 μg/ml final concentration) (Cat. tlrl-nacga23-1, InvivoGen, San Diego, Calif.), nanosatellites particles, or SatVax (Nanoparticle satellite+ antigen). The cGAMP in the vaccine had the same final concentration with the cGAMP control groups. The cells were incubated with the treatment for 16 h in 37° C. incubator with 5% $CO_2$. The supernatants were taken out and incubated with QUANTI-Blue (Cat. rep-qb1, InvivoGen, San Diego, Calif.) according to the manufacturer's protocol and absorption was measured at 655 nm.

Nanosatellite vaccine uptake study in bone marrow-derived macrophage (BMM): E7 peptide labeled with 6-FAM was conjugated with nanosatellites for cell uptake study compared with unconjugated E7-FAM peptide. Bone marrow-derived macrophages were isolated from femur and tibia of C57BL/6 mice and cultured for 6 days in 10 mm non-tissue culture dishes supplemented with RPMI 1640 media with 30% L-929 conditioned media, 20% FBS, penicillin (100 U/ml) and streptomycin (100 mg/ml). On day 6, $4 \times 10^4$ cells were seeded into a black 96-well plate supplemented with the RPMI 1640 media with 10% FBS, penicillin (100 U/ml) and streptomycin (100 mg/ml). On the next day, the media was removed and replaced with phenol red-free and FBS-free RPMI media. Nanosatellite vaccine and other controls were incubated with the cells for 2 and 6 hrs and the cells were then washed thrice with PBS. Fluorescent signal was read at the excitation 490 nm and emission 520 nm.

Dendritic cell maturation assay: Bone marrow-derived dendritic cells (BMDC) were obtained from 8-week-old C57BL/6 mice. The cells were cultured in RPMI media supplemented with 10% heat-inactivated FBS, penicillin (100 U/ml), streptomycin (100 mg/ml), glutamine, non-essential amino acid, sodium pyruvate, 2-mercaptoethanol, and 10 ng/ml GM-CSF (PeproTech, USA). The new completed media supplemented with 20 ng/ml GM-CSF were added on day 3. $0.5 \times 10^6$, cells were seeded into 12-well plate on day 6 and incubated overnight. The cells were then treated with PBS, cGAMP alone (10 ug/ml), the peptides, vaccine (cGAMP 10 ug/ml) or lipopolysaccharide (200 ng/ml) (eBiosciences). 48 hrs after incubation, the cells were washed 3 times with PBS before harvest. The Fc blocker CD16/32 (clone 93, eBiosciences) was used to block non-specific binding before staining with the surface marker antibodies. The cells were then staining with MHC-II-FITC (clone MS/114.15.2, eBiosciences) and CD86 PE (clone GL1, eBiosciences) for maturation markers, and DAPI for viability. The data were analyzed using Flow Jo software. Magnetic resonance imaging (MRI) of lymph nodes in mice: The MRI were preformed using Agilent 7 tesla at TE=30 ms and TR=4,000 ms. NS conjugated with the modified E7 peptides were administered to C57BL/6 mice via subcutaneous injection at tail-base at the iron concentration 50 µg/mouse. The mice were imaged before the NS injection to serve as self-control, at 4 hours, and 24 hours post-injection. Nanoparticle characterizations: Nanoparticles were characterized by transmission electron microscope (TEM) using the solvent evaporation method. Briefly, the solution (5 ILL) of each sample were dropped onto carbon-coated copper TEM grids and allowed to dry overnight. Images were acquired on (TEM, Jeol 1400 plus, 80 kV).

Manufacture of the SatVax nanosatellite vaccine: The iron oxide (IONP) core particles of the nanosatellites were synthesized by thermal decomposition as previously reported[1]. The core particles were subsequently coated by a diblock copolymer (PEO-b-γMPS). Gold sulfide nanoparticles ($Au_2SNP$) were synthesized as previously reported[3]. To produce the nanosatellites (NS), 1 mg Fe of IONP (15 nm) were added into 3 ml of $Au_2SNP$ (2 nm) solution and mixed homogenously incubated on a rocking platform for 30 minutes and stored at 4° C. The nanosatellite solution was filtered by 0.45 µm syringe filler before used. The nanosatellites were characterized by electron microscope (Jeol 1400 plus). Modified E7 peptide (5 mM) was incubated with Acetylthio-PEG5k-Maleimide (2 mM) for 2 hours in endotoxin-free water. The modified E7 peptides conjugated with NS were purified using membrane centrifugation. The flow-through solution was taken to quantify the concentration of the peptide by using LavaPep (Gel company, USA). The E7-NS were then further conjugated with the E6 peptide (0.5 mM) using the same procedure. The final product was purified overnight using a magnet separator. 2'3' cGAMP (14 µM) was added into the peptides-conjugated NS. The final E7 and E6 peptide concentration were 25 µM and 2.5 µM respectively. Hydrodynamic diameters and ζ potential of nanoparticles were measured by dynamic light scattering (DLS) (Malvern Zeta Sizer).

Results

Type I IFN Signaling Promotes HNSCC Sensitivity to Effector Immune Cells

Figure 1A:
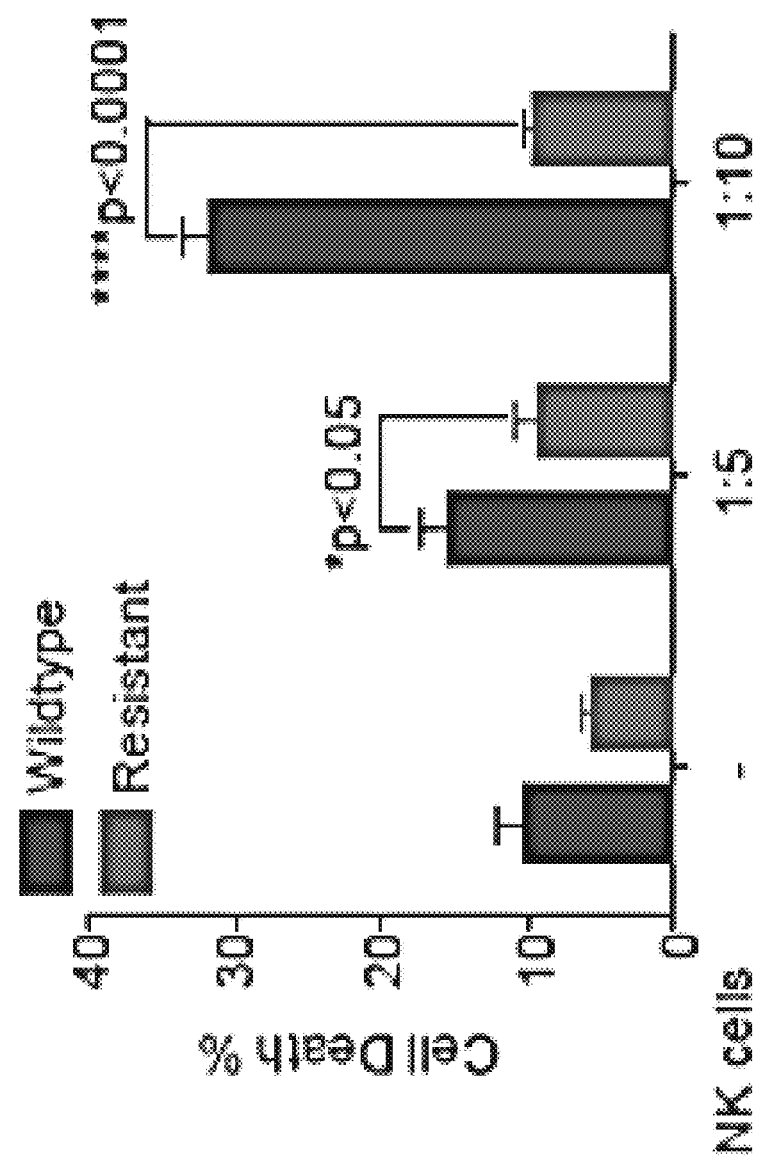
Figure 1B:
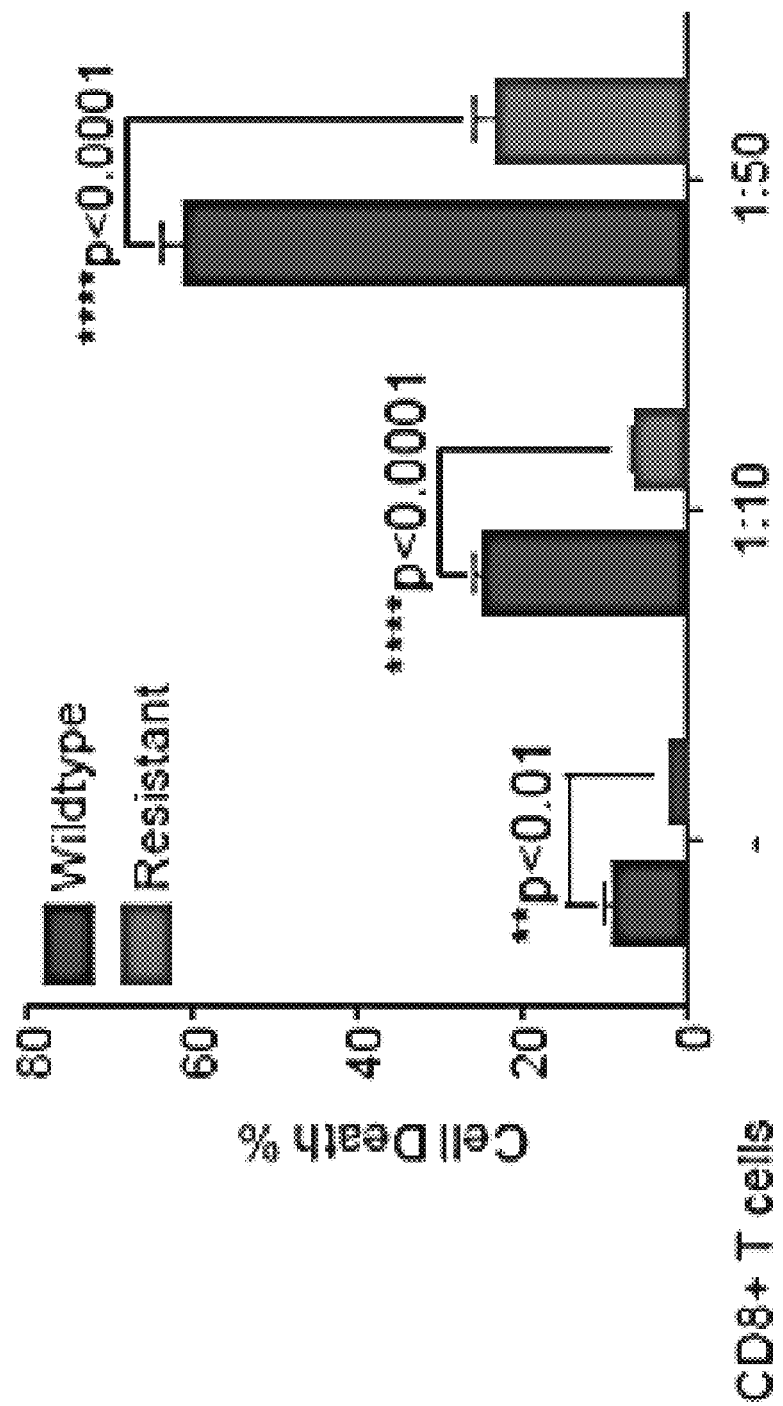
Figure 2A:
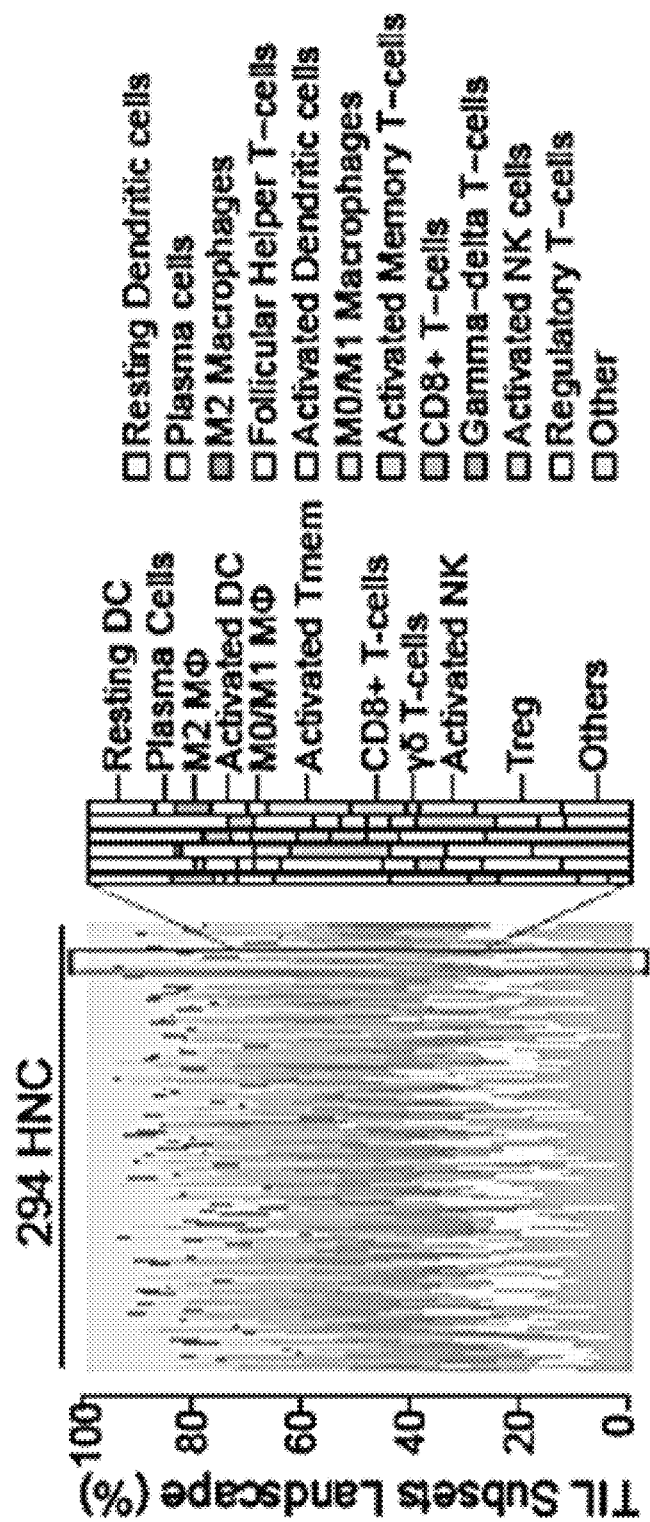
FIGS. 2A-D. Characterization of the HNSCC immune landscape reveals a correlation between type I interferon signatures and key immune cell subsets for anti-tumor immunity. (A) Utilizing a Ci-Seq machine learning tool, the RNA-Seq results of 294 HNSCC specimens were projected into microarray space. Based on the expression profiles of 547 immune cell signature genes, the TIL composition was deconvoluted into 22 subsets to resolve the complete immune landscape. Each vertical color-coded column represents the TIL distribution profile of one HNSCC specimen. Each color represents an immune cell subset. (B) Based on the compositions of each immune cell subsets in 294 primary HNSCC specimens, a marginal correlation was performed between the type I interferon signature genes and the percentages of major immune infiltrate subsets. A positive value indicates positive correlation, and a negative value suggests an inverse relationship. (C) Based on the STING expression levels, Kaplan-Meier survival analysis was performed in 259 HNSCC patients in the TCGA database who are younger than 60 years old. (D) Kaplan-Meier survival analysis was performed in 520 HNSCC patients based on tumor STING expression.
Figure 2B:
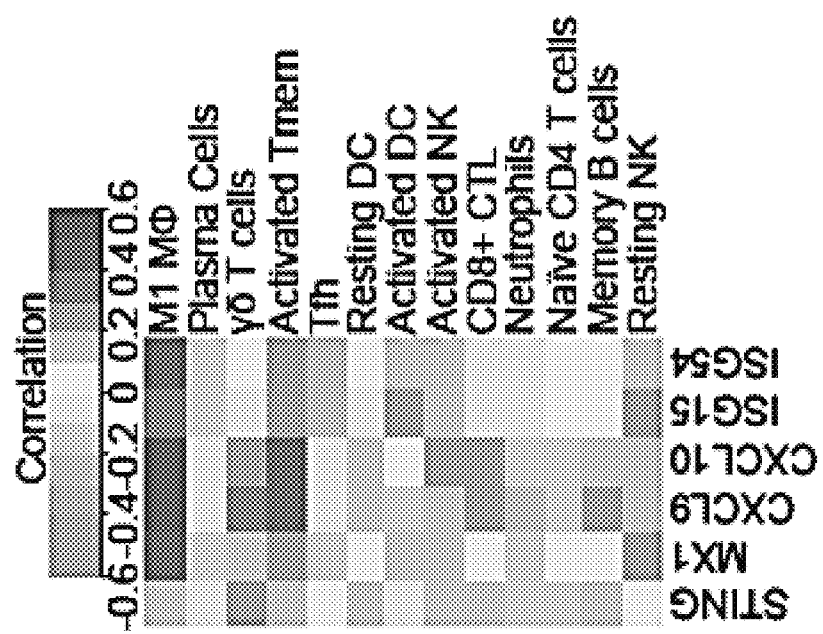
Figure 2C:
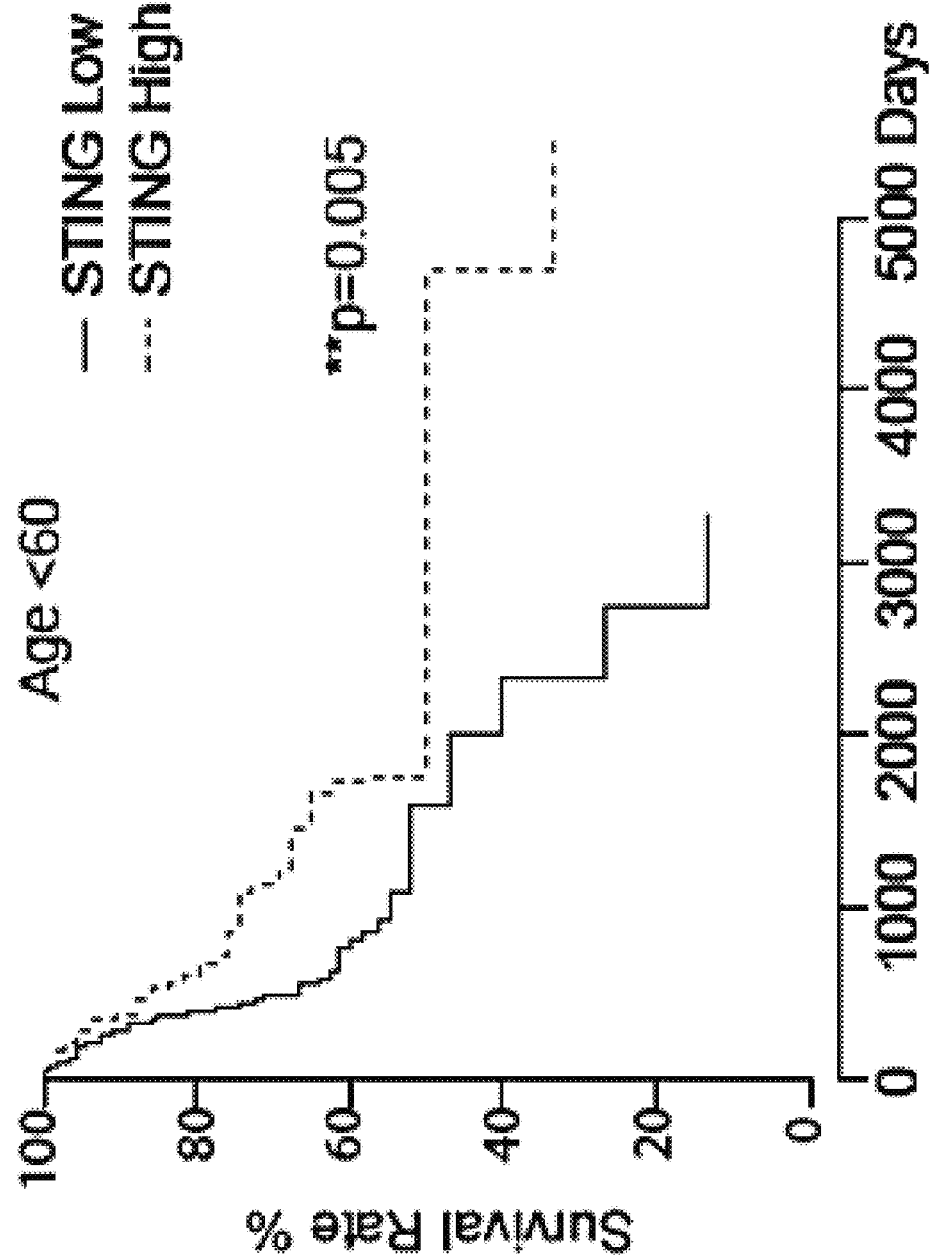
Figure 2D:
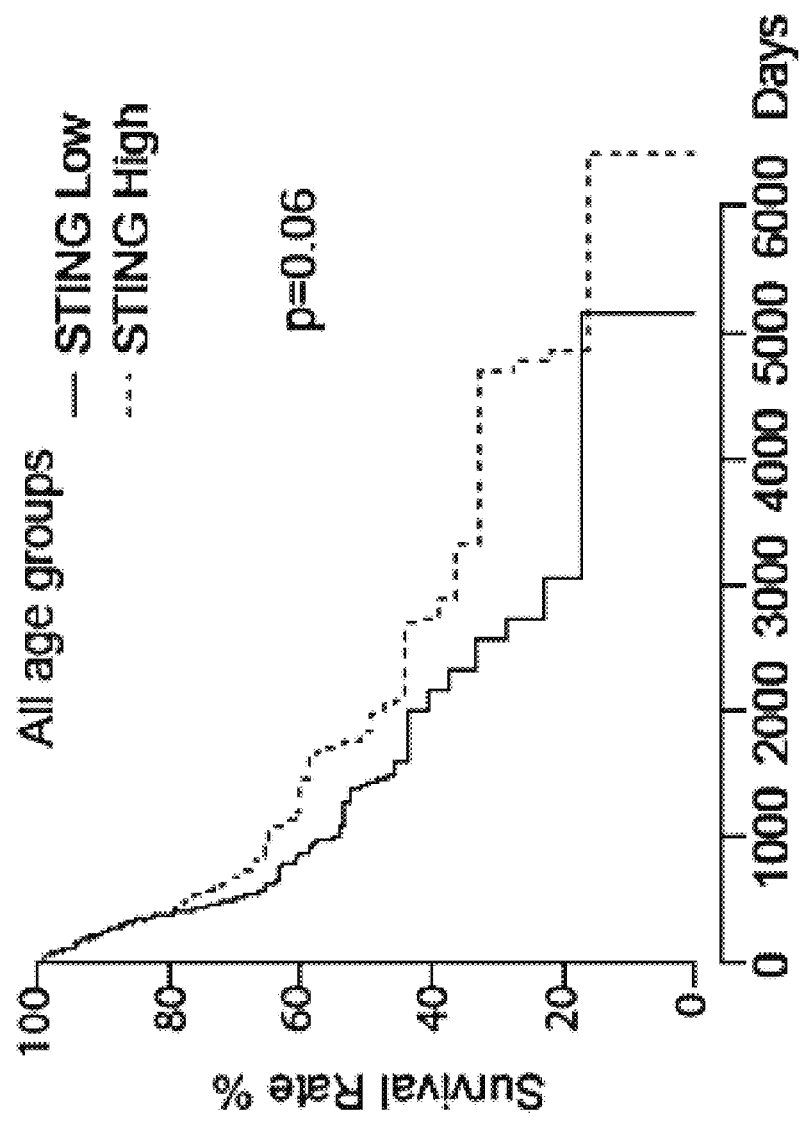

In order to discover pathways promoting cancer cell resistance to effector immune cells, a high throughput screening was employed (FIG. 1). HNSCC cells were repetitively co-cultured with primary human natural killer (NK) cells in the presence of 5 µg/ml cetuximab, an EGFR-targeted antibody that activates antibody-dependent cytotoxicity (ADCC). This dose of cetuximab alone did not demonstrate any cytotoxic effects (Lei et al., 2016a). Dead tumor cells and NK were gently washed off every week, and fresh NK cells were replenished. After HNSCC-NK co-culture was repeated 12 times, it was noticed that these HNSCC cells became resistant when challenged with NK cells at different target:effector (T:E) ratios (FIG. 1A). $CD8^+$ T-cells were separated from a HLA-matched donor, and EGFR-specific CTL were generated. The CTLs were incubated with HNC cells, and it was found that the tumor cells that were resistant to NK cells were also resistant to CTL (FIG. 1B). These findings suggest that tumor cells could employ common signaling pathways to promote resistance to effector immune cells.

An RNA-Seq of the wildtype HNSCC cells and those that were resistant to NK cells and $CD8^+$ CTL was performed. A Gene Set Enrichment Analysis (GESA) identified the central pathways that modulate cancer sensitivity to effector immune cells. Ten of the most significantly altered signaling axes include defense response, cancer cell inflammatory signaling, and cell proliferation and death pathway (q<0.01) (FIG. 1C). The significantly altered genes in immune cell-resistant tumor cells were cross referenced in the Interferome database, which annotates interferon-regulated genes (Rusinova et al., 2013). It was found that the expression profiles of 358 TYPE I INTERFERON-regulated genes were sharply contrasted between wildtype and resistant cells, in the latter of which interferon-stimulated genes (ISGs) were significantly inhibited (FIG. 1D). Among the ISGs were chemokines that recruit immune cells to tumors for APC maturation and cross-priming of $CD8^+$ CTL (Peng et al., 2015; Sistigu et al., 2014; Zitvogel et al., 2015). Multiple proteins that dampen TYPE I INTERFERON signaling, such as NLRX1, NLRC3, and STAT3 (Guo et al., 2016; Lei et al., 2012; Moore et al., 2008; Yang et al., 2015; Zhang et al., 2014), were increased in resistant cells (FIG. 1E). Utilizing real time PCR, the significantly altered expression levels of these key TYPE I INTERFERON-regulatory genes when cancer cells became resistant to immunogenic cytotoxicity were verified (FIG. 1F-K).

TYPE I INTERFERON Signature are Correlated with Effector TIL Populations

To further validate the role of TYPE I INTERFERON signaling in TIL recruitment and differentiation, a novel bioinformatics tool, characterization of immune cell subsets using RNA-Seq data (Ci-Seq) was developed, to deconvolute the immune landscape of human solid tumors. Recent studies have successfully classified immune cells into 22 subsets using 547 signature gene expression profiles on a microarray platform (Gentles et al., 2015; Newman et al., 2015). But most available HNSCC genomic data are generated by deep sequencing. The differentially expressed genes from both data formats are well concordant (Beane et al., 2011; Fu et al., 2009; Guo et al., 2013; Marioni et al., 2008; Nookaew et al., 2012). But the absolute expressions, which are required for deconvolution, between the two platforms are not exchangeable (Uziela and Honkela, 2015). Hence, we leveraged the microarray and RNA-Seq data available for the same specimen that are available through the lung cancer TCGA database, and established the RNA-Seq-microarray projection for the 547 immune cell signature genes as previously validated in microarray format (Gentles et al., 2015). The regression line for each gene was established, utilizing a weighted Support Vector Regression (SVR) model. As an example of the fidelity of the RNA-Seq-to-microarray projection, we showed tight variance due to error for the T-cell subsets markers. Empowered by Ci-Seq, we characterized the immune landscape of 294 HNC specimens, and found that the average percentages of TIL subsets are similar to microarray-based deduction in a pan-cancer study, lending further support to the efficacy of Ci-Seq.

Then we performed marginal correlation between the expression levels of TYPE I INTERFERON signaling genes and the percentages of immune infiltrate subsets. We found that TYPE I INTERFERON signaling genes are positively correlated with populations that are favorably associated with anti-tumor immune response, including M1 macrophages, γδ T cells, memory T cells, and CD8+ CTL. TYPE I INTERFERON signaling is inversely correlated with neutrophils, which were recently identified as a negative prognosticator for patient survival (Gentles et al., 2015). STING-mediated TYPE I INTERFERON activation has been recently shown to promote anti-tumor adaptive immunity in implantable melanoma and sarcoma mouse models (Woo et al., 2014). To understand the prognostic impact of STING on HNSCC patients, we performed Kaplan-Meier analysis based on STING mRNA expression levels. Utilizing the follow-up data in the HNSCC TCGA database, we found that higher STING expression levels are correlated with superior patient survival, especially in younger patients. But STING-mediated TYPE I INTERFERON signaling is often suppressed in cancer cells (Xia et al., 2016), and the mechanisms of suppression remain largely unknown. Hence, we next sought to characterize the regulatory pathway of the STING pathway in HNSCC.

SOX2 Inhibits PRR-Mediated TYPE I INTERFERON Induction

Figure 3A:
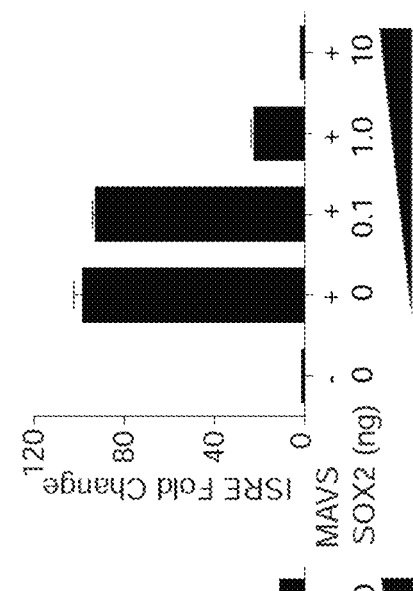
FIGS. 3A-R. SOX2 inhibits intracellular pattern recognition receptor-mediated type I interferon signaling (A-C). HEK-293T cells were transfected with an ISRE luciferase reporter construct and titrating doses of SOX2, in the presence of STING (A), poly(dA:dT) (B), or MAVS (C). ISRE promoter activity was quantitated by luciferase assay. Each condition was performed in triplicates. HEK-293T cells were transfected with 1.0 µg/ml STING expression plasmid with or without SOX2. The transcription levels of IFNB1 (FIG. 3D) and CXCL10 (FIG. 3E) were assessed by real time PCR 16 hrs post-transfection. (F-G) HEK-293T cells were transfected with 1.0 µg/ml poly(dA:dT). RNA was then extracted for IFNB1 (FIG. 3F) and CXCL10 (FIG. 3G) mRNA quantitation. (H-I) UMSCC22b cells were challenged with 1.0 µg/ml STING (FIG. 3H) or poly(dA:dT) (FIG. 3I) in the absence or presence of SOX2 expression. IFNB1 transcription was assessed by real time PCR. (J-K) UMSCC47 cells were challenged with 1.0 µg/ml STING (FIG. 3J) or poly(dA:dT) (FIG. 3K) with or without SOX2. The expression of IFNB1 was measured by real time PCR (L-M). An empty vector control was generated which SOX2-targeted CRISPR-Cas9 lentiviruses. Stable control and SOX2-deficient PCI-13 cells were generated. Then we challenged these cells with the STING agonist cGAMP, IFNB1 (FIG. 3L) and CXCL10 (FIG. 3M) expression levels were measured by real time PCR 16 hrs post-transfection. (N-O) Control and SOX2-deficient PCI-13 cells were challenged with 1.0 µg/ml poly(dA:dT) for 16 hrs. The expression levels of IFNB1 (FIG. 3N) and CXCL10 (FIG. 3O)
Figure 3B:
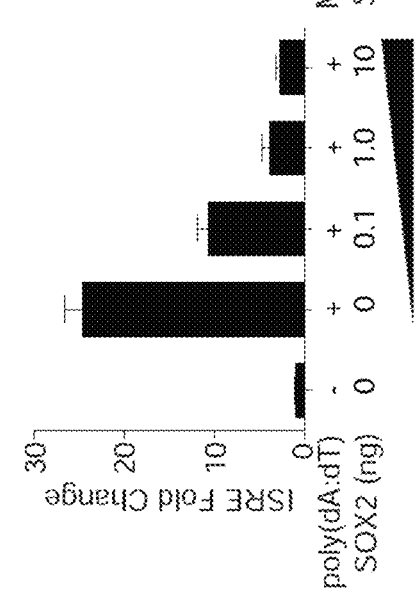
Figure 3C:
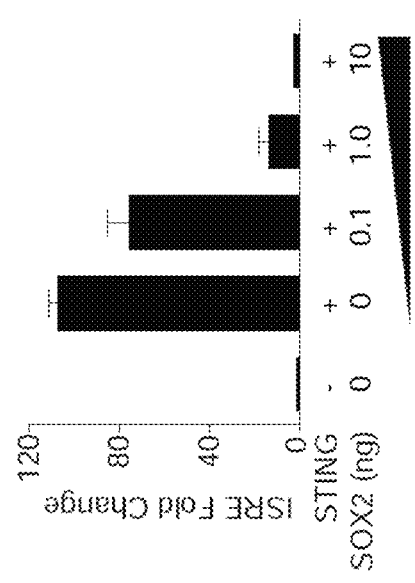

When HNSCC cells became resistant to immunogenic cytotoxicity, a number of well-defined TYPE I INTERFERON-inhibitory proteins were significantly upregulated (FIG. 1E-I). Interestingly, a frequently amplified oncogene in squamous cell carcinomas, SOX2, was also significantly upregulated (FIG. 1E-F). SOX2 promotes the development of squamous cell carcinomas in the skin, lung, GI tract, and head and neck regions (Bass et al., 2009; Boumahdi et al., 2014; Liu et al., 2013; Network, 2015). In conjunction with our findings with other landmark TYPE I INTERFERON regulatory proteins, we next explored whether SOX2 also has a previously unknown function in regulating the inflammatory pathways. Because HNSCC harbors over 300 mutations per cell (Stransky et al., 2011), which might complicate the TYPE I INTERFERON signaling readout, we first used a model cell line HEK293T cells to study the immune-regulating function of SOX2. HEK293T cells were used to identify key TYPE I INTERFERON-inducing adaptors, such as STING and MAVS, and TYPE I INTERFERON-regulatory proteins including NLRX1, NLRC3, and TUFM. We first assessed how SOX2 modulates the PRR-induced ISRE promoter activation. We found that SOX2 expression potently inhibited STING- and B-DNA poly(dA:dT)-induced ISRE promoter activation in a dose-dependent fashion (FIG. 3A-B). In addition, SOX2 also inhibited MAVS-induced ISRE activation (FIG. 3C), suggesting that SOX2 has a broad inhibitory effect on the intracellular PRR-mediated TYPE I INTERFERON signaling. In agreement with promoter activity assays, expression of SOX2 in HEK293T cells potently suppressed STING- and poly(dA:dT)-induced transcription of IFNB1 and an TYPE I INTERFERON-target gene CXCL10 (FIG. 3D-G). We screened a panel of HNSCC cell lines, and found that UMSCC22b and UMSCC47 cells exhibited low endogenous levels of SOX2 expression. Hence, we expressed SOX2 in these two HNSCC cell lines, and recapitulated the findings we observed in HEK-293T cells (FIG. 3H-K). PCI-13 cells exhibited high endogenous level of SOX2 expression. As a confirmatory loss-of-function experiment, we generated a CRISPR-Cas9 lentivirus targeting SOX2, and produced a SOX2-deficient cell line. Consistently, SOX2 deficiency enhanced the transcription of IFNB1 in response to STING and intracellular DNA challenge (FIG. 3L-0).

To confirm the role of SOX2 in TYPE I INTERFERON inhibition, we examined the activation markers of TYPE I INTERFERON using immunoblots. STING potently induced the phosphorylation of TBK1 (S172) and p65 (S536) in HEK-293T, UMSCC22b, and UMSCC47 cells. SOX2 potently suppressed the phosphorylation of TBK1 and p65 (FIG. 3P-R). Interestingly, we noticed that SOX2 decreased the protein level of STING (FIG. 3P-R). STING is a major target for pathogen and cancer to establish immune evasion. STING is a known cargo for autophagosomes, and autophagy promotes the degradation of STING (Konno et al., 2013). Thus we examined whether SOX2 plays a role in autophagy induction as a mechanism of immune inhibition. Overexpression of SOX2 resulted in increased LC3-II/β-actin ratio in the model cell line HEK293T cells. Consistently, SOX2 expression induced more LC3-GFP puncta formation, suggestive of increased basal autophagy. Deficiency in SOX2 resulted in a decreased LC3-II/β-actin ratio, suggesting inhibited autophagic flux. Notably, when HEK-293T and UMSCC22b cells were treated with inhibitors of autophagy, such as chloroquine and bafilomycin A, SOX2-induced decrease in STING protein level was partially restored. This finding suggests that SOX2-mediated autophagy contributes to the degradation of STING, as a mechanism of inhibiting the TYPE I INTERFERON signaling pathway.

Sox2 Promotes Tumor Growth and Inhibits TYPE I INTERFERON Signaling In Vivo

Figure 4B:
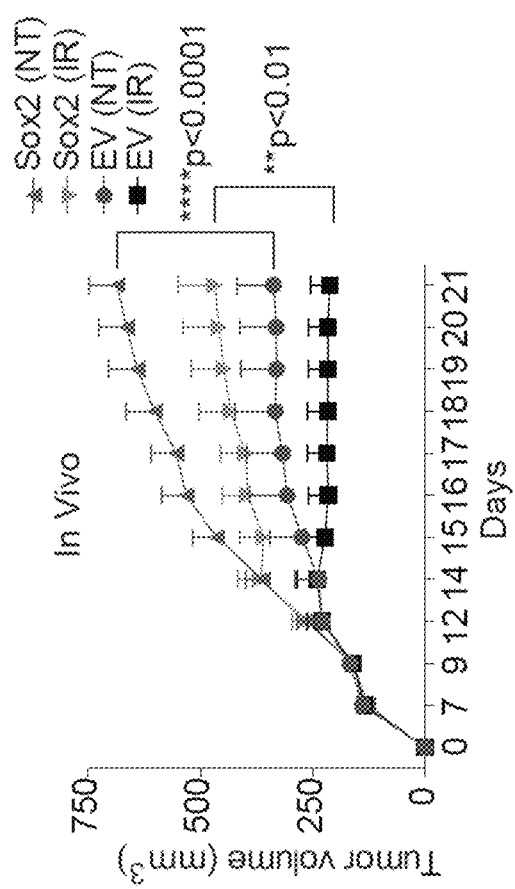
Figure 4A:
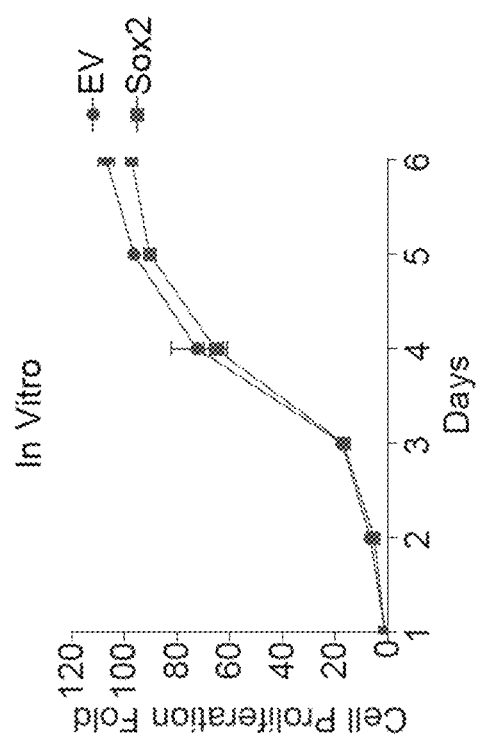

To better understand the role of Sox2 in modulating tumor microenvironment in vivo, we developed a novel HPV16 E6/E7-expressing HNSCC model in immunocompetent hosts. The MOC2 parental cell line exhibits similar molecular mutation profiles as the human HNSCC with a high degree of cross-species conservation (Onken et al., 2014). We produced the MOC2-E6/E7 cell line by transducing the MOC2 cells with a retrovirus expressing HPV16 E6/E7 proteins. MOC2-E6/E7 cells exhibit very low endogenous Sox2 expression. We produced empty vector control and murine Sox2-expressing MOC2-E6/E7 cells using retroviruses. Although the empty vector control and Sox2-expressing tumor cells showed similar proliferation rates in vitro, Sox2-expressing tumor grew significantly faster in C57BL/6 hosts regardless of the ionizing radiation (IR) treatment (FIG. 4A-B). Notably, the immunohistochemical (IHC) examination of these Sox2-positive grafted tumors bear remarkable histologic similarity to human disease (FIG. 4C). In Sox2-positive epithelial malignancies, Sox2 exhibits a diffuse strongly positive nuclear staining pattern (FIG. 4C, lower panels)(Lei et al., 2014). Sox2 exhibits a similar staining pattern in our mouse model (FIG. 4C, top panels).

To further examine how Sox2 affects tumor microenvironment, we homogenized the tumor specimens from empty vector and Sox2-expressing groups, and extracted RNA for real time PCR quantitation of the TYPE I INTERFERON signature gene transcripts. Although IR could induce TYPE I INTERFERON signaling in the MC38 colon adenocarcinoma model (Deng et al., 2014), HPV E6/E7 potently inhibits the STING pathway (Lau et al., 2015). In fact, IR did not upregulate TYPE I INTERFERON signatures in this E6/E7-expressing squamous cell carcinoma model (FIG. 4D-H). Regardless of the IR treatment, Sox2 significantly decreased the transcription of classic TYPE I INTERFERON signature genes, including Cxcl9, Cxcl10, and Mx1 (FIG. 4D-F). As a maker of effector immune cell activation in the microenvironment, the transcription of Ifng was also significantly suppressed in Sox2-expressing tumors (FIG. 4G). In agreement, IHC assessment of the tumors showed that the Mx1 expression levels were reduced in Sox2-expressing tumors. As another approach to assess TYPE I INTERFERON signaling, we found that the phosphorylation of Tbk1 and p65 in Sox2-positive tumors were lower than those in the control tumors, lending further support to the immune-inhibitory role of Sox2.

Figure 4J:
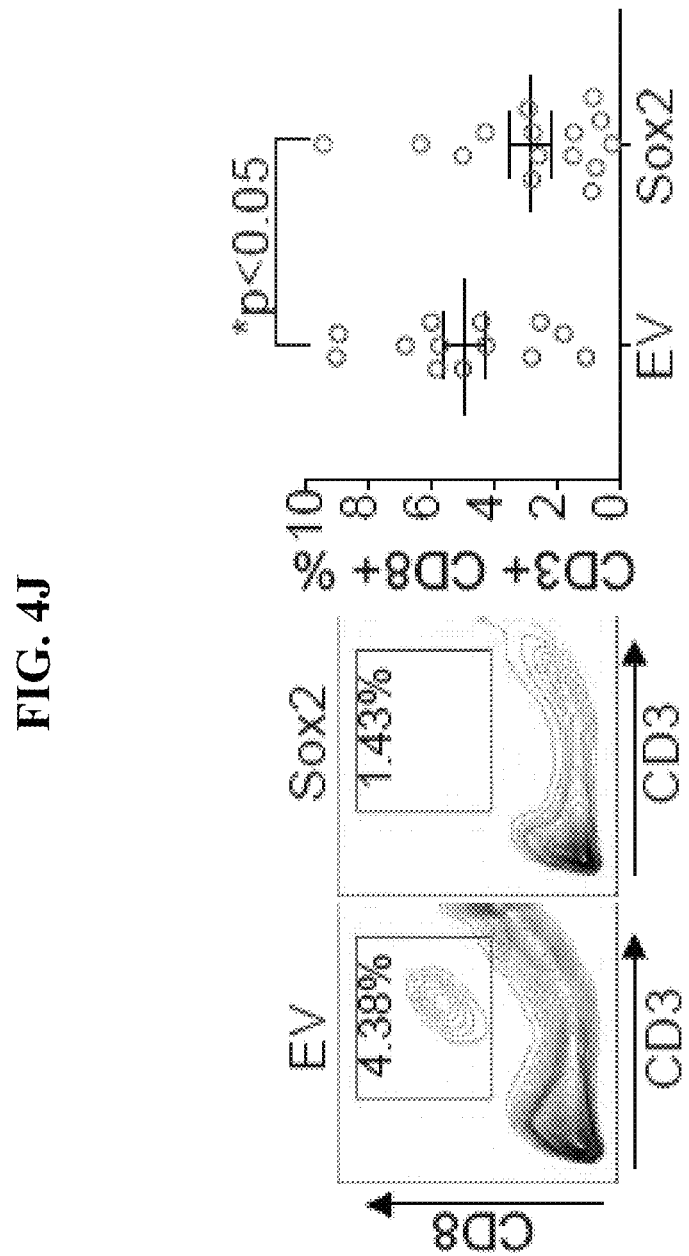
Figure 4K:
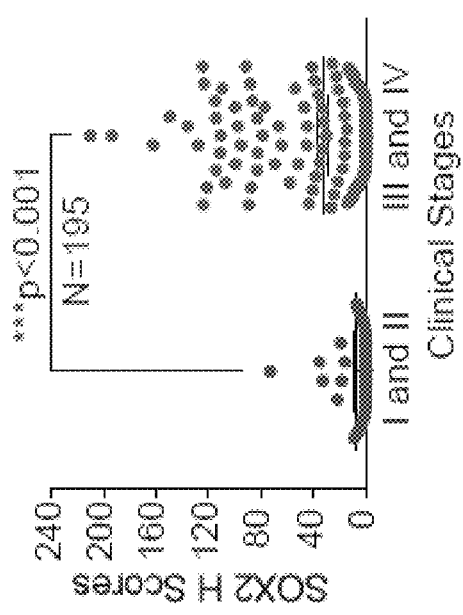
Figure 4L:
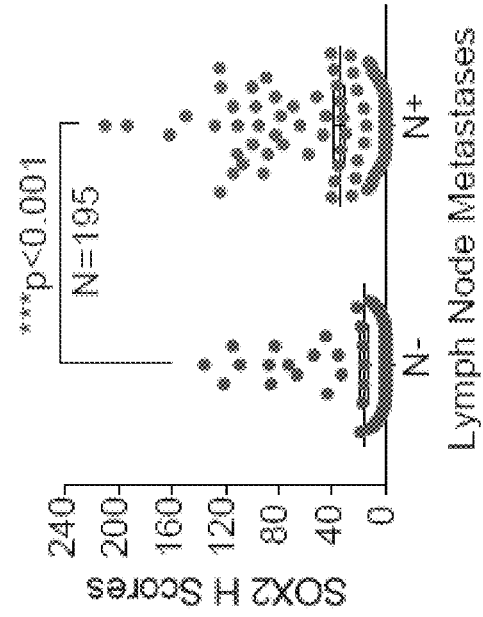

To assess the impact of suppressed TYPE I INTERFERON signaling on TIL recruitment, we purified TILs through Ficoll-Paque gradient. This syngeneic model bears similarity in its immune microenvironment. In agreement with findings we made with primary human HNSCC specimens (Li et al., 2015), we found that the CD8$^+$ T cells in the TILs contain a significantly higher PD-1 population than the periphery, suggesting a state of exhaustion (Figure S4). Notably, the infiltration of CD3$^+$ CD8$^+$ T cells was significantly inhibited in Sox2-positive tumors (FIG. 4J). To better understand the impact of SOX2 expression in human disease, we generated a tissue microarray (TMA), which contains 218 primary HNSCC specimens. We scored the SOX2 IHC staining using Aperio ImageScope in tumor cells, and found that SOX2 expression levels were significantly higher in patients with advanced stage disease (FIG. 4K). SOX2-high tumors were also correlated with increased lymph node metastasis (FIG. 4L).

Nanosatellites (NS) Enhance the Potency of STING Agonist

Based on our results, we reasoned that decreased TYPE I INTERFERON signaling in the tumor microenvironment hampers the recruitment and maturation of APC, which in turn limits its antigen processing, maturation, and cross-priming functions. For the sake of restoring APC function and delivering high-density tumor-specific antigens, we developed a novel NS-based vaccine SatVax. SatVax was engineered to promote the intracellular delivery of the STING agonist cGAMP as an adjuvant, with enhanced surface area for antigen conjugation. NS features a biodegradable polysiloxane-containing polymer-coated iron oxide core (IONP) with inert gold (Au) satellites (FIG. 5A). Nanoparticles of about 50 nm in size exhibit the best uptake efficiency (Chithrani et al., 2006). Our NS vehicles measured 50.75 nm, and conjugation with peptides and adjuvant did not change its size (FIG. 5B). The NS delivery system significantly promoted cGAMP-induced ISRE activity in a monocytic cell line THP-1 cells (FIG. 5C). In agreement, NS promoted the cGAMP intracellular delivery and efficacy, as evidenced by significantly higher mRNA levels of IFNA4, IFNB1, ISG15, ISG54, CXCL9, and CXCL10 in the presence of NS vehicles (FIG. 5D-I). In the full vaccine formulation, cGAMP was condensed onto the antigenic peptides. To directly measure the intracellular uptake of the vaccine components, we labeled the antigenic peptides with a FAM fluorophore. We found that NS significantly promoted the intracellular uptake of the vaccine components (FIG. 5J). As a result, when we challenged primary bone marrow-derived dendritic cells with cGAMP in the absence or presence of NS, the full vaccine (SatVax) formulation significantly promoted the expression levels of MHC Class II molecule and CD86, suggesting increased APC maturation (FIG. 5K-L).

The Nanosatellite Vaccine SatVax Improves E7-Specific Anti-Tumor Immunity

Cold tumors attract insufficient APC to process tumor antigens, leading to dampened adaptive immunity. To determine whether SatVax could accumulate in the lymph nodes to stimulate APC, we first performed an MRI imaging after vaccine administration. Due to the biocompatible IONP core, we were able to visualize the distribution of SatVax. We found that SatVax rapidly accumulated in the inguinal and popliteal lymph nodes after subcutaneous injections (FIG. 6A). In our initial formulation, we included two antigenic peptides, one of which is a 9 amino acids core epitope of E7 (R9F). By administering three weekly doses of SatVax subcutaneously, we significantly reduced tumor burden in C57BL/6 hosts (FIG. 6B). After the tumors were harvested 25 days post-implantation, RNA was extracted to examine TYPE I INTERFERON transcription. In agreement with our in vitro findings, SatVax (R9F, Q15L) potently promoted the production of Ifna4 and Ifnb1 (FIG. 6C). In contrast, cGAMP alone showed modest effect at this late time point, probably due to the rapid degradation of cGAMP in vivo (FIG. 6C). To validate whether SatVax stimulated the production of TA-specific CTL, we harvested the tumors and extracted TILs through Ficoll-Paque gradient. The TILs were then stained with a tetramer recognizing H-2D$^b$-restricted HPV16 E7 epitope RAHYNIVTF (SEQ ID NO:33). SatVax-treated group showed significantly higher percentages of TA-specific CD8$^+$ CTL, lending further support to the immune-stimulatory efficacy of SatVax (FIG. 6C).

SatVax Extends Host Survival and Mitigates Sox2-Mediated Immune Suppression

As longer peptide may further increase cGAMP condensation and protect the core epitope from rapid degradation. We next designed a SatVax formulation that contains E6 Q15L and a longer E7 peptide Q19D, which was used in HPV vaccines. Three weekly doses were injected subcutaneously with the first dose given 3 days post-tumor implantation. The same amount of peptides or cGAMP as in the vaccine and 6 doses of 100 μg intraperitoneal injections of a benchmark immunotherapeutic agent anti-PD-L1 were given as controls. We found that SatVax exhibited superior therapeutic efficacy to that of anti-PD-L1 and cGAMP (FIG. 7A). SatVax significantly extended host survival due to significantly reduced tumor burden (FIG. 7B). In agreement, SatVax exhibited the best TYPE I INTERFERON induction capability, as shown by the transcription of Ifna4 and Ifnb1 (FIG. 7C-D). Flow cytometric analysis of TILs showed that SatVax potently induced E7-specific CD8$^+$ CTL, contributing to its therapeutic efficacy (FIG. 7E).

The CD8$^+$ CTL in the tumor microenvironment exhibit a significantly higher expression level of PD-1. To prevent vaccine-induced effector T cells rapidly entering into exhaustion, we combined SatVax (Q19D, Q15L) with anti-PD-L1 to tackle Sox2-positive tumors (FIGS. 7 and 8), which showed a more aggressive growth behavior (FIG. 4B). Due to the rapid tumor growth, we reduced cell number than we used in FIG. 4B to prevent mouse deaths prior to completion of the treatment regimen shown in FIG. 8. We found that vaccine and anti-PD-L1 delivered significant protection when used alone. A combination of both treatments demonstrated superior efficacy to single agent. In fact, 4 of 5 mice did not have any measurable tumors until Day 18 post-tumor implantation in the combination group (FIG. 7F).

Squamous cell carcinomas are in general much less immunogenic than melanomas. Only 13.3% of the HNSCC patients responded to anti-PD-1 in a randomized phase 3 clinical trial (Ferris et al., 2016); while 74% of the melanoma patients showed response to anti-PD-1 (Ribas et al., 2016). But our understanding of the mechanism underpinning the hypoimmunogenicity of squamous cell carcinomas remains very limited. In the melanoma model, a defect in IFN-γ signaling was associated with resistance to PD-LU: PD-1 blockade (Gao et al., 2016; Zaretsky et al., 2016). Effector immune cell-mediated IFN-γ signaling is preceded by proper tumor-homing and maturation of APC, which requires the expression of TYPE I INTERFERON signatures. In this example, we identified type I IFN signaling as a pivotal pathway modulating the immunogenicity of HNSCC (FIGS. 1-2).

We characterized how a frequently amplified oncogene in squamous cell carcinoma, SOX2, potentiates tumor immune suppression by targeting the STING-mediated TYPE I INTERFERON activation (FIGS. 3-4). Sox2 coordinates with environmentally activated Stat3 to promote the development of squamous cell carcinoma (Liu et al., 2013). The SOX2 locus is significantly amplified in squamous cell carcinomas of the skin, lung, GI tract, and head and neck (Bass et al., 2009; Boumahdi et al., 2014; Chou et al., 2013; Network, 2015; Rudin et al., 2012; Siegle et al., 2014). SOX2 has a known function promoting cancer "stemness". Cancer stem cells are more resistant to chemoradiotherapy, and exhibit immunosuppressive effect in multiple models. This study reveals a previously unknown mechanistic link between SOX2 and an immunosuppressive tumor microenvironment. Previous studies suggests that autophagy serves as a critical checkpoint for TYPE I INTERFERON activation (Jounai et al., 2007; Lei et al., 2012; Virgin and Levine, 2009). The cGAS-STING DNA sensing pathway has been identified as cargos for autophagosomes (Konno et al., 2013; Saitoh et al., 2009). We found that SOX2 potently promotes autophagy, inhibition of which partially restores STING expression. These results revealed a critical new pathway that modulates the immunogenicity of HNSCC.

In order to restore tumor antigen-specific immunity against hypoimmunogenic tumors, we engineered a novel nanosatellite vaccine system that significantly enhances TYPE I INTERFERON signaling and delivers tumor antigens. We have shown that the nanosatellite vaccine SatVax significantly potentiates the potency of the STING agonist and increases antigen intracellular uptake (FIG. 5). The vaccine rapidly accumulates in the lymph node, and delivers superior protection than anti-PD-L1 alone (FIGS. 6-7). It significantly expanded the pool of tumor antigen-specific CD8+ CTL in the tumor microenvironment (FIGS. 6-7). In agreement with human HNSCC, CD8+ CTL in the tumors expresses higher levels of PD-1, suggesting a state of exhaustion (Li et al., 2015). The combination of anti-PD-L1 with SatVax demonstrates superior efficacy to single treatment against Sox2-expressing HNSCC (FIG. 7).

Two major classes of therapeutic vaccines against HNSCC have been reported, including dendritic cell vaccine and pathogen-based vaccine systems. A unique strength of the nanoparticle-based delivery system is its consistent engineering quality control and outstanding biosafety profile. In addition, although our prototype SatVax is bivalent targeting two tumor antigen peptides, this system is amenable to incorporate any antigen (e.g., neoantigen peptides) to further expand the CD8+ CTL repertoire. Higher nonsynonymous mutation load is shown to correlated with better clinical response to checkpoint inhibitors (Rizvi et al., 2015), suggesting approaches to enhance neoantigen-targeted adaptive immunity holds promise to overcome cancer resistance to PD-L1:PD-1 blockade. With the availability of low-cost next-gen sequencing and bioinformatics prediction tools for neoantigen identification, our nanosatellite vaccine delivery system offers a novel approach to personalized immunotherapeutic regimen that aims to expand the responders to checkpoint blockade.

In summary, this study identifies TYPE I INTERFERON signaling as a central mechanism regulating HNSCC immunogenicity. We generated a new bioinformatics tool Ci-Seq to annotate the immune landscape of solid tumors using RNA-Seq data. We found that TYPE I INTERFERON signaling is associated with immune populations essential for anti-tumor adaptive immunity. We discovered SOX2 oncogenic signaling as a novel axis that inhibits TYPE I INTERFERON induction and promotes an immunosuppressive microenvironment. We engineered a nanosatellite-based TYPE I INTERFERON-inducing vaccine, SatVax, which potently promoted tumor antigen-specific immunity and broadly protect hosts against Sox2-negative and Sox2-positive tumors. A combination of SatVax with checkpoint blockade demonstrates superior therapeutic efficacy. These results represent a conceptual and technological advance in new treatment strategies for hypoimmunogenic tumors or other tumors.

Example 2

Human Serum Albumin Delivery of Peptide

Human serum albumin (HSA) was also used to replace core satellite nanoparticle for vaccine application. To formulate HSA-based vaccine, we first modify HSA with E6 peptide through a heterobiofunctional PEG linker (Maleimide PEG Succinimidyl NHS acid ester) and then stack adjuvant cGAMP through electrostatic interaction in PBS buffer at pH 7.2.

The following detail steps are described as one example. Two hundred micro liter of HSA (1.0 mg/mL in PBS, pH: 7.2) was mixed with 200 µL of PEG linker solution (Mw: 5000 Dalton, 1.0 mg/mL in PBS, pH: 7.2) and incubated at room temperature for 1.5 hrs. The free PEG linker molecules were removed through ultracentrifugation with a filter membrane cut-off at 10k. Four hundred micro Liter of PBS was used to re-suspend the pellet and further react with 20 µL of thiolated E6 peptide solution (10 mg/mL in PBS, pH: 7.2) under mechanical stirring at 4° C. overnight in the dark. The resultant solution was filtered with the same condition and 300 µL of PBS was used to re-suspend the pellet and then mixed with 200 µL of cGAMP (1.0 mg/mL in PBS). The resultant solution will be stored in 4° C. for future use without further purification.

The resulting HSA-peptide-cGAMP complexes were tested as described below and the results are shown in FIGS. 12 and 13. For analysis of mRNA in THP1-blue ISG cells, cells were seeded at one million cells/well in a 6-well plate. The cells were treated 16 hours with either media, Au alone, Au-cGAMP, HSA alone, HSA-peptide-cGAMP, and 2'3'-cGAMP alone (10 ug/ml final concentration). Total RNA was isolated from cells using the QIAshredder and RNeasy Plus mini. RNA was quantitated using Nanodrop, and reverse transcription was performed using High-Capacity RNA-to-cDNA kit. For real-time PCR, the cDNA was diluted and reactions were set up using the PowerUp SYBR Green Master Mix and ran on 7900HT Fast Real-Time PCR System. All data were analyzed using the comparative CT method, and normalized to the corresponding HPRT mRNA levels. The primers used were as follows: CXCL9F 5'-GTGGTGTTCTTTCCTCTTGGG-3' (SEQ ID NO:34), R 5'-ACAGCGACCCTTTCTCACTAC-3' (SEQ ID NO:35); CXCL10 F 5'-CTCCAGTCTCAGCACCATGA (SEQ ID NO:36), R 5'-GCTCCCCTCTGGTTTTAAGG (SEQ ID NO:37); HPRT1 F 5'-ATGCTGAGGATTTGGAAAGG (SEQ ID NO:40), R 5'-CAGAGGGCTACAATGTGATGG-3' (SEQ ID NO:38).

In FIGS. 12 and 13, Au refers to gold nanoparticles and HSA refers to the HSA-peptide-cGAMP complex. We used Au to compare with HSA in order to demonstrate the advantages of the HSA carrier. Au is a general nanoparticle control. As you can see that HSA formulation promotes higher level of cxcl10 and cxcl9 than Au formulation. The level of mRNA treated by Au formulation is not different from cGAMP in PBS solution. FIG. 12 shows that the HSA-peptide-cGAMP complex resulted in higher CXCL10 mRNA expression in THP1-blue ISG cells compared to control, while FIG. 13 shows that the HSA-peptide-cGAMP complex resulted in higher CXCL9 mRNA expression in THP1-blue ISG cells compared to control.

REFERENCES

Ahn, J., and Barber, G. N. (2014). Self-DNA, STING-dependent signaling and the origins of autoinflammatory disease. Current opinion in immunology 31, 121-126.

Barber, G. N. (2015). STING: infection, inflammation and cancer. Nature reviews 15, 760-770.

Bass et al. (2009). SOX2 is an amplified lineage-survival oncogene in lung and esophageal squamous cell carcinomas. Nature genetics 41, 1238-1242.

Beane et al. (2011). Characterizing the impact of smoking and lung cancer on the airway transcriptome using RNA-Seq. Cancer Prev Res (Phila) 4, 803-817.

Boumahdi et al. (2014). SOX2 controls tumour initiation and cancer stem-cell functions in squamous-cell carcinoma. Nature 511, 246-250.

Bullock, et al., (2003). Antigen density presented by dendritic cells in vivo differentially affects the number and avidity of primary, memory, and recall CD8+ T cells. J Immunol 170, 1822-1829.

Chithrani et al., (2006). Determining the size and shape dependence of gold nanoparticle uptake into mammalian cells. Nano Lett 6, 662-668.

Chou, et al. (2013). The emerging role of SOX2 in cell proliferation and survival and its crosstalk with oncogenic signaling in lung cancer. Stem cells.

Corrales et al., (2016). The host STING pathway at the interface of cancer and immunity. The Journal of clinical investigation 126, 2404-2411.

Deng, L. et al. (2014). STING-Dependent Cytosolic DNA Sensing Promotes Radiation-Induced Type I Interferon-Dependent Antitumor Immunity in Immunogenic Tumors. Immunity 41, 843-852.

Ferris et al. (2016). Nivolumab for Recurrent Squamous-Cell Carcinoma of the Head and Neck. The New England journal of medicine 375, 1856-1867.

Fu J. et al., (2015). STING agonist formulated cancer vaccines can cure established tumors resistant to PD-1 blockade. Sci Transl Med 7, 283ra252.

Fu et al., (2009). Estimating accuracy of RNA-Seq and microarrays with proteomics. BMC Genomics 10, 161.

Gao et al. (2016). Loss of IFN-gamma Pathway Genes in Tumor Cells as a Mechanism of Resistance to Anti-CTLA-4 Therapy. Cell 167, 397-404 e399.

Gentles et al., (2015). The prognostic landscape of genes and infiltrating immune cells across human cancers. Nature medicine 21, 938-945.

Guo et al. (2016). NLRX1 Sequesters STING to Negatively Regulate the Interferon Response, Thereby Facilitating the Replication of HIV-1 and DNA Viruses. Cell host & microbe 19, 515-528.

Guo et al., (2013). Large scale comparison of gene expression levels by microarrays and RNAseq using TCGA data. PloS one 8, e71462.

Herbst et al. (2014). Predictive correlates of response to the anti-PD-L1 antibody MPDL3280A in cancer patients. Nature 515, 563-567.

Ishikawa, H., and Barber, G. N. (2008). STING is an endoplasmic reticulum adaptor that facilitates innate immune signalling. Nature 455, 674-678.

Ishikawa et al., (2009). STING regulates intracellular DNA-mediated, type I interferon-dependent innate immunity. Nature 461, 788-792.

Jounai et al., (2007). The Atg5 Atg12 conjugate associates with innate antiviral immune responses. Proceedings of the National Academy of Sciences of the United States of America 104, 14050-14055.

Konno et al., (2013). Cyclic Dinucleotides Trigger ULK1 (ATG1) Phosphorylation of STING to Prevent Sustained Innate Immune Signaling. Cell 155, 688-698.

Lau et al., (2015). DNA tumor virus oncogenes antagonize the cGAS-STING DNA-sensing pathway. Science (New York, N.Y. 350, 568-571.

Lei et al., (2014). Evaluation of SOX2 as a potential marker for ameloblastic carcinoma. Oral Surg Oral Med Oral Pathol Oral Radiol 117, 608-616 e601.

Lei et al., (2016a). EGFR-targeted mAb therapy modulates autophagy in head and neck squamous cell carcinoma through NLRX1-TUFM protein complex. Oncogene.

Lei et al. (2012). The mitochondrial proteins NLRX1 and TUFM form a complex that regulates type I interferon and autophagy. Immunity 36, 933-946.

Lei et al., (2016b). Telltale tumor infiltrating lymphocytes (TIL) in oral, head & neck cancer. Oral oncology.

Li, B., and Dewey, C. N. (2011). RSEM: accurate transcript quantification from RNA-Seq data with or without a reference genome. BMC Bioinformatics 12, 323.

Li et al., (2015). PD-1/SHP-2 inhibits Tc1/Th1 phenotypic responses and the activation of T cells in the tumor microenvironment. Cancer research 75, 508-518.

Liu et al. (2013). Sox2 cooperates with inflammation-mediated Stat3 activation in the malignant transformation of foregut basal progenitor cells. Cell stem cell 12, 304-315.

Marioni et al., (2008). RNA-seq: an assessment of technical reproducibility and comparison with gene expression arrays. Genome Res 18, 1509-1517.

Marur et al., (2010). HPV-associated head and neck cancer: a virus-related cancer epidemic. The lancet oncology 11, 781-789.

Moore et al. (2008). NLRX1 is a regulator of mitochondrial antiviral immunity. Nature 451, 573-577.

Moroishi et al., (2016). The Hippo Pathway Kinases LATS1/2 Suppress Cancer Immunity. Cell 167, 1525-1539 e1517.

Network, C. G. A. (2015). Comprehensive genomic characterization of head and neck squamous cell carcinomas. Nature 517, 576-582.

Newman et al., (2015). Robust enumeration of cell subsets from tissue expression profiles. Nat Methods 12, 453-457.

Nguyen, L. T., and Ohashi, P. S. (2015). Clinical blockade of PD1 and LAG3-potential mechanisms of action. Nature reviews 15, 45-56.

Nookaew et al., (2012). A comprehensive comparison of RNA-Seq-based transcriptome analysis from reads to differential gene expression and cross-comparison with microarrays: a case study in *Saccharomyces cerevisiae*. Nucleic acids research 40, 10084-10097.

Onken et al. (2014). A surprising cross-species conservation in the genomic landscape of mouse and human oral cancer identifies a transcriptional signature predicting metastatic disease. Clin Cancer Res 20, 2873-2884.

Peng et al. (2015). Epigenetic silencing of TH1-type chemokines shapes tumour immunity and immunotherapy. Nature 527, 249-253.

Ribas et al. (2016). Association of Pembrolizumab With Tumor Response and Survival Among Patients With Advanced Melanoma. JAMA 315, 1600-1609.

Rizvi et al. (2015). Cancer immunology. Mutational landscape determines sensitivity to PD-1 blockade in non-small cell lung cancer. Science (New York, N.Y. 348, 124-128.

Robinson, M. D., McCarthy, D. J., and Smyth, G. K. (2010). edgeR: a Bioconductor package for differential expression analysis of digital gene expression data. Bioinformatics 26, 139-140.

Rudin et al. (2012). Comprehensive genomic analysis identifies SOX2 as a frequently amplified gene in small-cell lung cancer. Nature genetics 44, 1111-1116.

Rusinova et al., (2013). Interferome v2.0: an updated database of annotated interferon-regulated genes. Nucleic acids research 41, D1040-1046.

Saitoh et al. (2009). Atg9a controls dsDNA-driven dynamic translocation of STING and the innate immune response. Proceedings of the National Academy of Sciences of the United States of America 106, 20842-20846.

Schreiber et al., (2011). Cancer immunoediting: integrating immunity's roles in cancer suppression and promotion. Science (New York, N.Y. 331, 1565-1570.

Seth et al., (2005). Identification and characterization of MAVS, a mitochondrial antiviral signaling protein that activates NF-kappaB and IRF 3. Cell 122, 669-682.

Siegle et al. (2014). SOX2 is a cancer-specific regulator of tumour initiating potential in cutaneous squamous cell carcinoma Nat Commun 5, 4511.

Silva et al. (2014). Development of functionalized nanoparticles for vaccine delivery to dendritic cells: a mechanistic approach. Nanomedicine (Lond) 9, 2639-2656.

Sistigu et al. (2014). Cancer cell-autonomous contribution of type I interferon signaling to the efficacy of chemotherapy. Nature medicine 20, 1301-1309.

Starr, P. (2015). Encouraging Results for Pembrolizumab in Head and Neck Cancer. Am Health Drug Benefits 8, 16.

Stransky et al. (2011). The mutational landscape of head and neck squamous cell carcinoma. Science (New York, N.Y. 333, 1157-1160.

Subramanian et al., (2005). Gene set enrichment analysis: a knowledge-based approach for interpreting genome-wide expression profiles. Proceedings of the National Academy of Sciences of the United States of America 102, 15545-15550.

Sun et al., (2013). Cyclic GMP-AMP synthase is a cytosolic DNA sensor that activates the type I interferon pathway. Science (New York, N.Y. 339, 786-791.

Uziela, K., and Honkela, A. (2015). Probe Region Expression Estimation for RNA-Seq Data for Improved Microarray Comparability. PloS one 10, e0126545.

Virgin, H. W., and Levine, B. (2009). Autophagy genes in immunity. Nature immunology 10, 461-470.

Wang et al. (2010). MapSplice: accurate mapping of RNA-seq reads for splice junction discovery. Nucleic acids research 38, e178.

Woo et al., (2015a). Innate immune recognition of cancer. Annual review of immunology 33, 445-474.

Woo et al., (2015b). The STING pathway and the T cell-inflamed tumor microenvironment. Trends in immunology 36, 250-256.

Woo et al. (2014). STING-dependent cytosolic DNA sensing mediates innate immune recognition of immunogenic tumors. Immunity 41, 830-842.

Wu et al., (2013). Cyclic GMP-AMP is an endogenous second messenger in innate immune signaling by cytosolic DNA. Science (New York, N.Y. 339, 826-830.

Xia et al., (2016). Deregulation of STING Signaling in Colorectal Carcinoma Constrains DNA Damage Responses and Correlates With Tumorigenesis. Cell Rep 14, 282-297.

Yang et al., (2015). STAT3 Inhibition Enhances the Therapeutic Efficacy of Immunogenic Chemotherapy by Stimulating Type 1 Interferon Production by Cancer Cells. Cancer research 75, 3812-3822.

Zaretsky et al. (2016). Mutations Associated with Acquired Resistance to PD-1 Blockade in Melanoma. The New England journal of medicine 375, 819-829.

Zhang et al. (2014). NLRC3, a member of the NLR family of proteins, is a negative regulator of innate immune signaling induced by the DNA sensor STING. Immunity 40, 329-341.

Zitvogel et al., (2015). Type I interferons in anticancer immunity. Nature reviews 15, 405-414.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of treating head and neck squamous cell carcinoma (HNSCC) in a subject comprising: administering to a subject having at least one HNSCC tumor:
   a) a composition comprising a nano-satellite complex, wherein said nano-satellite complex comprises:
      i) a core nanoparticle complex comprising a biocompatible coating surrounding a nanoparticle core;
      ii) at least one satellite particle attached to, or absorbed to, said biocompatible coating;
      iii) an antigenic component conjugated to, or absorbed to, said at least one satellite particle component, wherein said antigenic component comprises an antigenic peptide, wherein said antigenic peptide comprises at least one epitope from a viral oncoprotein; and
      iv) a type I interferon agonist agent which is electrostatically attracted to, or absorbed to, said antigenic component; and
   b) an immune checkpoint inhibitor.

2. The method of claim 1, wherein said nanoparticle core comprises Fe3O4, said biocompatible coating comprises polysiloxane, and said at least one satellite particle comprises a plurality of satellite particles composed of gold.

3. The method of claim 1, wherein said type I interferon agonist agent is selected from the group consisting of: c-di-GMP, c-di-AMP, cGAMP, c-di-IMP, c-di-UMP, 5,6-dimethylxanthenone-4-acetic acid (DMXAA), 2'3'-cGAM (PS)2 (Rp/Sp), 2'3'-c-di-AM(PS)2 (Rp,Rp), and a STING agonist.

4. The method of claim 1, wherein said at least one tumor comprises a plurality of HNSCC cancer cells, and wherein said administering kills at least some of said plurality of HNSCC cancer cells.

5. The method of claim 1, wherein said subject is a human.

6. The method of claim 1, wherein said administering generates an immune response in said subject making them resistant to infection by infectious agents.

* * * * *

UNITED STATES PATENT AND TRADEMARK OFFICE
CERTIFICATE OF CORRECTION

PATENT NO. : 11,701,433 B2
APPLICATION NO. : 16/619802
DATED : July 18, 2023
INVENTOR(S) : Lei et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 498 days.

Signed and Sealed this
Twelfth Day of November, 2024

Katherine Kelly Vidal
*Director of the United States Patent and Trademark Office*

SEQUENCE LISTING

<160> NUMBER OF SEQ ID NOS: 41

<210> SEQ ID NO 1
<211> LENGTH: 20
<212> TYPE: DNA
<213> ORGANISM: Artificial sequence
<220> FEATURE:
<223> OTHER INFORMATION: Synthetic

<400> SEQUENCE: 1
cattacctga aggccaagga                                          20

<210> SEQ ID NO 2
<211> LENGTH: 20
<212> TYPE: DNA
<213> ORGANISM: Artificial sequence
<220> FEATURE:
<223> OTHER INFORMATION: Synthetic

<400> SEQUENCE: 2
caattgtcca gtcccagagg                                        20

<210> SEQ ID NO 3
<211> LENGTH: 22
<212> TYPE: DNA
<213> ORGANISM: Artificial sequence
<220> FEATURE:
<223> OTHER INFORMATION: Synthetic

<400> SEQUENCE: 3
gtggtgttct tttcctcttg gg                                     22

<210> SEQ ID NO 4
<211> LENGTH: 21
<212> TYPE: DNA
<213> ORGANISM: Artificial sequence
<220> FEATURE:
<223> OTHER INFORMATION: Synthetic

<400> SEQUENCE: 4
acagcgaccc tttctcacta c                                      21

<210> SEQ ID NO 5
<211> LENGTH: 20
<212> TYPE: DNA
<213> ORGANISM: Artificial sequence
<220> FEATURE:
<223> OTHER INFORMATION: Synthetic

<400> SEQUENCE: 5
ctccagtctc agcaccatga                                        20

<210> SEQ ID NO 6
<211> LENGTH: 20
<212> TYPE: DNA
<213> ORGANISM: Artificial sequence
<220> FEATURE:
<223> OTHER INFORMATION: Synthetic

<400> SEQUENCE: 6
gctcccctct ggttttaagg                                        20

<210> SEQ ID NO 7
<211> LENGTH: 20
<212> TYPE: DNA
<213> ORGANISM: Artificial sequence
<220> FEATURE:
<223> OTHER INFORMATION: Synthetic

<400> SEQUENCE: 7
ctgagaggca gcgaactcat                                        20

<210> SEQ ID NO 8
<211> LENGTH: 20
<212> TYPE: DNA
<213> ORGANISM: Artificial sequence
<220> FEATURE:
<223> OTHER INFORMATION: Synthetic -continued

```
<400> SEQUENCE: 8
agcatcttca ccgtcaggtc                                              20

<210> SEQ ID NO 9
<211> LENGTH: 23
<212> TYPE: DNA
<213> ORGANISM: Artificial sequence
<220> FEATURE:
<223> OTHER INFORMATION: Synthetic

<400> SEQUENCE: 9
cccacctaca gcatgtccta ctc                                          23

<210> SEQ ID NO 10
<211> LENGTH: 22
<212> TYPE: DNA
<213> ORGANISM: Artificial sequence
<220> FEATURE:
<223> OTHER INFORMATION: Synthetic

<400> SEQUENCE: 10
tggagtggga ggaagaggta ac                                           22

<210> SEQ ID NO 11
<211> LENGTH: 24
<212> TYPE: DNA
<213> ORGANISM: Artificial sequence
<220> FEATURE:
<223> OTHER INFORMATION: Synthetic

<400> SEQUENCE: 11
tgagacttgg gcttaccatt gggt                                         24

<210> SEQ ID NO 12
<211> LENGTH: 24
<212> TYPE: DNA
<213> ORGANISM: Artificial sequence
<220> FEATURE:
<223> OTHER INFORMATION: Synthetic

<400> SEQUENCE: 12
tctttaatgg gccacaacag ggct                                         24

<210> SEQ ID NO 13
<211> LENGTH: 24
<212> TYPE: DNA
<213> ORGANISM: Artificial sequence
<220> FEATURE:
<223> OTHER INFORMATION: Synthetic

<400> SEQUENCE: 13
gagcaggttc accagcttta tgat                                         24

<210> SEQ ID NO 14
<211> LENGTH: 19
<212> TYPE: DNA
<213> ORGANISM: Artificial sequence
<220> FEATURE:
<223> OTHER INFORMATION: Synthetic

<400> SEQUENCE: 14
aacggatggt ggcaaatga                                               19

<210> SEQ ID NO 15
<211> LENGTH: 19
```

```
<212> TYPE: DNA
<213> ORGANISM: Artificial sequence
<220> FEATURE:
<223> OTHER INFORMATION: Synthetic

<400> SEQUENCE: 15
agctgctatc atcgtcaac                                                    19

<210> SEQ ID NO 16
<211> LENGTH: 19
<212> TYPE: DNA
<213> ORGANISM: Artificial sequence
<220> FEATURE:
<223> OTHER INFORMATION: Synthetic

<400> SEQUENCE: 16
accgcagatc tcaccatag                                                    19

<210> SEQ ID NO 17
<211> LENGTH: 19
<212> TYPE: DNA
<213> ORGANISM: Artificial sequence
<220> FEATURE:
<223> OTHER INFORMATION: Synthetic

<400> SEQUENCE: 17
gtgccgaccg actcatctg                                                    19

<210> SEQ ID NO 18
<211> LENGTH: 19
<212> TYPE: DNA
<213> ORGANISM: Artificial sequence
<220> FEATURE:
<223> OTHER INFORMATION: Synthetic

<400> SEQUENCE: 18
gtcctgcact catccaagc                                                    19

<210> SEQ ID NO 19
<211> LENGTH: 20
<212> TYPE: DNA
<213> ORGANISM: Artificial sequence
<220> FEATURE:
<223> OTHER INFORMATION: Synthetic

<400> SEQUENCE: 19
atgctgagga tttggaaagg                                                   20

<210> SEQ ID NO 20
<211> LENGTH: 21
<212> TYPE: DNA
<213> ORGANISM: Artificial sequence
<220> FEATURE:
<223> OTHER INFORMATION: Synthetic

<400> SEQUENCE: 20
cagagggcta caatgtgatg g                                                 21

<210> SEQ ID NO 21
<211> LENGTH: 20
<212> TYPE: DNA
<213> ORGANISM: Artificial sequence
<220> FEATURE:
<223> OTHER INFORMATION: Synthetic

<400> SEQUENCE: 21
```

```
ccagctccaa gaaaggacga                                              20

<210> SEQ ID NO 22
<211> LENGTH: 21
<212> TYPE: DNA
<213> ORGANISM: Artificial sequence
<220> FEATURE:
<223> OTHER INFORMATION: Synthetic

<400> SEQUENCE: 22
cgccctgtag gtgaggttga t                                            21

<210> SEQ ID NO 23
<211> LENGTH: 20
<212> TYPE: DNA
<213> ORGANISM: Artificial sequence
<220> FEATURE:
<223> OTHER INFORMATION: Synthetic

<400> SEQUENCE: 23
gagcagtgtg gagttcgagg                                              20

<210> SEQ ID NO 24
<211> LENGTH: 20
<212> TYPE: DNA
<213> ORGANISM: Artificial sequence
<220> FEATURE:
<223> OTHER INFORMATION: Synthetic

<400> SEQUENCE: 24
tccggatcta ggcaggtttg                                              20

<210> SEQ ID NO 25
<211> LENGTH: 20
<212> TYPE: DNA
<213> ORGANISM: Artificial sequence
<220> FEATURE:
<223> OTHER INFORMATION: Synthetic

<400> SEQUENCE: 25
aatgagggcc atagggaagc                                              20

<210> SEQ ID NO 26
<211> LENGTH: 20
<212> TYPE: DNA
<213> ORGANISM: Artificial sequence
<220> FEATURE:
<223> OTHER INFORMATION: Synthetic

<400> SEQUENCE: 26
agccatccac tgggtaaagg                                              20

<210> SEQ ID NO 27
<211> LENGTH: 20
<212> TYPE: DNA
<213> ORGANISM: Artificial sequence
<220> FEATURE:
<223> OTHER INFORMATION: Synthetic

<400> SEQUENCE: 27
tctgaggaga gccagacgat                                              20

<210> SEQ ID NO 28
<211> LENGTH: 20
<212> TYPE: DNA
<213> ORGANISM: Artificial sequence
```

```
<220> FEATURE:
<223> OTHER INFORMATION: Synthetic

<400> SEQUENCE: 28
actctggtcc ccaatgacag                                               20

<210> SEQ ID NO 29
<211> LENGTH: 22
<212> TYPE: DNA
<213> ORGANISM: Artificial sequence
<220> FEATURE:
<223> OTHER INFORMATION: Synthetic

<400> SEQUENCE: 29
cggcacagtc attgaaagcc ta                                            22

<210> SEQ ID NO 30
<211> LENGTH: 21
<212> TYPE: DNA
<213> ORGANISM: Artificial sequence
<220> FEATURE:
<223> OTHER INFORMATION: Synthetic

<400> SEQUENCE: 30
gttgctgatg gcctgattgt c                                             21

<210> SEQ ID NO 31
<211> LENGTH: 23
<212> TYPE: DNA
<213> ORGANISM: Artificial sequence
<220> FEATURE:
<223> OTHER INFORMATION: Synthetic

<400> SEQUENCE: 31
gattagcgat gatgaaccag gtt                                           23

<210> SEQ ID NO 32
<211> LENGTH: 21
<212> TYPE: DNA
<213> ORGANISM: Artificial sequence
<220> FEATURE:
<223> OTHER INFORMATION: Synthetic

<400> SEQUENCE: 32
cctcccatct ccttcatcac a                                             21

<210> SEQ ID NO 33
<211> LENGTH: 22
<212> TYPE: DNA
<213> ORGANISM: Artificial sequence
<220> FEATURE:
<223> OTHER INFORMATION: Synthetic

<400> SEQUENCE: 33
gtggtgttct tttcctcttg gg                                            22

<210> SEQ ID NO 34
<211> LENGTH: 9
<212> TYPE: PRT
<213> ORGANISM: Artificial sequence
<220> FEATURE:
<223> OTHER INFORMATION: Synthetic

<400> SEQUENCE: 34

Arg Ala His Tyr Asn Ile Val Thr Phe
1               5
```

<210> SEQ ID NO 35
<211> LENGTH: 21
<212> TYPE: DNA
<213> ORGANISM: Artificial sequence
<220> FEATURE:
<223> OTHER INFORMATION: Synthetic

<400> SEQUENCE: 35
acagcgaccc tttctcacta c                                              21

<210> SEQ ID NO 36
<211> LENGTH: 20
<212> TYPE: DNA
<213> ORGANISM: Artificial sequence
<220> FEATURE:
<223> OTHER INFORMATION: Synthetic

<400> SEQUENCE: 36
ctccagtctc agcaccatga                                                20

<210> SEQ ID NO 37
<211> LENGTH: 20
<212> TYPE: DNA
<213> ORGANISM: Artificial sequence
<220> FEATURE:
<223> OTHER INFORMATION: Synthetic

<400> SEQUENCE: 37
gctcccctct ggttttaagg                                                20

<210> SEQ ID NO 38
<211> LENGTH: 21
<212> TYPE: DNA
<213> ORGANISM: Artificial sequence
<220> FEATURE:
<223> OTHER INFORMATION: Synthetic

<400> SEQUENCE: 38
cagagggcta caatgtgatg g                                              21

<210> SEQ ID NO 39
<211> LENGTH: 20
<212> TYPE: DNA
<213> ORGANISM: Artificial sequence
<220> FEATURE:
<223> OTHER INFORMATION: Synthetic

<400> SEQUENCE: 39
attataaata ccggccccgg                                                20

<210> SEQ ID NO 40
<211> LENGTH: 20
<212> TYPE: DNA
<213> ORGANISM: Artificial sequence
<220> FEATURE:
<223> OTHER INFORMATION: Synthetic

<400> SEQUENCE: 40
atgctgagga tttggaaagg                                                20

<210> SEQ ID NO 41
<211> LENGTH: 1255
<212> TYPE: PRT
<213> ORGANISM: Homo sapiens

<400> SEQUENCE: 41

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415
```

```
Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830
```

-continued

```
Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
        900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
        930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
        980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr
        1010                1015                1020

Leu Val Pro Gln Gln Gly Phe Phe Cys Pro Asp Pro Ala Pro Gly
        1025                1030                1035

Ala Gly Gly Met Val His His Arg His Arg Ser Ser Ser Thr Arg
        1040                1045                1050

Ser Gly Gly Gly Asp Leu Thr Leu Gly Leu Glu Pro Ser Glu Glu
        1055                1060                1065

Glu Ala Pro Arg Ser Pro Leu Ala Pro Ser Glu Gly Ala Gly Ser
        1070                1075                1080

Asp Val Phe Asp Gly Asp Leu Gly Met Gly Ala Ala Lys Gly Leu
        1085                1090                1095

Gln Ser Leu Pro Thr His Asp Pro Ser Pro Leu Gln Arg Tyr Ser
        1100                1105                1110

Glu Asp Pro Thr Val Pro Leu Pro Ser Glu Thr Asp Gly Tyr Val
        1115                1120                1125

Ala Pro Leu Thr Cys Ser Pro Gln Pro Glu Tyr Val Asn Gln Pro
        1130                1135                1140

Asp Val Arg Pro Gln Pro Pro Ser Pro Arg Glu Gly Pro Leu Pro
        1145                1150                1155

Ala Ala Arg Pro Ala Gly Ala Thr Leu Glu Arg Pro Lys Thr Leu
        1160                1165                1170

Ser Pro Gly Lys Asn Gly Val Val Lys Asp Val Phe Ala Phe Gly
        1175                1180                1185

Gly Ala Val Glu Asn Pro Glu Tyr Leu Thr Pro Gln Gly Gly Ala
        1190                1195                1200

Ala Pro Gln Pro His Pro Pro Ala Phe Ser Pro Ala Phe Asp
        1205                1210                1215

Asn Leu Tyr Tyr Trp Asp Gln Asp Pro Pro Glu Arg Gly Ala Pro
        1220                1225                1230
```

```
Pro Ser Thr Phe Lys Gly Thr  Pro Thr Ala Glu Asn  Pro Glu Tyr
    1235                1240                1245

Leu Gly Leu Asp Val Pro Val
    1250            1255
```